United States Patent
Brown et al.

(10) Patent No.: US 11,220,483 B2
(45) Date of Patent: Jan. 11, 2022

(54) TETRAHYDRO-BENZO[D]AZEPINE DERIVATIVES AS GPR120 MODULATORS

(71) Applicant: CALDAN THERAPEUTICS LIMITED, Edinburgh (GB)

(72) Inventors: Jane Brown, Nottingham (GB); Stephen Connolly, York (GB); Steffen V. F. Hansen, Copenhagen (DK); Gavin Milne, Nottingham (GB); Bharat Shimpukade, Bangalore (IN); Don Smyth, Nottingham (GB); Gerard Thomas, Nottingham (GB); Trond Ulven, Copenhagen (DK); Matjaz Brvar, Zagorje ob Savi (SI); Aaron Rigby, Nottingham (GB)

(73) Assignee: CALDAN THERAPEUTICS LTD, Edinburgh (GB)

( * ) Notice: Subject to any disclaimer, the term of this patent is extended or adjusted under 35 U.S.C. 154(b) by 0 days.

(21) Appl. No.: 16/496,786

(22) PCT Filed: Mar. 26, 2018

(86) PCT No.: PCT/GB2018/000047
§ 371 (c)(1),
(2) Date: Sep. 23, 2019

(87) PCT Pub. No.: WO2018/172727
PCT Pub. Date: Sep. 27, 2018

(65) Prior Publication Data
US 2020/0317619 A1    Oct. 8, 2020

(51) Int. Cl.
| | | |
|---|---|---|
| C07D 217/04 | (2006.01) | |
| C07D 401/04 | (2006.01) | |
| C07D 405/04 | (2006.01) | |
| A61K 31/47 | (2006.01) | |
| A61K 31/4725 | (2006.01) | |
| A61P 3/10 | (2006.01) | |
| C07D 223/16 | (2006.01) | |

(52) U.S. Cl.
CPC ............. *C07D 223/16* (2013.01); *A61P 3/10* (2018.01); *C07D 217/04* (2013.01); *C07D 401/04* (2013.01); *C07D 405/04* (2013.01)

(58) Field of Classification Search
CPC .. C07D 217/04; C07D 401/04; C07D 405/04; A61K 31/47; A61K 31/4725; A61P 3/10
See application file for complete search history.

(56) References Cited

FOREIGN PATENT DOCUMENTS

| EP | 2298750 A1 | 3/2011 |
|---|---|---|
| WO | 2007/022280 A1 | 2/2007 |
| WO | 2007/089557 A2 | 8/2007 |
| WO | 2008/053446 A2 | 5/2008 |
| WO | 2008/103500 A1 | 8/2008 |
| WO | 2013/019682 A1 | 2/2013 |
| WO | 2016/022446 A1 | 2/2016 |
| WO | 2016/022448 A1 | 2/2016 |
| WO | 2016/105118 A2 | 6/2016 |
| WO | 2017/201683 A1 | 11/2017 |

OTHER PUBLICATIONS

International Search Report and Written Opinion for corresponding Application No. PCT/GB2018/000047 (dated Jun. 7, 2018).
Great Britain Search Report for corresponding Application No. GB1704714.3 (dated Jan. 8, 2018).
Buzard et al., "Discovery and Characterization of Potent and Selective 4-Oxo-4-(5-(5-phenyl-1,2,4-oxadiazol-3-yl)indol-1-yl)butanoic Acids as S1P1 Agonists," Bioorganic & Medicinal Chemistry Letters 21:6013-6018 (2011).
Ichimura et al., "Dysfunction of Lipid Sensor GPR120 Leads to Obesity in Both Mouse and Human," Nature 483(7389):350-354 (2012).
Oh et al., "A Gpr120-Selective Agonist Improves Insulin Resistance and Chronic Inflammation in Obese Mice," Nature Medicine 20(8):942-947 (2014) (electronically published preprint).
Zhang et al., "Discovery of an Isothiazole-Based Phenylpropanoic Acid GPR120 Agonist as a Development Candidate for Type 2 Diabetes," ACS Med. Chem. Lett. 8:947-952 (2017).
Azevedo et al., "Non-Acidic Free Fatty Acid Receptor 4 Agonist with Antidiabetic Activity," J. Med. Chem. 59 (19):8868-8878 (2016).
Liu et al., "Omega-3 Fatty Acids and Other FFA4 Agonists Inhibit Growth Factor Signaling in Human Prostate Cancer Cells," J. Pharmacol. Exp. Ther. 352:380-394 (2015).

(Continued)

*Primary Examiner* — Bruck Kifle
(74) *Attorney, Agent, or Firm* — Troutman Pepper Hamilton Sanders LLP (Rochester)

(57) ABSTRACT

Novel tetrahydroisoquinoline and tetrahydrobenzazepine compounds of formula (I) capable of modulating the G-protein-coupled receptor GPR120, compositions comprising the compounds, and methods for their use for controlling insulin levels in vivo and for the treatment of conditions such as of diabetes, inflammation, obesity and metabolic diseases.

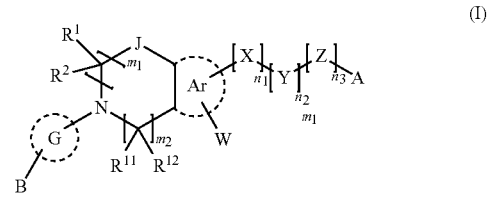

(I)

11 Claims, No Drawings

(56) References Cited

OTHER PUBLICATIONS

Shin et al., "G-Protein-Coupled Receptor 120 Mediates DHA-Induced Apoptosis by Regulating IP3R, ROS and, ER Stress Levels in Cisplatin-Resistant Cancer Cells," Molecules and Cells 42(3):252-261 (2019).
Chen et al., "G-Protein-Coupled Receptor 120 Agonist III Improves Hepatic Inflammation and ER Stress in Steatohepatitis," Digestive Diseases and Sciences 66:1090-1096 (2021) (electronically published preprint).
Nakamoto et al., "DHA Supplementation Prevent the Progression of NASH via GPR120 Signaling," Eur. J. Pharmacol. 820:31-38 (2018).
Secor et al., "Free Fatty Acid Receptors as Mediators and Therapeutic Targets in Liver Disease," Front. Physiol. 12:656441 (2021).
Wei et al., "Activation of GPR120 in Podocytes Ameliorates Kidney Fibrosis and Inflammation in Diabetic Nephropathy," Acta Pharmacologica Sinica 42:252-263 (2021)(electronically published preprint).
Son et al., "Free Fatty Acid Receptor 4 (FFA4) Activation Ameliorates 2,4-Dinitrochlorobenzene-Induced Atopic Dermatitis by Increasing Regulatory T Cells in Mice," Acta Pharmacologica Sinica 41:337-1347 (2020) (electronically published preprint).
Forbes et al., "Mechanisms of Diabetic Complications," Physiol. Rev. 93:137-188 (2013) ("Forbes").

TETRAHYDRO-BENZO[D]AZEPINE DERIVATIVES AS GPR120 MODULATORS

The present invention relates to novel compounds capable of modulating the G-protein-coupled receptor GPR120, compositions comprising the compounds, and methods for their use for controlling insulin levels in vivo and for the treatment of conditions such as of diabetes, inflammation, obesity and metabolic diseases.

With 350 million diabetics worldwide, a number that has more than doubled since 1980, diabetes is currently the fourth leading cause of death and represents an enormous social and economic burden. Type 2 diabetes constitutes 90-95% of all diabetes cases. It is closely associated with obesity and its prevalence is expected to continue to increase at at least the current rate. Although lifestyle intervention like healthy diet and exercise is regarded as the most efficient means to prevent and manage the disease, pharmaceutical intervention is frequently necessary. There is however no cure for type 2 diabetes and current therapeutics have significant shortcomings.

Activation of GPR120 is reported to result in glucagon-like peptide 1 (GLP-1) secretion (Hirasawa, et al, Nat. Med. 2005, 11, 90-94), increased insulin sensitivity in adipose tissue, decreased lipolysis and decreased inflammation (Oh, et al, Cell 2010, 142, 687-698). Dysfunctional GPR120 is reported to lead to obesity, which implies that agonists of the receptor may have potential as anti-obesity therapeutics (Ichimura, et al, 2012, doi:10.1038/nature10798). GPR120 is thus an interesting target for treatment of type 2 diabetes. Several patent applications claim GPR120 modulators, including WO2008/066131, WO2008/103500, WO2008/103501, WO2009/038204, WO2009/147990, WO2010/008831, WO2010/048207, WO2010/080537, WO2010/104195, and WO2011/072132, WO2014/069963, WO2014/149987, WO2014/151247, WO2014/159054, WO2014/159061, WO2014/159794, WO2014/159802, WO2014/209034, WO2015/125085, WO2015/134038, WO2015/134039, WO2016/012965, WO2016/038540, WO2016/040222, WO2016/040223, WO2016/040225, WO2016/105112 and WO2016/125182.

There is currently no cure for type 2 diabetes but a number of different types of drugs are available to treat the condition. Metformin is the most commonly prescribed drug, despite being one of the oldest on the market and having frequent gastrointestinal side effects. Sulfonylureas (SUs) are insulin secretagogues commonly used in treatment of type 2 diabetes, but they give rise to the serious problem that they increase the risk of hypoglycaemia and often lead to weight gain. Insulin treatment is also common and carries the same side-effects. Thiazolidinedione drugs (TZDs) have also been widely used but concerns over enhanced risk of heart disease have resulted in stringent limitations on their use and calls for their removal from the market. As such, despite the recent approval by regulatory authorities of new classes of anti-diabetic medicines based on either longer-duration analogues of GLP-1, inhibition of degradation of this incretin by DPP-4 inhibitors or sodium-glucose cotransporter-2 (SGLT-2) inhibitors, new treatments are required urgently. GPR120 agonists may provide improved type 2 diabetes therapeutics alone, or in conjunction with other therapeutics including any of the established therapeutics mentioned above.

The present invention provides a novel group of compounds that are believed to be GPR120 agonists. GPR120 agonists are useful in the treatment of diabetes and other related diseases including non-alcoholic steatohepatitis (NASH), non-alcoholic fatty liver disease (NAFLD), metabolic syndrome, dyslipidaemia, insulin resistance, and complications of diabetes. Non-alcoholic fatty liver disease (NAFLD) is a condition in which fat builds up in the liver. Non-alcoholic steatohepatitis (NASH) is a type of NAFLD in which the subject has inflammation and liver cell damage as well as fat in the liver.

According to a first aspect of the invention, there is provided a compound of general formula (I):

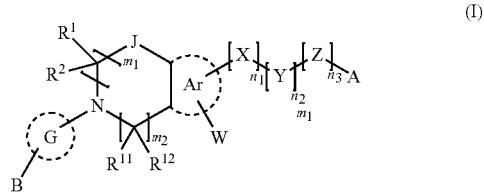

(I)

wherein Ar is 6-membered aryl, 5- or 6-membered heteroaryl or 5- or 6-membered cycloalkyl;

$m_1$ and $m_2$ are independently selected from 0, 1 or 2 with the proviso that $m_1 \neq m_2$ when $m_1$ or $m_2=0$ or when $m_1$ or $m_2=2$;

J is —$C(R^{21}R^{22})$—, —O—, —$N(R^{21})$— or —S— with the proviso that when J is —O—, —$N(R^{21})$— or —S—, $m_1$ is 2;

X is —O—, —S— or —$C(R^{31}R^{32})$—, Y is —O— or —$C(R^{41}R^{42})$—, Z is —$C(R^{51}R^{52})$—, and $n_1$, $n_2$ and $n_3$ are independently selected from 0 or 1 with the proviso that at least one of $n_1$, $n_2$ and $n_3$ must be 1 and at least one of X, Y or Z must be —$C(R^{31}R^{32})$—, —$C(R^{41}R^{42})$—, or —$C(R^{51}R^{52})$— respectively;

when X and Y are —$C(R^{31}R^{32})$— and —$C(R^{41}R^{42})$— respectively, $R^{31}$ and $R^{41}$ may be combined to form, together with X and Y, a $(C_3-C_6)$cycloalkyl ring which may be optionally substituted by $(C_1-C_3)$alkyl or halo;

when Y and Z are —$C(R^{41}R^{42})$— and —$C(R^{51}R^{52})$— respectively, $R^{41}$ and $R^{51}$ may be combined to form, together with Y and Z, a $(C_3-C_6)$cycloalkyl ring which may be optionally substituted by $(C_1-C_3)$alkyl or halo;

when X, Y and Z are —$C(R^{31}R^{32})$—, —$C(R^{41}R^{42})$— and —$C(R^{51}R^{52})$— respectively, $R^{31}$ and $R^{51}$ may form, together with X, Y and Z a $(C_4-C_7)$cycloalkyl ring which may be optionally substituted by $(C_1-C_3)$alkyl or halo;

$R^1$, $R^2$, $R^{11}$, $R^{12}$, $R^{21}$, $R^{22}$, $R^{31}$, $R^{32}$, $R^{41}$, $R^{42}$, $R^{51}$, and $R^{52}$ are independently selected from hydrogen, deuterium, halo, or $(C_1-C_3)$alkyl optionally substituted by halo;

A is —$CO_2H$, —$CO_2R^3$, —$CH_2OH$, tetrazolyl, 3-hydroxyisoxazol-5-yl or an acid bioisostere;

$R^3$ is $(C_1-C_6)$alkyl, or $(C_1-C_6)$cycloalkyl;

Ar is optionally substituted 1, 2 or 3 times by W, where W is $(C_1-C_{10})$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, or optionally substituted arylalkyl, and when Ar is substituted by a plurality of substituents, each substituent is selected independently;

G is an optionally substituted 6- to 10-membered aryl, 5- to 10-membered heteroaryl, or fused aryl or heteroaryl ring system;

G is optionally substituted one or more times by B, where B is $(C_1-C_{10})$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, optionally substituted arylalkyl, cyano, or E-M where E is —O—, —S— or —N($R^4$)— and M is optionally substituted $(C_1-C_7)$alkyl, $(C_3-C_7)$cycloalkyl, fluoro$(C_1-C_3)$alkyl, a 5- to 10-membered heterocyclic group or an optionally substituted 6- to 10-membered aryl group, and when G is substituted by a plurality of substituents, each substituent is selected independently;

$R^4$ is hydrogen, deuterium, or $(C_1-C_3)$alkyl optionally substituted by halo;

or a pharmaceutically acceptable salt or solvate (eg hydrate) thereof, or corresponding N-oxide or prodrug (eg ester prodrug).

Definitions

As used in the specification and appended claims, unless specified to the contrary, the following terms have the meaning indicated:

The term "alkyl", by itself or as part of another substituent, means, unless otherwise stated, a straight or branched chain hydrocarbon radical, which is fully saturated, having one to twelve carbon atoms or the number of carbon atoms designated (eg, $C_1-C_{10}$ means one to ten carbons), and which is attached to the rest of the molecule by a single bond. Examples of alkyl groups include methyl, ethyl, n-propyl, isopropyl, n-butyl, t-butyl, isobutyl, sec-butyl, and homologs and isomers of, for example, n-pentyl, n-hexyl, n-heptyl, n-octyl, and the like. "Alkyl" may mean $(C_1-C_{10})$, $(C_1-C_9)$, $(C_1-C_8)$, $(C_1-C_7)$, $(C_1-C_6)$, $(C_1-C_5)$, $(C_1-C_4)$ or $(C_1-C_3)$alkyl. Preferred alkyl groups typically have one to six carbon atoms or one to four carbon atoms.

The term "alkenyl", by itself or as part of another substituent, means a straight or branched chain hydrocarbon radical, or combination thereof, which is mono- or polyunsaturated, having two to twelve carbon atoms or the number of carbon atoms designated (ie, $C_2-C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl), and higher homologs and isomers thereof. "Alkenyl" may mean $(C_2-C_8)$, $(C_2-C_7)$, $(C_2-C_6)$, $(C_2-C_5)$, $(C_2-C_4)$alkenyl.

The term "alkynyl", by itself or as part of another substituent, means a straight or branched chain hydrocarbon radical, or combination thereof, which may be mono- or polyunsaturated, having two to twelve carbon atoms or the number of carbon atoms designated (ie, $C_2-C_8$ means two to eight carbons) and one or more triple bonds. Examples of alkynyl groups include ethynyl, 1- and 2-propynyl, 3-butynyl, and higher homologs and isomers thereof. "Alkynyl" may mean $(C_2-C_8)$, $(C_2-C_7)$, $(C_2-C_6)$, $(C_2-C_5)$, $(C_2-C_4)$ alkynyl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. "Alkyl" is defined as set out above. Similarly, the term dialkylamino refers to an amino group having two attached alkyl groups. The alkyl groups of a dialkylamino may be the same or different.

The term "heteroalkyl," by itself or in combination with another term, means, unless otherwise stated, a stable straight or branched chain hydrocarbon radical, or combinations thereof, consisting of carbon atoms and from one to three heteroatoms selected from the group consisting of O, N, and S, and wherein the nitrogen and sulfur atoms may optionally be oxidized, and the nitrogen heteroatom may optionally be quaternised. The heteroatom(s) O, N, and S may be placed at any position of the heteroalkyl group. Examples include —$CH_2CH_2OCH_3$, —$CH_2CH_2NHCH_3$, —$CH_2CH_2N(CH_3)CH_3$, —$CH_2SCH_2CH_3$, —$CH_2CH_2S(O)$ $CH_3$, —$CH_2CH_2S(O)_2CH_3$, and —$CH_2CH=N—OCH_3$. The atom at the substitution position is always carbon. For example, —$OCH_3$ or —$OCH_2CH_3$ are not heteroalkyls. Up to two heteroatoms may be consecutive, such as, for example, —$CH_2NH—OCH_3$. When a prefix such as $(C_2-C_8)$ is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group is an oxyalkyl group. For instance, $(C_2-C_8)$oxyalkyl is meant to include, for example —$CH_2O—CH_3$ (a $C_3$-oxyalkyl group with two carbon atoms and one oxygen replacing a carbon atom), —$CH_2CH_2CH_2CH_2OH$, and the like, but not —$OCH_2CH_2CH_2CH_3$.

The term "cycloalkyl" means a cyclic hydrocarbon radical, which is fully saturated and attached to the rest of the molecule by a single bond, having three to ten carbon atoms or the number of carbon atoms designated. Examples of cycloalkyl include cyclopentyl, cyclohexyl, 1-cyclohexenyl, 3-cyclohexenyl, cycloheptyl, and the like.

The term "heterocycloalkyl" means a 3- to 10-membered cyclic hydrocarbon radical consisting of one to nine carbon atoms and one to four heteroatoms selected from the group consisting of O, N and S, and wherein the nitrogen and sulfur atoms may optionally be oxidized and the nitrogen atom may optionally be quaternised. The heteroatoms(s) O, N and S may be placed at any position of the heterocycloalkyl group, but the atom at the substitution position is always carbon. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 4,5-dihydroisoxazol-3-yl, and the like. The term "heterocycloalkyl" includes fully saturated compounds such as piperidine and compounds with partial saturation that are not aromatic. Examples of such groups include, but are not limited to, an imidazoline, oxazoline, or isoxazoline.

The terms "halo" or "halogen," by themselves or as part of another substituent, mean, unless otherwise stated, a fluorine, chlorine, bromine, or iodine radical. Additionally, terms such as "haloalkyl", are meant to include alkyl substituted with halogen atoms which can be the same or different, in a number ranging from one to (2m+1), where m is the total number of carbon atoms in the alkyl group. For example, the term "halo$(C_1-C_4)$alkyl" is meant to include trifluoromethyl, 2,2,2-trifluoroethyl, 4-chlorobutyl, 3-bromopropyl, and the like.

Thus, the term "haloalkyl" includes monohaloalkyl (alkyl substituted with one halogen atom) and polyhaloalkyl (alkyl substituted with halogen atoms in a number ranging from two to (2m+1) halogen atoms). The term "perhaloalkyl" means, unless otherwise stated, alkyl substituted with (2m+1) halogen atoms, where m is the total number of carbon atoms in the alkyl group. For example, the term "perhalo $(C_1-C_4)$alkyl", is meant to include trifluoromethyl, pentachloroethyl, 1,1,1-trifluoro-2-bromo-2-chloroethyl, and the like.

Similarly, the term "fluoroalkyl" includes monofluoroalkyl (alkyl substituted with one fluoro atom) and polyfluoroalkyl (alkyl substituted with fluorine atoms in a number ranging from two to (2m+1) fluorine atoms). For example, the term "fluoro($C_1$)alkyl" is meant to include —$CF_3$, —$CF_2H$ and —$CH_2F$.

The term "aryl" means, unless otherwise stated, a polyunsaturated, typically aromatic, hydrocarbon ring radical. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternised. A heteroaryl group can be attached to the remainder of the molecule through a heteroatom. Non-limiting examples of aryl and heteroaryl groups include phenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl and 4-pyridazinyl.

The term "fused aryl" means, unless otherwise stated, an aryl which is fused with another cyclic aromatic or non-aromatic ring. The term "fused heteroaryl" means, unless otherwise stated, a heteroaryl which is fused with another cyclic aromatic or non-aromatic ring. Examples of fused aryl and fused heteroaryl groups include imidazo[1,2-a]pyridine, 1-naphthyl, 2-naphthyl, 4-biphenyl, dibenzofuryl, 5-benzothiazolyl, 2-benzoxazolyl, 5-benzoxazolyl, benzooxadiazolyl, purinyl, 2-benzimidazolyl, 5-indolyl, 1H-indazolyl, carbazolyl, carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl.

Preferably, the term "aryl" refers to a phenyl group which is unsubstituted or substituted. Preferably, the term "heteroaryl" refers to a pyrrolyl, pyrazolyl, imidazolyl, pyrazinyl, oxazolyl, oxadiazolyl, isoxazolyl, thiazolyl, furyl, thienyl (thiophenyl), pyridyl, or pyrimidyl which is substituted or unsubstituted. Preferably, the term "fused aryl" refers to naphthyl, indanyl, indenyl, or quinolyl. Preferably, the term "fused heteroaryl" refers to quinolyl, benzothiazolyl, purinyl, benzimidazolyl, indolyl, isoquinolyl, triazolyl, tetrazolyl, or quinoxalinyl group which is unsubstituted or substituted.

Each of the above terms (eg, "alkyl," "heteroalkyl," "aryl" and "heteroaryl") is meant to include both substituted and unsubstituted forms of the indicated radical, unless otherwise indicated. Preferred substituents for each type of radical are provided below.

"Optional" or "optionally" means that the subsequently described condition may or may not occur. For example, "optionally substituted aryl" means that the aryl radical may carry one or more substituents or may be unsubstituted. Unless indicated otherwise, "optionally substituted" means that one or more substituents may be present, and where there is more than one substituent, those substituents may be the same or different.

The term "substituent", which may be present on alkyl or heteroalkyl radicals, as well as those groups referred to as alkenyl, heteroalkenyl, alkynyl, cycloalkyl, heterocycloalkyl, cycloalkenyl and heterocycloalkenyl, or on other groups indicated as "optionally substituted", can be a variety of groups selected from: —OR', =O, =NR', =N—OR', —NR'R", —SR', halogen, —OC(O)R', —C(O)R', —$CO_2$R', —CONR'R", —OC(O)NR'R", —NR"C(O)R', —NR'—C(O)NR"R"', —NR"$CO_2$R', —NH—C(NH$_2$)=NH, —NR'C(NH$_2$)=NH, —NH—C(NH$_2$)=NR', —SiR'R"R"', —S(O)R', —$SO_2$R', —$SO_2$NR"R", —NR"$SO_2$R, —CN, ($C_1$-$C_6$)alkyl, —($C_2$-$C_5$)alkynyl, —($C_2$-$C_5$)alkenyl, and —$NO_2$, in a number ranging from one to three, with those groups having one or two substituents being particularly preferred. Other suitable substituents include aryl and heteroaryl groups. R', R" and R"' each independently refer to hydrogen, deuterium, unsubstituted ($C_1$-$C_6$)alkyl and ($C_2$-$C_6$)heteroalkyl, unsubstituted aryl, aryl substituted with one to three halogens, unsubstituted ($C_1$-$C_4$)-alkyl, ($C_1$-$C_4$)-alkoxy or ($C_1$-$C_4$)-thioalkoxy groups, halo($C_1$-$C_4$)alkyl, or aryl-($C_1$-$C_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl or heteroalkyl group will have from zero to three substituents, with those groups having two or fewer substituents being preferred in the present invention. An alkyl or heteroalkyl radical may be unsubstituted or monosubstituted. An alkyl or heteroalkyl radical may be unsubstituted.

Preferred substituents for the alkyl and heteroalkyl radicals are selected from: —OR', =O, —NR'R", —SR', halogen, —OC(O)R', —C(O)R', —$CO_2$R', —CONR'R", —OC(O)NR'R", —NR"C(O)R', —NR"$CO_2$R', —NR'$SO_2$NR"R', —S(O)R', —$SO_2$R', —$SO_2$NR'R", —NR"$SO_2$R', —CN, —($C_2$-$C_5$)alkynyl, —($C_2$-$C_5$)alkenyl and —$NO_2$, where R' and R" are as defined above. Further preferred substituents are selected from: —OR', =O, —NR'R", halogen, —OC(O)R', —$CO_2$R', —CONR'R", —OC(O)NR'R", —NR"C(O)R', —NR'$CO_2$R", —NR'—$SO_2$NR"R"', —$SO_2$R', —$SO_2$NR'R", —NR"$SO_2$R', —CN, —($C_2$-$C_5$)alkynyl, —($C_2$-$C_5$)alkenyl, and —$NO_2$.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NHC(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, deuterium, ($C_1$-$C_4$) alkyl and heteroalkyl, unsubstituted aryl and heteroaryl, (unsubstituted aryl)-($C_1$-$C_4$)alkyl, (unsubstituted aryl)oxy-($C_1$-$C_4$)alkyl, —($C_2$-$C_5$)alkynyl, and —($C_2$-$C_5$)alkenyl.

When deuterium is selected as a substituent the resulting compound is a "deuterated" compound in which one or more hydrogen atoms has been intentionally replaced with one or more deuterium atoms. Compounds containing trace levels of the deuterium isotope by virtue of its natural abundance are not "deuterated". Deuteration of a drug may influence its biological properties, for example its rate of metabolism.

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not.

The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolysed to the carboxylic acid, the active entity. Additional examples include peptidyl derivatives of a compound. As used herein and unless otherwise indicated, the term "stereoisomer" or "stereomerically pure" means one stereoisomer of a compound that is substantially free of other stereoisomers of that compound. For example, a stereomerically pure compound having one chiral centre will be substantially free of the opposite enantiomer of the compound. A stereomerically pure compound having two chiral centres will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centres, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesised or resolved using standard techniques such as chiral columns or chiral resolving agents. See, eg, Jacques, J., et al, Enantiomers, Racemates and Resolutions (Wiley-Interscience, New York, 1981); Wilen, S. H., et al (1997) Tetrahedron 33:2725; Eliel, E. L., Stereochemistry of Carbon Compounds (McGraw-Hill, N Y, 1962); and Wilen, S. H., Tables of Resolving Agents and Optical Resolutions p. 268 (EX. Eliel, Ed., Univ. of Notre Dame Press, Notre Dame, Ind., 1972).

Particular embodiments of the compounds of formula (I) described in the first aspect of the invention are set out below. It is to be understood that this invention covers all appropriate combinations of the substituents referred to herein, and that, where alternatives are provided for any one substituent, the invention covers all lists which may be formed by combinations of these alternatives.

In certain embodiments, Ar is 6-membered aryl or 5- or 6-membered heteroaryl. Ar may be phenyl, cyclohexyl, cyclopentyl, pyrrole, furan or thiophene. Ar may be phenyl, cyclohexyl or pyrrole. Ar may be phenyl.

In certain embodiments, $m_1$ and $m_2$ are chosen such that $m_1+m_2=2$, ie $m_1=m_2=1$, or $m_1=2$ and $m_2=0$, or $m_1=0$ and $m_2=2$.

In certain embodiments, $m_1$ and $m_2$ are 1.

In certain embodiments, $m_1$ and $m_2$ are 1 and J is —C($R^{21}R^{22}$)—.

In certain embodiments, $n_1$ is O, Y is —C($R^{41}R^{42}$)— and Z is —C($R^{51}R^{52}$)—.

In certain embodiments, A is —CO$_2$H.

In certain embodiments X and Y are —C($R^{31}R^{32}$)— and —C($R^{41}R^{42}$)— respectively, and $R^{31}$ and $R^{41}$ are combined to form, together with X and Y, a cyclopropyl ring, for example

In certain embodiments X, Y and Z are —C($R^{31}R^{32}$)—, —C($R^{41}R^{42}$)— and —C($R^{51}R^{52}$)— respectively, and $R^{31}$ and $R^{51}$ form, together with X, Y and Z a cyclobutyl ring, for example.

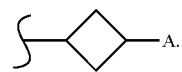

In certain embodiments, Ar is 6-membered aryl and $m_1$ and $m_2$ are chosen such that $m_1+m_2=2$. X—Y—Z-A may then be connected to Ar in the 6- or 7-position. Ar may be substituted by W in the 5-, 6-, 7- or 8-position.

In certain embodiments, W is optionally substituted ($C_1$-$C_6$)alkyl, ($C_3$-$C_6$)cycloalkyl, halo or optionally substituted ($C_1$-$C_6$)alkoxy. W may be halo. W may be fluoro.

In certain embodiments, Ar is substituted 1, 2 or 3 times with W. Ar may be substituted 1 or 2 times by W.

In certain embodiments, G is an optionally substituted 6-membered aryl or 6-membered heteroaryl. G may be optionally substituted phenyl or pyridine.

In certain embodiments, B is ($C_1$-$C_6$)alkyl, ($C_2$-$C_{10}$)alkenyl, ($C_2$-$C_{10}$)alkynyl, ($C_1$-$C_{10}$)alkoxy, ($C_2$-$C_{10}$)dialkylamino, ($C_1$-$C_{10}$)alkylthio, ($C_2$-$C_{10}$)heteroalkyl, ($C_3$-$C_{10}$)cycloalkyl, ($C_3$-$C_{10}$)heterocycloalkyl, halo, ($C_1$-$C_{10}$)haloalkyl, ($C_1$-$C_{10}$)perhaloalkyl, optionally substituted aryl, optionally substituted heteroaryl, optionally substituted arylalkyl, cyano, or E-M- where E is —O—, —S— or —N($R^4$)— and M is optionally substituted ($C_1$-$C_7$)alkyl, ($C_3$-$C_7$)cycloalkyl, fluoro($C_1$-$C_3$)alkyl, a 5- to 10-membered heterocyclic group or an optionally substituted 6- to 10-membered aryl group.

M may be substituted one or more times by K where K is ($C_1$-$C_6$)alkoxy, halo or —$NR^5$ and $R^5$ is hydrogen, deuterium, or ($C_1$-$C_3$)alkyl optionally substituted by halo.

When E is —O—, M may be ($C_3$-$C_7$)cycloalkyl, fluoro($C_1$-$C_3$)alkyl or an optionally substituted 6- to 10-membered aryl group and preferably M is cyclobutyl, —$CF_3$ or phenyl optionally substituted by halo and/or ($C_1$-$C_3$)alkyl.

B may be selected from halo, ($C_1$-$C_6$)alkyl optionally substituted with halo, ($C_1$-$C_6$)cycloalkyl optionally substituted with halo, ($C_1$-$C_6$)alkoxy optionally substituted with halo or E-M where E is —O—, —S— or —N($R^4$)— and M is optionally substituted ($C_1$-$C_7$)alkyl, ($C_3$-$C_7$)cycloalkyl, a 5- to 10-membered heterocyclic group or a 6- to 10-membered aryl group. B may be halo or E-M where E is —O—, —S— or —N($R^4$)— and M is optionally substituted ($C_1$-$C_7$)alkyl, ($C_3$-$C_7$)cycloalkyl, fluoro($C_1$-$C_3$)alkyl, a 5- to 10-membered heterocyclic group or an optionally substituted 6- to 10-membered aryl group.

G may be substituted 1, 2, 3, 4 or 5 times with B. G may be substituted 2 or 3 times by B.

When G is substituted more than once with B, B may include E-M and/or halo.

If G is 6-membered aryl or 6-membered heteroaryl, G may be substituted twice by B in a 2,5- or 3,5-substitution pattern, or three times by B in a 2,3,5-substitution pattern. G may be substituted by halo in the 2- and/or 3-position and/or E-M in the 5-position.

Some preferred embodiments of the compound of formula (I), as described above, are compounds of formula (Ia):

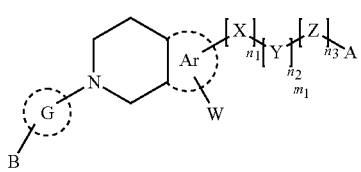

(Ia)

wherein Ar is 6-membered aryl, 5- or 6-membered heteroaryl or 5- or 6-membered cycloalkyl;
X is —O—, —S— or —C($R^{31}R^{32}$)—, Y is —O— or —C($R^{41}R^{42}$)—, Z is —C($R^{51}R^{52}$)—, and $n_1$, $n_2$ and $n_3$ are independently selected from 0 or 1 with the proviso that at least one of $n_1$, $n_2$ and $n_3$ must be 1 and at least one of X, Y or Z must be —C($R^{31}R^{32}$)—, —C($R^{41}R^{42}$)—, or —C($R^{51}R^{52}$)— respectively.

when X and Y are —C($R^{31}R^{32}$)— and —C($R^{41}R^{42}$)— respectively, $R^{31}$ and $R^{41}$ may be combined to form, together with X and Y, a ($C_3$-$C_6$)cycloalkyl ring which may be optionally substituted by ($C_1$-$C_3$)alkyl or halo;

when Y and Z are —C($R^{41}R^{42}$)— and —C($R^{51}R^{52}$)— respectively, $R^{41}$ and $R^{51}$ may be combined to form, together with Y and Z, a ($C_3$-$C_6$)cycloalkyl ring which may be optionally substituted by ($C_1$-$C_3$)alkyl or halo;

when X, Y and Z are —C($R^{31}R^{32}$)—, —C($R^{41}R^{42}$)— and —C($R^{51}R^{52}$)— respectively, $R^{31}$ and $R^{51}$ may form, together with X, Y and Z a ($C_4$-$C_7$)cycloalkyl ring which may be optionally substituted by ($C_1$-$C_3$)alkyl or halo;

A is —$CO_2H$, —$CO_2R^3$, —$CH_2OH$, tetrazolyl, 3-hydroxyisoxazol-5-yl or an acid bioisostere;

$R^3$ is ($C_1$-$C_6$)alkyl, or ($C_3$-$C_6$)cycloalkyl;

Ar is optionally substituted 1, 2 or 3 times by W, where W is ($C_1$-$C_{10}$)alkyl, ($C_2$-$C_{10}$)alkenyl, ($C_2$-$C_{10}$)alkynyl, ($C_1$-$C_{10}$)alkoxy, ($C_2$-$C_{10}$)dialkylamino, ($C_1$-$C_{10}$)alkylthio, ($C_2$-$C_{10}$)heteroalkyl, ($C_3$-$C_{10}$)cycloalkyl, ($C_3$-$C_{10}$)heterocycloalkyl, halo, ($C_1$-$C_{10}$)haloalkyl, ($C_1$-$C_{10}$)perhaloalkyl, optionally substituted aryl, optionally substituted heteroaryl, or optionally substituted arylalkyl, and when Ar is substituted by a plurality of substituents, each substituent is selected independently;

G is an optionally substituted 6- to 10-membered aryl, 5- to 10-membered heteroaryl or fused aryl or heteroaryl ring system;

G is optionally substituted one or more times by B, where B is ($C_1$-$C_{10}$)alkyl, ($C_2$-$C_{10}$)alkenyl, ($C_2$-$C_{10}$)alkynyl, ($C_1$-$C_{10}$)alkoxy, ($C_2$-$C_{10}$)dialkylamino, ($C_1$-$C_{10}$)alkylthio, ($C_2$-$C_{10}$)heteroalkyl, ($C_3$-$C_{10}$)cycloalkyl, ($C_3$-$C_{10}$)heterocycloalkyl, halo, ($C_1$-$C_{10}$)haloalkyl, ($C_1$-$C_{10}$)perhaloalkyl, optionally substituted aryl, optionally substituted heteroaryl, optionally substituted arylalkyl, cyano, or E-M where E is —O—, —S— or —N($R^4$)— and M is optionally substituted ($C_1$-$C_7$)alkyl, ($C_3$-$C_7$)cycloalkyl, fluoro($C_1$-$C_3$)alkyl a 5- to 10-membered heterocyclic group or an optionally substituted 6- to 10-membered aryl group, and when G is substituted by a plurality of substituents, each substituent is selected independently;

$R^1$, $R^{31}$, $R^{32}$, $R^{41}$, $R^{42}$, $R^{51}$, and $R^{52}$ are independently selected from hydrogen, deuterium, halo, or ($C_1$-$C_3$)alkyl optionally substituted by halo;

$R^4$ and $R^5$ are independently selected from hydrogen, deuterium, or ($C_1$-$C_3$)alkyl optionally substituted by halo;

or a pharmaceutically acceptable salt or solvate (eg hydrate) thereof, or corresponding N-oxide or prodrug (eg ester prodrug).

Particular embodiments of the compounds of formula (Ia) described above are set out below. It is to be understood that this invention covers all appropriate combinations of the substituents referred to herein, and that, where alternatives are provided for any one substituent, the invention covers all lists which may be formed by combinations of these alternatives.

In certain embodiments, Ar is 6-membered aryl or 5- or 6-membered heteroaryl. Ar may be phenyl, cyclohexyl, cyclopentyl, pyrrole, furan or thiophene. Ar may be phenyl, cyclohexyl or pyrrole. Ar may be phenyl.

In certain embodiments, $n_1$ is 0, Y is —C($R^{41}R^{42}$)— and Z is —C($R^{51}R^{52}$)—.

In certain embodiments, A is —$CO_2H$.

In certain embodiments X and Y are —C(R$^{31}$R$^{32}$)— and —C(R$^{41}$R$^{42}$)— respectively, and R$^{31}$ and R$^{41}$ are combined to form, together with X and Y, a cyclopropyl ring, for example

In certain embodiments X, Y and Z are —C(R$^{31}$R$^{32}$)—, —C(R$^{41}$R$^{42}$)— and —C(R$^{51}$R$^{52}$)— respectively, and R$^{31}$ and R$^{51}$ form, together with X, Y and Z a cyclobutyl ring, for example.

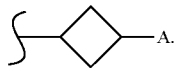

In certain embodiments, Ar is 6-membered aryl. X—Y—Z-A may then be connected to Ar in the 6- or 7-position. Ar may be substituted by W in the 5-, 6-, 7- or 8-position.

In certain embodiments, W is optionally substituted (C$_1$-C$_6$)alkyl, (C$_3$-C$_6$)cycloalkyl, halo or optionally substituted (C$_1$-C$_6$)alkoxy. W may be halo. W may be fluoro.

In certain embodiments, Ar is substituted 1, 2 or 3 times with W. Ar may be substituted 1 or 2 times by W.

In certain embodiments, G is an optionally substituted 6-membered aryl or 6-membered heteroaryl. G may be optionally substituted phenyl or pyridine.

In certain embodiments, B is (C$_1$-C$_6$)alkyl, (C$_2$-C$_{10}$)alkenyl, (C$_2$-C$_{10}$)alkynyl, (C$_1$-C$_{10}$)alkoxy, (C$_2$-C$_{10}$)dialkylamino, (C$_1$-C$_{10}$)alkylthio, (C$_2$-C$_{10}$)heteroalkyl, (C$_3$-C$_{10}$)cycloalkyl, (C$_3$-C$_{10}$)heterocycloalkyl, halo, (C$_1$-C$_{10}$)haloalkyl, (C$_1$-C$_{10}$)perhaloalkyl, optionally substituted aryl, optionally substituted heteroaryl, optionally substituted arylalkyl, cyano, or E-M- where E is —O—, —S— or —N(R$^4$)— and M is optionally substituted (C$_1$-C$_7$)alkyl, (C$_1$-C$_7$)cycloalkyl, fluoro(C$_1$-C$_3$)alkyl a 5- to 10-membered heterocyclic group or an optionally substituted 6- to 10-membered aryl group.

M may be substituted one or more times by K where K is (C$_1$-C$_6$)alkoxy, halo or N(R$^5$) and R$^5$ is hydrogen, deuterium, or (C$_1$-C$_3$)alkyl optionally substituted by halo.

When E is —O—, M may be (C$_3$-C$_7$)cycloalkyl, fluoro (C$_1$-C$_3$)alkyl or an optionally substituted 6- to 10-membered aryl group and preferably M is cyclobutyl, —CF$_3$ or phenyl.

B may be selected from halo, (C$_1$-C$_6$)alkyl optionally substituted with halo, (C$_3$-C$_6$)cycloalkyl optionally substituted with halo, (C$_1$-C$_6$)alkoxy optionally substituted with halo or E-M where E is —O—, —S— or —N(R$^4$)— and M is optionally substituted (C$_1$-C$_7$)alkyl, (C$_3$-C$_7$)cycloalkyl, fluoro(C$_1$-C$_3$)alkyl, a 5- to 10-membered heterocyclic group or an optionally substituted 6- to 10-membered aryl group. B may be halo or E-M where E is —O—, —S— or —N(R$^4$)— and M is optionally substituted (C$_1$-C$_7$)alkyl, (C$_3$-C$_7$)cycloalkyl, fluoro(C$_1$-C$_3$)alkyl, a 5- to 10-membered heterocyclic group or an optionally substituted 6- to 10-membered aryl group.

G may be substituted 1, 2, 3, 4 or 5 times with B. G may be substituted 2 or 3 times by B.

When G is substituted more than once with B, B may include E-M and/or halo.

If G is 6-membered aryl or 6-membered heteroaryl, G may be substituted twice by B in a 2,5- or 3,5-substitution pattern or three times by B in a 2,3,5-substitution pattern. G may be substituted by halo in the 2- and/or 3-position and/or E-M- in the 5-position.

Some further preferred embodiments of the compound of formula (I), as described above, are compounds of formula (Ib):

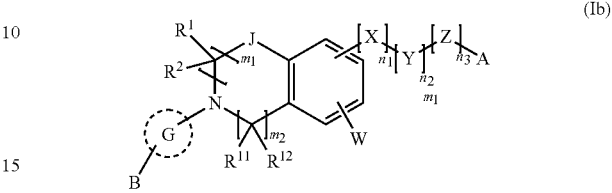

(Ib)

m$_1$ and m$_2$ are independently selected from 0, 1 or 2 with the proviso that m$_1$≠m$_2$ when m$_1$ or m$_2$=0 or when m$_1$ or m$_2$=2;
J is —C(R$^{21}$R$^{22}$)—, —O—, —N(R$^{21}$)— or —S— with the proviso that when J is —O—, —N(R$^{21}$)— or —S—, m$_1$ is 2;
X is —O—, —S— or —C(R$^{31}$R$^{32}$)—, Y is —O— or —C(R$^{41}$R$^{42}$)—, Z is —C(R$^{51}$R$^{52}$)—, and n$_1$, n$_2$ and n$_3$ are independently selected from 0 or 1 with the proviso that at least one of n$_1$, n$_2$ and n$_3$ must be 1 and at least one of X, Y or Z must be —C(R$^{31}$R$^{32}$)—, —C(R$^{41}$R$^{42}$)—, or —C(R$^{51}$R$^{52}$)—
when X and Y are —C(R$^{31}$R$^{32}$)— and —C(R$^{41}$R$^{42}$)— respectively, R$^{31}$ and R$^{41}$ may be combined to form, together with X and Y, a (C$_3$-C$_6$)cycloalkyl ring which may be optionally substituted by (C$_1$-C$_3$)alkyl or halo;
when Y and Z are —C(R$^{41}$R$^{42}$)— and —C(R$^{51}$R$^{52}$)— respectively, R$^{41}$ and R$^{51}$ may be combined to form, together with Y and Z, a (C$_3$-C$_6$)cycloalkyl ring which may be optionally substituted by (C$_1$-C$_3$)alkyl or halo;
when X, Y and Z are —C(R$^{31}$R$^{32}$)—, —C(R$^{41}$R$^{42}$)— and —C(R$^{51}$R$^{52}$)— respectively, R$^{31}$ and R$^{51}$ may form, together with X, Y and Z a (C$_4$-C$_7$)cycloalkyl ring which may be optionally substituted by (C$_1$-C$_3$)alkyl or halo;
R$^1$, R$^2$, R$^{11}$, R$^{12}$, R$^{21}$, R$^{22}$, R$^{31}$, R$^{32}$, R$^{41}$, R$^{42}$, R$^{51}$, and R$^{52}$ are independently selected from hydrogen, deuterium, halo, or (C$_1$-C$_3$)alkyl optionally substituted by halo;
A is —CO$_2$H, —CO$_2$R$^3$, —CH$_2$OH, tetrazolyl, 3-hydroxyisoxazol-5-yl or an acid bioisostere;
R$^3$ is (C$_1$-C$_6$)alkyl, or (C$_3$-C$_6$)cycloalkyl;
the phenyl ring is optionally substituted between one and three times by W where W is (C$_1$-C$_{10}$)alkyl, (C$_2$-C$_{10}$)alkenyl, (C$_2$-C$_{10}$)alkynyl, (C$_1$-C$_{10}$)alkoxy, (C$_2$-C$_{10}$)dialkylamino, (C$_1$-C$_{10}$)alkylthio, (C$_2$-C$_{10}$)heteroalkyl, (C$_3$-C$_{10}$)cycloalkyl, (C$_3$-C$_{10}$)heterocycloalkyl, halo, (C$_1$-C$_{10}$)haloalkyl, (C$_1$-C$_{10}$)perhaloalkyl, optionally substituted aryl, optionally substituted heteroaryl, or optionally substituted arylalkyl and where when the phenyl ring is substituted by a plurality of substituents, each substituent is selected independently;
G is an optionally substituted 6- to 10-membered aryl, 5- to 10-membered heteroaryl or fused aryl or heteroaryl ring system;
G is optionally substituted one or more times by B, where B is (C$_1$-C$_{10}$)alkyl, (C$_2$-C$_{10}$)alkenyl, (C$_2$-C$_{10}$)alkynyl, (C$_1$-C$_{10}$)alkoxy, (C$_2$-C$_{10}$)dialkylamino, (C$_1$-C$_{10}$)alkylthio, (C$_2$-C$_{10}$)heteroalkyl, (C$_3$-C$_{10}$)cycloalkyl, (C$_3$-C$_{10}$)heterocycloalkyl, halo, (C$_1$-C$_{10}$)haloalkyl, (C$_1$-C$_{10}$)perhaloalkyl, optionally substituted aryl, optionally substituted heteroaryl, optionally substituted arylalkyl, cyano, or E-M where E is —O—, —S— or —N(R$^4$)— and M is optionally substituted (C$_1$-C$_7$)alkyl, (C$_3$-C$_7$)cycloalkyl, fluoro(C$_1$-C$_3$)alkyl, a 5- to 10-membered heterocyclic group or an optionally substituted 6- to 10-membered aryl group, and when G is substituted by a plurality of substituents, each substituent is selected independently;

$R^4$ is hydrogen, deuterium, or $(C_1-C_3)$alkyl optionally substituted by halo;

or a pharmaceutically acceptable salt or solvate (eg hydrate) thereof, or corresponding N-oxide or prodrug (eg ester prodrug).

Particular embodiments of the compounds of formula (Ib) described above are set out below. It is to be understood that this invention covers all appropriate combinations of the substituents referred to herein, and that, where alternatives are provided for any one substituent, the invention covers all lists which may be formed by combinations of these alternatives.

In certain embodiments, $m_1$ and $m_2$ are chosen such that $m_1+m_2=2$, ie $m_1=m_2=1$, or $m_1=2$ and $m_2=0$, or $m_1=0$ and $m_2=2$.

In certain embodiments, $m_1$ and $m_2$ are 1.

In certain embodiments, $m_1$ and $m_2$ are 1 and J is —C($R^{21}R^{22}$)—.

In certain embodiments, $n_1$ is 0, Y is —C($R^{41}R^{42}$)— and Z is —C($R^{51}R^{52}$)—.

In certain embodiments, A is —CO$_2$H.

In certain embodiments X and Y are —C($R^{31}R^{32}$)— and —C($R^{41}R^{42}$)— respectively, and $R^{31}$ and $R^{41}$ are combined to form, together with X and Y, a cyclopropyl ring, for example

In certain embodiments X, Y and Z are —C($R^{31}R^{32}$)—, —C($R^{41}R^{42}$)— and —C($R^{51}R^{52}$)— respectively, and $R^{31}$ and $R^{51}$ form, together with X, Y and Z a cyclobutyl ring, for example.

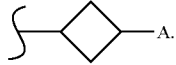

In certain embodiments, $m_1$ and $m_2$ are chosen such that $m_1+m_2=2$. X—Y—Z—A may then be connected to the phenyl ring in the 6- or 7-position. The phenyl ring may be substituted by W in the 5-, 6-, 7- or 8-position.

In certain embodiments, W is optionally substituted $(C_1-C_6)$alkyl, $(C_3-C_6)$cycloalkyl, halo or optionally substituted $(C_1-C_6)$alkoxy. W may be halo. W may be fluoro.

In certain embodiments the phenyl ring is substituted 1, 2 or 3 times with W. The phenyl ring may be substituted 1 or 2 times by W.

In certain embodiments, G is an optionally substituted 6 membered aryl or 6-membered heteroaryl. G may be optionally substituted phenyl or pyridine.

In certain embodiments, B is $(C_1-C_6)$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, optionally substituted arylalkyl, cyano, or E-M where E is —O—, —S— or —N($R^4$)— and M is optionally substituted $(C_1-C_7)$alkyl, $(C_3-C_7)$cycloalkyl, fluoro$(C_1-C_3)$alkyl, a 5- to 10-membered heterocyclic group or an optionally substituted 6- to 10-membered aryl group.

M may be substituted one or more times by K where K is $C_1-C_6$ alkoxy, halo or —N($R^5$) and $R^5$ is hydrogen, deuterium, or $(C_1-C_3)$alkyl optionally substituted by halo.

When E is —O—, M may be $(C_3-C_7)$cycloalkyl, fluoro$(C_1-C_3)$alkyl or an optionally substituted 6- to 10-membered aryl group and preferably M is cyclobutyl, —CF$_3$ or phenyl.

B may be selected from halo, $(C_1-C_6)$alkyl optionally substituted with halo, $(C_3-C_6)$cycloalkyl optionally substituted with halo, $(C_1-C_6)$alkoxy optionally substituted with halo or E-M where E is —O—, —S— or —N($R^4$)— and M is optionally substituted $(C_1-C_7)$alkyl, $(C_3-C_7)$cycloalkyl, a 5- to 10-membered heterocyclic group or a 6- to 10-membered aryl group. B may be halo or E-M where E is —O—, —S— or —N($R^4$)— and M is optionally substituted $(C_1-C_7)$alkyl, $(C_3-C_7)$cycloalkyl, fluoro$(C_1-C_3)$alkyl, a 5- to 10-membered heterocyclic group or an optionally substituted 6- to 10-membered aryl group.

G may be substituted 1, 2, 3, 4 or 5 times with B. G may be substituted 2 or 3 times by B.

When G is substituted more than once with B, B may include E-M and halo.

If G is 6-membered aryl or 6-membered heteroaryl, G may be substituted twice by B in a 2,5- or 3,5-substitution pattern or three times by B in a 2,3,5-substitution pattern. G may be substituted by halo in the 2- and/or 3-position and/or E-M- in the 5-position.

Some further preferred embodiments of the compound of formula (I), as described above, are compounds of formula (Ic):

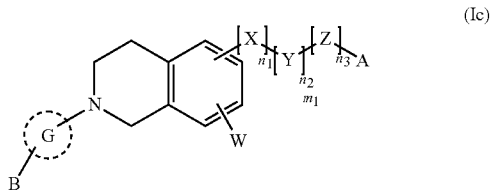

X is —O—, —S— or —C($R^{31}R^{32}$)—, Y is —O— or —C($R^{41}R^{42}$)—, Z is —C($R^{51}R^{52}$)—, and $n_1$, $n_2$ and $n_3$ are independently selected from 0 or 1 with the proviso that at least one of $n_1$, $n_2$ and $n_3$ must be 1 and at least one of X, Y or Z must be —C($R^{31}R^{32}$)—, —C($R^{41}R^{42}$)—, or —C($R^{51}R^{52}$)— respectively;

when X and Y are —C($R^{31}R^{32}$)— and —C($R^{41}R^{42}$)— respectively, $R^{31}$ and $R^{41}$ may be combined to form, together with X and Y, a $(C_3-C_6)$cycloalkyl ring which may be optionally substituted by $(C_1-C_3)$alkyl or halo;

when Y and Z are —C($R^{41}R^{42}$)— and —C($R^{51}R^{52}$)— respectively, $R^{41}$ and $R^{51}$ may be combined to form, together with Y and Z, a $(C_3-C_6)$cycloalkyl ring which may be optionally substituted by $(C_1-C_3)$alkyl or halo;

when X, Y and Z are —C($R^{31}R^{32}$)—, —C($R^{41}R^{42}$)— and —C($R^{51}R^{52}$)— respectively, $R^{31}$ and $R^{51}$ may form, together with X, Y and Z a $(C_4-C_7)$cycloalkyl ring which may be optionally substituted by $(C_1-C_3)$alkyl or halo;

$R^{31}$, $R^{32}$, $R^{41}$, $R^{42}$, $R^{51}$, and $R^{52}$ are independently selected from hydrogen, deuterium, halo, or $(C_1-C_3)$alkyl optionally substituted by halo;

A is —$CO_2H$, —$CO_2R^3$, —$CH_2OH$, tetrazolyl, 3-hydroxy-isoxazol-5-yl or an acid bioisostere;

$R^3$ is ($C_1$-$C_6$)alkyl, or ($C_3$-$C_6$)cycloalkyl;

the phenyl ring is optionally substituted 1, 2 or 3 times by W where W is ($C_1$-$C_{10}$)alkyl, ($C_2$-$C_{10}$)alkenyl, ($C_2$-$C_{10}$)alkynyl, ($C_1$-$C_{10}$)alkoxy, ($C_2$-$C_{10}$)dialkylamino, ($C_1$-$C_{10}$)alkylthio, ($C_2$-$C_{10}$)heteroalkyl, ($C_3$-$C_{10}$)cycloalkyl, ($C_3$-$C_{10}$)heterocycloalkyl, halo, ($C_1$-$C_{10}$)haloalkyl, ($C_1$-$C_{10}$)perhaloalkyl, optionally substituted aryl, optionally substituted heteroaryl, or optionally substituted arylalkyl and where when the phenyl ring is substituted by a plurality of substituents, each substituent is selected independently;

G is an optionally substituted 6- to 10-membered aryl, 5- to 10-membered heteroaryl or fused aryl or heteroaryl ring system;

G is optionally substituted one or more times by B where B is ($C_1$-$C_{10}$)alkyl, ($C_2$-$C_{10}$)alkenyl, ($C_2$-$C_{10}$)alkynyl, ($C_1$-$C_{10}$)alkoxy, ($C_2$-$C_{10}$)dialkylamino, ($C_1$-$C_{10}$)alkylthio, ($C_2$-$C_{10}$)heteroalkyl, ($C_3$-$C_{10}$)cycloalkyl, ($C_3$-$C_{10}$)heterocycloalkyl, halo, ($C_1$-$C_{10}$)haloalkyl, ($C_1$-$C_{10}$)perhaloalkyl, optionally substituted aryl, optionally substituted heteroaryl, optionally substituted arylalkyl, cyano, or E-M where E is —O—, —S— or —N($R^4$)— and M is optionally substituted ($C_1$-$C_7$)alkyl, ($C_3$-$C_7$)cycloalkyl, fluoro($C_1$-$C_3$)alkyl, a 5- to 10-membered heterocyclic group or an optionally substituted 6- to 10-membered aryl group, and where when G is substituted by a plurality of substituents, each substituent is selected independently;

$R^4$ is hydrogen, deuterium, or ($C_1$-$C_3$)alkyl optionally substituted by halo;

or a pharmaceutically acceptable salt or solvate (eg hydrate) thereof, or corresponding N-oxide or prodrug (eg ester prodrug).

Particular embodiments of the compounds of formula (Ic) described above are set out below. It is to be understood that this invention covers all appropriate combinations of the substituents referred to herein, and that, where alternatives are provided for any one substituent, the invention covers all lists which may be formed by combinations of these alternatives.

In certain embodiments, $n_1$ is 0, Y is —C($R^{41}R^{42}$)— and Z is —C($R^{51}R^{52}$)—.

In certain embodiments, A is —$CO_2H$.

In certain embodiments X and Y are —C($R^{31}R^{32}$)— and —C($R^{41}R^{42}$)— respectively, and $R^{31}$ and $R^{41}$ are combined to form, together with X and Y, a cyclopropyl ring, for example

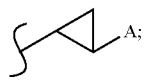

In certain embodiments X, Y and Z are —C($R^{31}R^{32}$)—, —C($R^{41}R^{42}$)— and —C($R^{51}R^{52}$)— respectively, and $R^{31}$ and $R^{51}$ form, together with X, Y and Z a cyclobutyl ring, for example

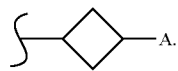

X—Y—Z-A may be connected to the phenyl ring in the 6- or 7-position. The phenyl ring may be substituted by W in the 5-, 6-, 7- or 8-position.

In certain embodiments, W is optionally substituted ($C_1$-$C_6$)alkyl, ($C_3$-$C_6$)cycloalkyl, halo or optionally substituted ($C_1$-$C_6$)alkoxy. W may be halo. W may be fluoro.

In certain embodiments the phenyl ring is substituted 1, 2 or 3 times with W. The phenyl ring may be substituted 1 or 2 times by W.

In certain embodiments the phenyl ring is not substituted by W.

In certain embodiments, G is an optionally substituted 6 membered aryl or 6 membered heteroaryl. G may be optionally substituted phenyl or pyridine.

In certain embodiments, B is ($C_1$-$C_6$)alkyl, ($C_2$-$C_{10}$)alkenyl, ($C_2$-$C_{10}$)alkynyl, ($C_1$-$C_{10}$)alkoxy, ($C_2$-$C_{10}$)dialkylamino, ($C_1$-$C_{10}$)alkylthio, ($C_2$-$C_{10}$)heteroalkyl, ($C_3$-$C_{10}$)cycloalkyl, ($C_3$-$C_{10}$)heterocycloalkyl, halo, ($C_1$-$C_{10}$)haloalkyl, ($C_1$-$C_{10}$)perhaloalkyl, optionally substituted aryl, optionally substituted heteroaryl, optionally substituted arylalkyl, cyano, or E-M where E is —O—, —S— or —N($R^4$)— and M is optionally substituted ($C_1$-$C_7$)alkyl, ($C_3$-$C_7$)cycloalkyl, fluoro($C_1$-$C_3$)alkyl, a 5- to 10-membered heterocyclic group or an optionally substituted 6- to 10-membered aryl group.

M may be substituted one or more times by K where K is $C_1$-$C_6$ alkoxy, halo or —N($R^5$) where $R^5$ is hydrogen, deuterium, or ($C_1$-$C_3$)alkyl optionally substituted by halo.

When E is —O—, M may be ($C_3$-$C_7$)cycloalkyl, fluoro($C_1$-$C_3$)alkyl, or an optionally substituted 6- to 10-membered aryl group and preferably M is cyclobutyl, —$CF_3$ or phenyl optionally substituted by halo and/or ($C_1$-$C_3$)alkyl.

B may be selected from the group consisting of halo, $C_1$-$C_6$ alkyl optionally substituted with halo, ($C_3$-$C_6$)cycloalkyl optionally substituted with halo, O—($C_1$-$C_6$)alkyl optionally substituted with halo and E-M where E is —O—, —S— or —N($R^4$)— and M is optionally substituted ($C_1$-$C_7$)alkyl, ($C_3$-$C_7$)cycloalkyl, fluoro($C_1$-$C_3$)alkyl, a 5- to 10-membered heterocyclic group or an optionally substituted 6- to 10-membered aryl group. B may be halo or E-M where E is —O—, —S— or —N($R^4$)— and M is optionally substituted ($C_1$-$C_7$)alkyl, ($C_3$-$C_7$)cycloalkyl, fluoro($C_1$-$C_3$) alkyl, a 5- to 10-membered heterocyclic group or an optionally substituted 6- to 10-membered aryl group.

G may be substituted 1, 2, 3, 4 or 5 times with B. G may be substituted 1, 2 or 3 times by B.

When G is substituted more than once with B, B may comprise E-M and/or halo.

If G is 6-membered aryl or 6-membered heteroaryl, G may be substituted twice by B in a 2,5- or 3,5-substitution pattern or three times by B in a 2,3,5-substitution pattern. G may be substituted by halo in the 2- and/or 3-position and/or E-M- in the 5-position.

The inventors have found that many GPR120 agonists according to the present invention have lower potency in mouse GPR120 compared with their human GPR120 potency. However, compounds of the present invention in which G is aryl substituted by phenoxy have roughly equivalent potency against both mouse and human GPR120. This crossover allows these compounds to be tested in mouse disease models at similar concentrations to those expected in human, and thus more accurately validate the effects of a GPR120 agonist in mouse models of disease, without overdosing. Importantly, retaining high potency against the mouse GPR120 receptor also allows the safety toxicology testing in mouse to evaluate any target-related toxicity, that might otherwise be missed in compounds with reduced mouse GPR120 potency, before proceeding to human testing.

Thus, in some preferred compounds of formula (Ic) G is phenyl substituted 1 or 2 times with B, wherein B is halo and/or E-M where E is —O— and M is an optionally substituted 6- to 10-membered aryl group.

When M is a substituted 6- to 10-membered aryl group, it may be substituted by halo and/or $(C_1-C_3)$alkyl.

When G is substituted once with B, B may be E-M where E is —O— and M is an optionally substituted 6- to 10-membered aryl group. B may be phenoxy (optionally substituted by halo and/or $(C_1-C_3)$alkyl).

When G is substituted 2 times with B, B may be E-M, where E is —O— and M is an optionally substituted 6- to 10-membered aryl group, and halo. When G is substituted 2 times with B, B may be phenoxy (optionally substituted by halo and/or $(C_1-C_3)$alkyl) and halo. B may be phenoxy (optionally substituted by halo and/or $(C_1-C_3)$alkyl) and fluoro.

B may be phenyl substituted by fluoro in the 2-position and phenoxy in the 5-position.

In particular embodiments, X—Y—Z-A may be —CH$_2$—CH$_2$—COOH or

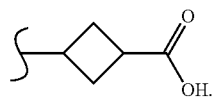

In particular embodiments, the phenyl ring is not substituted by W or is substituted once with W, wherein W is halo. W may be fluoro.

In the course of investigating the tetrahydroisoquinolines compounds of formula (Ic), it was found that the tetrahydroisoquinoline compounds may contain small amounts of the oxidised dihydroquinoline iminium salts as impurities. The iminium salt is likely produced by air oxidation catalysed by light or trace metals, and may be stabilised by conjugation to both flanking aromatic rings. Examination of the literature showed several reports of N-aryl tetrahydroisoquinoline oxidation and use of the resulting iminium salts as synthetic intermediates due to their inherent reactivity (Liu Y, et al, Chemistry 2017, 2; 23(13):3062-3066; Guo-Qiang Xu, et al, Chem Commun (Camb) 2016, 21; 52(6):1190-1193; Junjie Cai, et al, Phosphorus, Sulfur Silicon Relat. Elem. 2017, 192(9), 1068-1073; and Yong Zhang, et al, RSC Adv. 2017, 7, 1229-123). Production of reactive iminium salts, either by air oxidation or by oxidative metabolism, is highly disadvantageous since this possible reactivity is known to lead to idiosyncratic toxicity (Antonia F. Stepan, et al, Res. Toxicol. 2011, 24, 1345-1410). Tetrahydro-3H-benzazepines have an extra CH$_2$ group inserted between the N-atom and the aromatic ring, compared to tetrahydroisoquinolines, which precludes any conjugation to the aromatic rings that stabilise the iminium salt. Tetrahydro-3H-benzazepines have been found to be quite stable towards arial oxidation, and surprisingly to retain excellent agonism against GPR120, thus providing GPR120 agonists without associated risk of reactivity that could give rise to toxicity.

Thus, some preferred embodiments of the compounds of formula (I), as described above, are those in which $m_1$ is 1 and $m_2$ is 2, and compounds of formula (I) wherein $m_1$ is 2 and $m_2$ is 1.

In some preferred embodiments, J is —C(R$^{21}$R$^{22}$)— and R$^1$, R$^2$, R$^{11}$, R$^{12}$, R$^{21}$ and R$^{22}$ are hydrogen.

In some preferred embodiments, Ar is 6-membered aryl.

Thus, some further preferred embodiments of the compound of formula (I), as described above, are tetrahydrobenzazepine compounds of formula (Id):

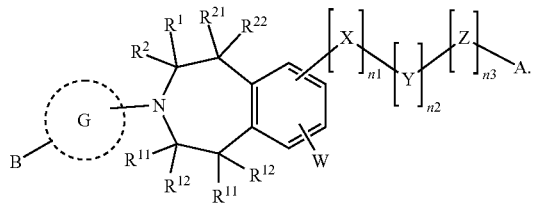

$R^1$, $R^2$, $R^{11}$, $R^{12}$, $R^{21}$ and $R^{22}$ are independently selected from hydrogen and $(C_1-C_3)$alkyl;

X is —O—, —S— or —C(R$^{31}$R$^{32}$)—, Y is —O— or —C(R$^{41}$R$^{42}$)—, Z is —C(R$^{51}$R$^{52}$)—, and $n_1$, $n_2$ and $n_3$ are independently selected from 0 or 1 with the proviso that at least one of $n_1$, $n_2$ and $n_3$ must be 1 and at least one of X, Y or Z must be —C(R$^{31}$R$^{32}$)—, —C(R$^{41}$R$^{42}$)—, or —C(R$^{51}$R$^{52}$)— respectively;

when X and Y are —C(R$^{31}$R$^{32}$)— and —C(R$^{41}$R$^{42}$)— respectively, R$^{31}$ and R$^{41}$ may be combined to form, together with X and Y, a $(C_3-C_6)$cycloalkyl ring which may be optionally substituted by $(C_1-C_3)$alkyl or halo;

when Y and Z are —C(R$^{41}$R$^{42}$)— and —C(R$^{51}$R$^{52}$)— respectively, R$^{41}$ and R$^{51}$ may be combined to form, together with Y and Z, a $(C_3-C_6)$cycloalkyl ring which may be optionally substituted by $(C_1-C_3)$alkyl or halo;

when X, Y and Z are —C(R$^{31}$R$^{32}$)—, —C(R$^{41}$R$^{42}$)— and —C(R$^{51}$R$^{52}$)— respectively, R$^{31}$ and R$^{51}$ may form, together with X, Y and Z a $(C_4-C_7)$cycloalkyl ring which may be optionally substituted by $(C_1-C_3)$alkyl or halo;

R$^{31}$, R$^{32}$, R$^{41}$, R$^{42}$, R$^{51}$, and R$^{52}$ are independently selected from hydrogen, deuterium, halo, or $(C_1-C_3)$alkyl optionally substituted by halo;

A is —CO$_2$H, —CO$_2$R$^3$, —CH$_2$OH, tetrazolyl, 3-hydroxyisoxazol-5-yl or an acid bioisostere;

R$^3$ is $(C_1-C_6)$alkyl, or $(C_3-C_6)$cycloalkyl;

the phenyl ring is optionally substituted 1, 2 or 3 times by W where W is $(C_1-C_{10})$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, or optionally substituted arylalkyl and where when the phenyl ring is substituted by a plurality of substituents, each substituent is selected independently;

G is an optionally substituted 6- to 10-membered aryl, 5- to 10-membered heteroaryl or fused aryl or heteroaryl ring system;

G is optionally substituted one or more times by B where B is $(C_1-C_{10})$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, optionally substituted arylalkyl, cyano, or E-M where E is —O—, —S— or —N(R$^4$)— and M is optionally substituted $(C_1-C_7)$alkyl, $(C_3-C_7)$cycloalkyl, fluoro$(C_1-C_3)$alkyl, a 5- to 10-membered heterocyclic group or an optionally substituted 6- to 10-membered aryl group, and where when G is substituted by a plurality of substituents, each substituent is selected independently;

R$^4$ is hydrogen, deuterium, or $(C_1-C_3)$alkyl optionally substituted by halo;

or a pharmaceutically acceptable salt or solvate (eg hydrate) thereof, or corresponding N-oxide or prodrug (eg ester prodrug).

Particular embodiments of the compounds of formula (Id) described above are set out below. It is to be understood that this invention covers all appropriate combinations of the substituents referred to herein, and that, where alternatives are provided for any one substituent, the invention covers all lists which may be formed by combinations of these alternatives.

In certain embodiments, $R^1$, $R^2$, $R^{11}$, $R^{12}$, $R^{21}$ and $R^{22}$ are hydrogen.

In certain embodiments, $n_1$ is 0, Y is —$C(R^{41}R^{42})$— and Z is —$C(R^{51}R^{52})$—.

In certain embodiments, A is —$CO_2H$.

In certain embodiments X and Y are —$C(R^{31}R^{32})$— and —$C(R^{41}R^{42})$— respectively, and $R^{31}$ and $R^{41}$ are combined to form, together with X and Y, a cyclopropyl ring, for example

In certain embodiments X, Y and Z are —$C(R^{31}R^{32})$—, —$C(R^{41}R^{42})$— and —$C(R^{51}R^{52})$— respectively, and $R^{31}$ and $R^{51}$ form, together with X, Y and Z a cyclobutyl ring, for example

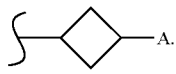

X—Y—Z-A may be connected to the phenyl ring in the 2- or 3-position. The phenyl ring may be substituted by W in the 1-, 2-, 3- or 4-position.

In certain embodiments, W is optionally substituted ($C_1$-$C_6$)alkyl, ($C_3$-$C_6$)cycloalkyl, halo or optionally substituted ($C_1$-$C_6$)alkoxy. W may be halo. W may be fluoro.

In certain embodiments the phenyl ring is substituted 1, 2 or 3 times with W. The phenyl ring may be substituted 1 or 2 times by W.

In certain embodiments, the phenyl ring is not substituted by W.

In certain embodiments, G is an optionally substituted 6 membered aryl or 6 membered heteroaryl. G may be optionally substituted phenyl or pyridine.

In certain embodiments, B is ($C_1$-$C_6$)alkyl, ($C_2$-$C_{10}$)alkenyl, ($C_2$-$C_{10}$)alkynyl, ($C_1$-$C_{10}$)alkoxy, ($C_2$-$C_{10}$)dialkylamino, ($C_1$-$C_{10}$)alkylthio, ($C_2$-$C_{10}$)heteroalkyl, ($C_3$-$C_{10}$)cycloalkyl, ($C_3$-$C_{10}$)heterocycloalkyl, halo, ($C_1$-$C_{10}$)haloalkyl, ($C_1$-$C_{10}$)perhaloalkyl, optionally substituted aryl, optionally substituted heteroaryl, optionally substituted arylalkyl, cyano, or E-M where E is —O—, —S— or —N($R^4$)— and M is optionally substituted ($C_1$-$C_7$)alkyl, ($C_3$-$C_7$)cycloalkyl, fluoro($C_1$-$C_3$)alkyl, a 5- to 10-membered heterocyclic group or an optionally substituted 6- to 10-membered aryl group.

M may be substituted one or more times by K where K is $C_1$-$C_6$ alkoxy, halo or —N($R^5$) where $R^5$ is hydrogen, deuterium, or ($C_1$-$C_3$)alkyl optionally substituted by halo.

When E is —O—, M may be ($C_3$-$C_7$)cycloalkyl, fluoro($C_1$-$C_3$)alkyl or an optionally substituted 6- to 10-membered aryl group and preferably M is cyclobutyl, —$CF_3$ or phenyl optionally substituted by halo and/or ($C_1$-$C_3$)alkyl.

B may be selected from halo, $C_1$-$C_6$ alkyl optionally substituted with halo, ($C_3$-$C_6$)cycloalkyl optionally substituted with halo, O—($C_1$-$C_6$)alkyl optionally substituted with halo or E-M where E is —O—, —S— or —N($R^4$)— and M is optionally substituted ($C_1$-$C_7$)alkyl, ($C_3$-$C_7$)cycloalkyl, a 5- to 10-membered heterocyclic group or a 6- to 10-membered aryl group. B may be halo or E-M where E is —O—, —S— or —N($R^4$)— and M is optionally substituted ($C_1$-$C_7$)alkyl, ($C_3$-$C_7$)cycloalkyl, fluoro($C_1$-$C_3$)alkyl, a 5- to 10-membered heterocyclic group or an optionally substituted 6- to 10-membered aryl group.

G may be substituted 1, 2, 3, 4 or 5 times with B. G may be substituted 1, 2 or 3 times by B.

When G is substituted more than once with B, B may comprise E-M and/or halo.

If G is 6-membered aryl or 6-membered heteroaryl, G may be substituted twice by B in a 2,5- or 3,5-substitution pattern or three times by B in a 2,3,5-substitution pattern. G may be substituted by halo in the 2- and/or 3-position and/or E-M- in the 5-position.

In certain preferred embodiments, G is phenyl substituted 1 or 2 times by B, wherein B is selected from halo and E-M, where E is —O— and M is optionally substituted ($C_1$-$C_7$) alkyl, ($C_3$-$C_7$)cycloalkyl, fluoro($C_1$-$C_3$)alkyl or an optionally substituted 6- to 10-membered aryl group.

B may be selected from fluoro, phenoxy, —$OCF_3$, —O—$CH(CH_3)_2$,

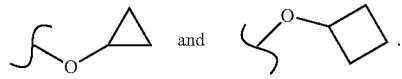

When G is substituted 2 times with B, B may be halo and E-M.

In certain embodiments, G is phenyl substituted by halo in the 2- or 3-position and E-M in the 5-position. In certain embodiments, G is phenyl substituted by fluoro in the 2- or 3-position and E-M in the 5-position where E-M is selected from the group consisting of phenoxy, —$OCF_3$, —$CH(CH_3)_2$,

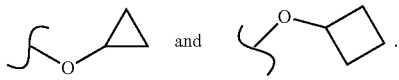

In some preferred compounds of formula (Id), $R^1$, $R^2$, $R^{11}$, $R^{12}$, $R^{21}$ and $R^{22}$ are hydrogen; X—Y—Z-A is —$CH_2$—$CH_2$—COOH, —$CH_2CH(CH_3)$COOH or

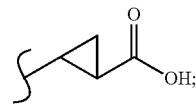

G is phenyl substituted 1 or 2 times by B wherein B is halo, for instance fluoro, and/or E-M where E-M is selected from the group consisting of phenoxy, —$OCF_3$, —O—CH$(CH_3)_2$,

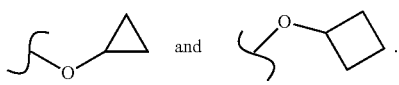

As discussed above, compounds containing a phenoxyaryl substituent have roughly equivalent potency in mouse and human GPR120. Thus, in certain preferred compounds of formula (Id), G is phenyl substituted at least once with an optionally substituted 6- to 10-membered aryl group. G may be phenyl substituted at least once with phenoxy. G may also be substituted by halo. In certain embodiments, G may be phenyl substituted once with B where B is phenoxy, or phenyl substituted 2 times with B, where B is halo and phenoxy. B may be fluoro and phenoxy.

Some further preferred embodiments of the compound of formula (I), as described above, are compounds of formula (Ie):

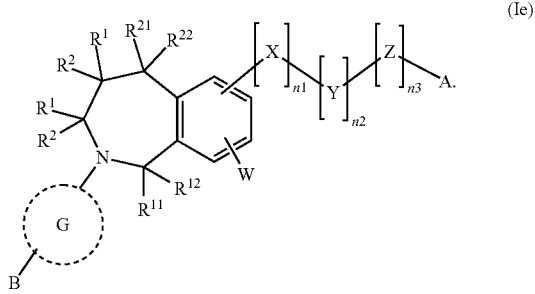

(Ie)

$R^1$, $R^2$, $R^{11}$, $R^{12}$, $R^{21}$ and $R^{22}$ are independently selected from hydrogen and $(C_1-C_3)$alkyl;

X is —O—, —S— or —C($R^{31}R^{32}$)—, Y is —O— or —C($R^{41}R^{42}$)—, Z is —C($R^{51}R^{52}$)—, and $n_1$, $n_2$ and $n_3$ are independently selected from 0 or 1 with the proviso that at least one of $n_1$, $n_2$ and $n_3$ must be 1 and at least one of X, Y or Z must be —C($R^{31}R^{32}$)—, —C($R^{41}R^{42}$)—, or —C($R^{51}R^{52}$)— respectively;

when X and Y are —C($R^{31}R^{32}$)— and —C($R^{41}R^{42}$)— respectively, $R^{31}$ and $R^{41}$ may be combined to form, together with X and Y, a $(C_3-C_7)$cycloalkyl ring which may be optionally substituted by $(C_1-C_3)$alkyl or halo;

when Y and Z are —C($R^{41}R^{42}$)— and —C($R^{51}R^{52}$)— respectively, $R^{41}$ and $R^{51}$ may be combined to form, together with Y and Z, a $(C_3-C_6)$cycloalkyl ring which may be optionally substituted by $(C_1-C_3)$alkyl or halo;

when X, Y and Z are —C($R^{31}R^{32}$)—, —C($R^{41}R^{42}$)— and —C($R^{51}R^{52}$)— respectively, $R^{31}$ and $R^{51}$ may form, together with X, Y and Z a $(C_4-C_7)$cycloalkyl ring which may be optionally substituted by $(C_1-C_3)$alkyl or halo;

$R^{31}$, $R^{32}$, $R^{41}$, $R^{42}$, $R^{51}$, and $R^{52}$ are independently selected from hydrogen, deuterium, halo, or $(C_1-C_3)$alkyl optionally substituted by halo;

A is —$CO_2H$, —$CO_2R^3$, —$CH_2OH$, tetrazolyl, 3-hydroxy-isoxazol-5-yl or an acid bioisostere;

$R^3$ is $(C_1-C_6)$alkyl, or $(C_3-C_6)$cycloalkyl;

the phenyl ring is optionally substituted 1, 2 or 3 times by W where W is $(C_1-C_{10})$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, or optionally substituted arylalkyl and where when the phenyl ring is substituted by a plurality of substituents, each substituent is selected independently;

G is an optionally substituted 6- to 10-membered aryl, 5- to 10-membered heteroaryl or fused aryl or heteroaryl ring system;

G is optionally substituted one or more times by B where B is $(C_1-C_{10})$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, optionally substituted arylalkyl, cyano, or E-M where E is —O—, —S— or —N($R^4$)— and M is optionally substituted $(C_1-C_7)$alkyl, $(C_3-C_7)$cycloalkyl, fluoro$(C_1-C_3)$alkyl, a 5- to 10-membered heterocyclic group or an optionally substituted 6- to 10-membered aryl group, and where when G is substituted by a plurality of substituents, each substituent is selected independently;

$R^4$ is hydrogen, deuterium, or $(C_1-C_3)$alkyl optionally substituted by halo;

or a pharmaceutically acceptable salt or solvate (eg hydrate) thereof, or corresponding N-oxide or prodrug (eg ester prodrug).

Particular embodiments of the compounds of formula (Ie) described above are set out below. It is to be understood that this invention covers all appropriate combinations of the substituents referred to herein, and that, where alternatives are provided for any one substituent, the invention covers all lists which may be formed by combinations of these alternatives.

In certain embodiments, $R^1$, $R^2$, $R^{11}$, $R^{12}$, $R^{21}$ and $R^{22}$ hydrogen.

In certain embodiments, $n_1$ is 0, Y is —C($R^{41}R^{42}$)— and Z is —C($R^{51}R^{52}$)—.

In certain embodiments, A is —$CO_2H$.

In certain embodiments X and Y are —C($R^{31}R^{32}$)— and —C($R^{41}R^{42}$)— respectively, and $R^{31}$ and $R^{41}$ are combined to form, together with X and Y, a cyclopropyl ring, for example

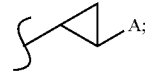

In certain embodiments X, Y and Z are —C($R^{31}R^{32}$)—, —C($R^{41}R^{42}$)— and —C($R^{51}R^{52}$)— respectively, and $R^{31}$ and $R^{51}$ form, together with X, Y and Z a cyclobutyl ring, for example

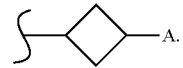

X—Y—Z-A may be connected to the phenyl ring in the 2- or 3-position. The phenyl ring may be substituted by W in the 1-, 2-, 3- or 4-position.

In certain embodiments, W is optionally substituted $(C_1-C_6)$alkyl, $(C_3-C_6)$cycloalkyl, halo or optionally substituted $(C_1-C_6)$alkoxy. W may be halo. W may be fluoro.

In certain embodiments the phenyl ring is substituted 1, 2 or 3 times with W. The phenyl ring may be substituted 1 or 2 times by W.

In certain embodiments, the phenyl ring is not substituted by W.

In certain embodiments, G is an optionally substituted 6 membered aryl or 6 membered heteroaryl. G may be optionally substituted phenyl or pyridine.

In certain embodiments, B is $(C_1-C_6)$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, optionally substituted arylalkyl, cyano, or E-M where E is —O—, —S— or —N(R$^4$)— and M is optionally substituted $(C_1-C_7)$alkyl, $(C_3-C_7)$cycloalkyl, fluoro$(C_1-C_3)$alkyl, a 5- to 10-membered heterocyclic group or an optionally substituted 6- to 10-membered aryl group.

M may be substituted one or more times by K where K is $C_1-C_6$ alkoxy, halo or —N(R$^5$) where R$^5$ is hydrogen, deuterium, or $(C_1-C_3)$alkyl optionally substituted by halo.

When E is —O—, M may be $(C_3-C_7)$cycloalkyl, fluoro$(C_1-C_3)$alkyl or an optionally substituted 6- to 10-membered aryl group and preferably M is cyclobutyl, —CF$_3$ or phenyl optionally substituted by halo and/or $(C_1-C_3)$alkyl.

B may be selected from halo, $C_1-C_6$ alkyl optionally substituted with halo, $(C_3-C_6)$cycloalkyl optionally substituted with halo, O—$(C_1-C_7)$alkyl optionally substituted with halo or E-M where E is —O—, —S— or —N(R$^4$)— and M is optionally substituted $(C_1-C_7)$alkyl, $(C_3-C_7)$cycloalkyl, a 5- to 10-membered heterocyclic group or a 6- to 10-membered aryl group. B may be halo or E-M where E is —O—, —S— or —N(R$^4$)— and M is optionally substituted $(C_1-C_7)$alkyl, $(C_3-C_7)$cycloalkyl, fluoro$(C_1-C_3)$alkyl, a 5- to 10-membered heterocyclic group or an optionally substituted 6- to 10-membered aryl group.

G may be substituted 1, 2, 3, 4 or 5 times with B. G may be substituted 1, 2 or 3 times by B.

When G is substituted more than once with B, B may comprise E-M and/or halo.

If G is 6-membered aryl or 6-membered heteroaryl, G may be substituted twice by B in a 2,5- or 3,5-substitution pattern or three times by B in a 2,3,5-substitution pattern. G may be substituted by halo in the 2- and/or 3-position and/or E-M- in the 5-position.

In certain preferred embodiments, G is phenyl substituted 1 or 2 times by B, wherein B is selected from halo and E-M, where E is —O— and M is optionally substituted $(C_1-C_7)$ alkyl, $(C_3-C_7)$cycloalkyl, fluoro$(C_1-C_3)$alkyl or an optionally substituted 6- to 10-membered aryl group.

B may be selected from fluoro, phenoxy, —OCF$_3$, —O—CH(CH$_3$)$_2$,

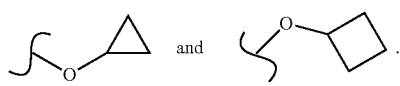

When G is substituted 2 times with B, B may be halo and E-M.

In certain embodiments, G is phenyl substituted by halo in the 2- or 3-position and E-M in the 5-position. In certain embodiments, G is phenyl substituted by fluoro in the 2- or 3-position and E-M in the 5-position where E-M is selected from the group consisting of phenoxy, —OCF$_3$, —O—CH(CH$_3$)$_2$,

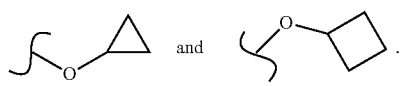

In some preferred compounds of formula (Ie), R$^1$, R$^2$, R$^{11}$, R$^{12}$, R$^{21}$ and R$^{22}$ are hydrogen; X—Y—Z-A is —CH$_2$—CH$_2$—COOH, —CH$_2$CH(CH$_3$)COOH or

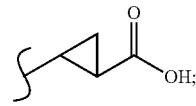

G is phenyl substituted 1 or 2 times by B wherein B is halo, for instance fluoro, and/or E-M where E-M is selected from the group consisting of phenoxy, —O—CF$_3$, —O—CH(CH$_3$)$_2$,

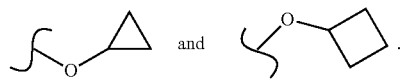

In certain embodiments, G is phenyl substituted by fluoro in the 2-position and —OCF$_3$ in the 5-position.

Particular compounds of the invention are:

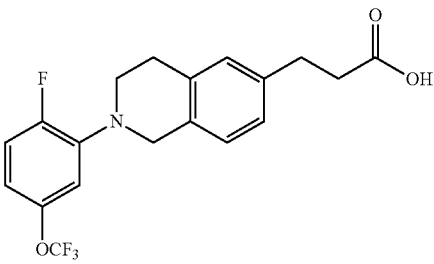

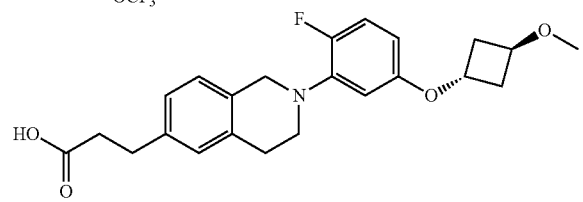

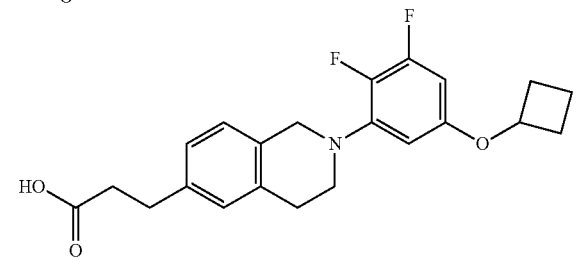

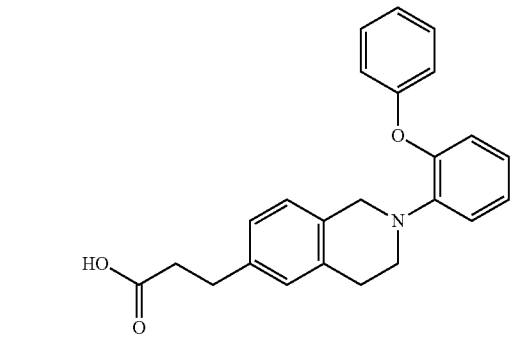

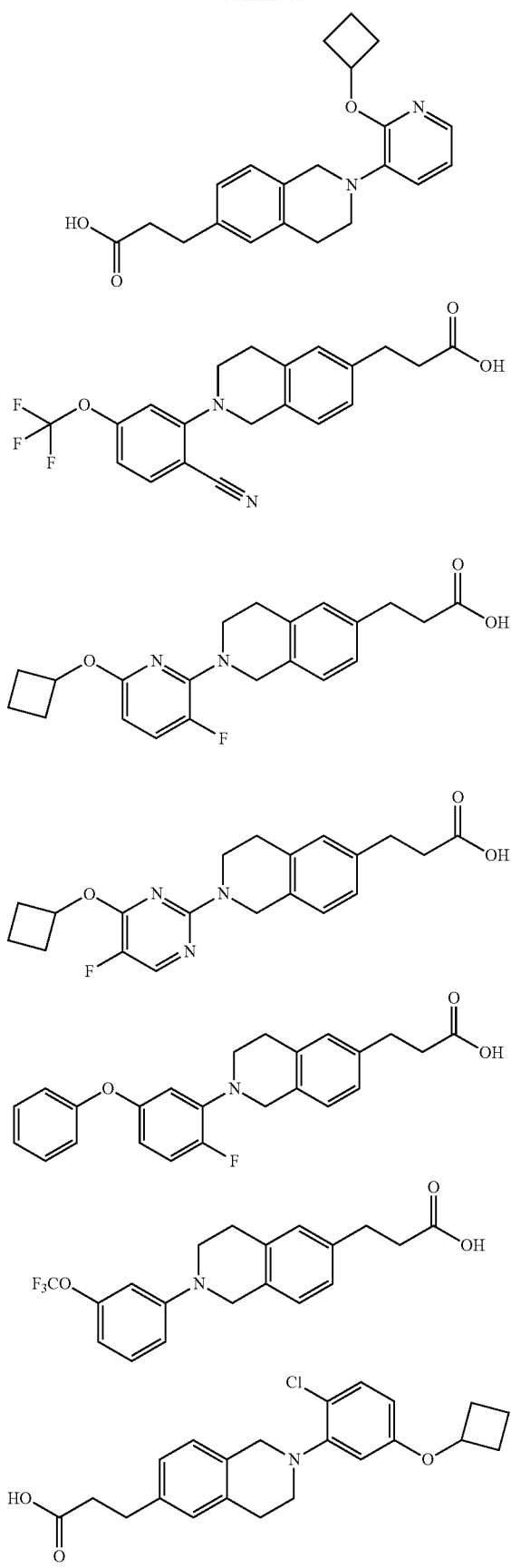
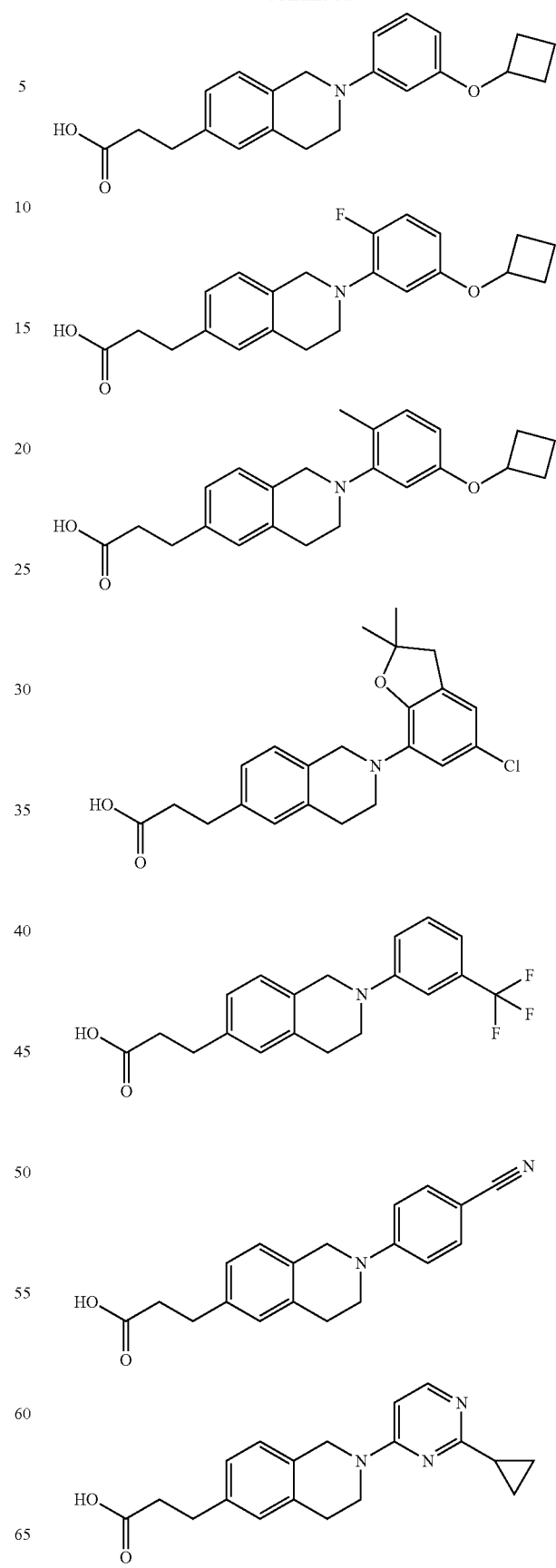

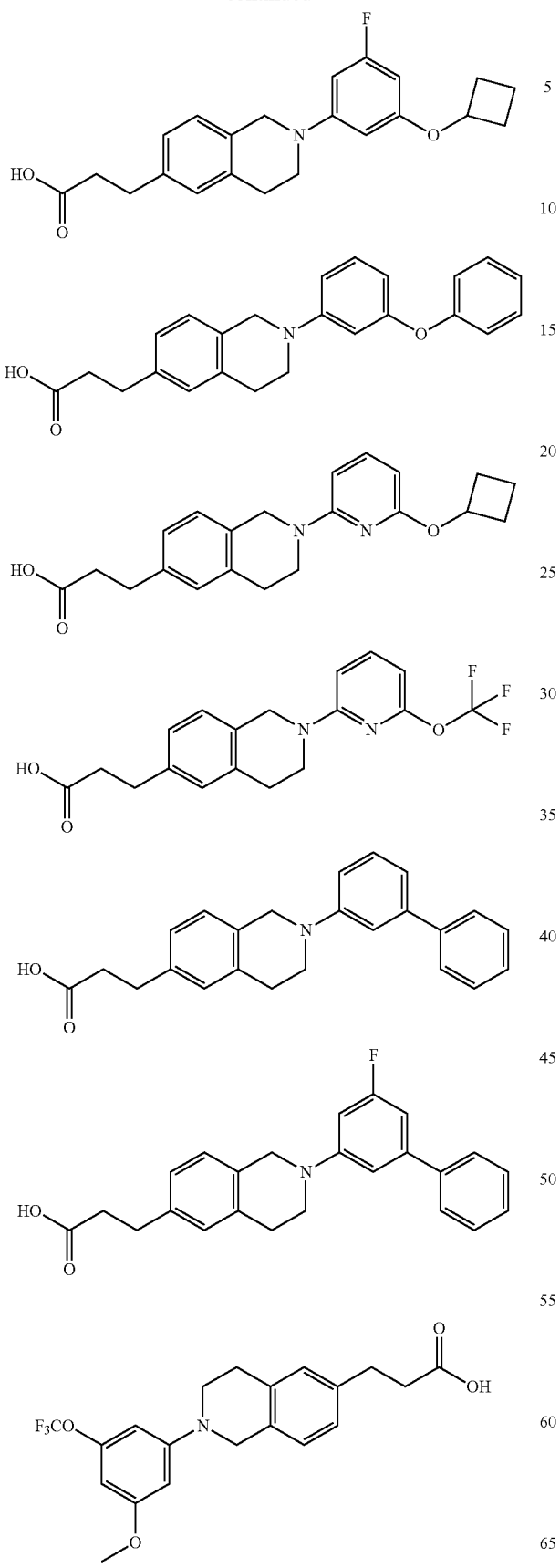
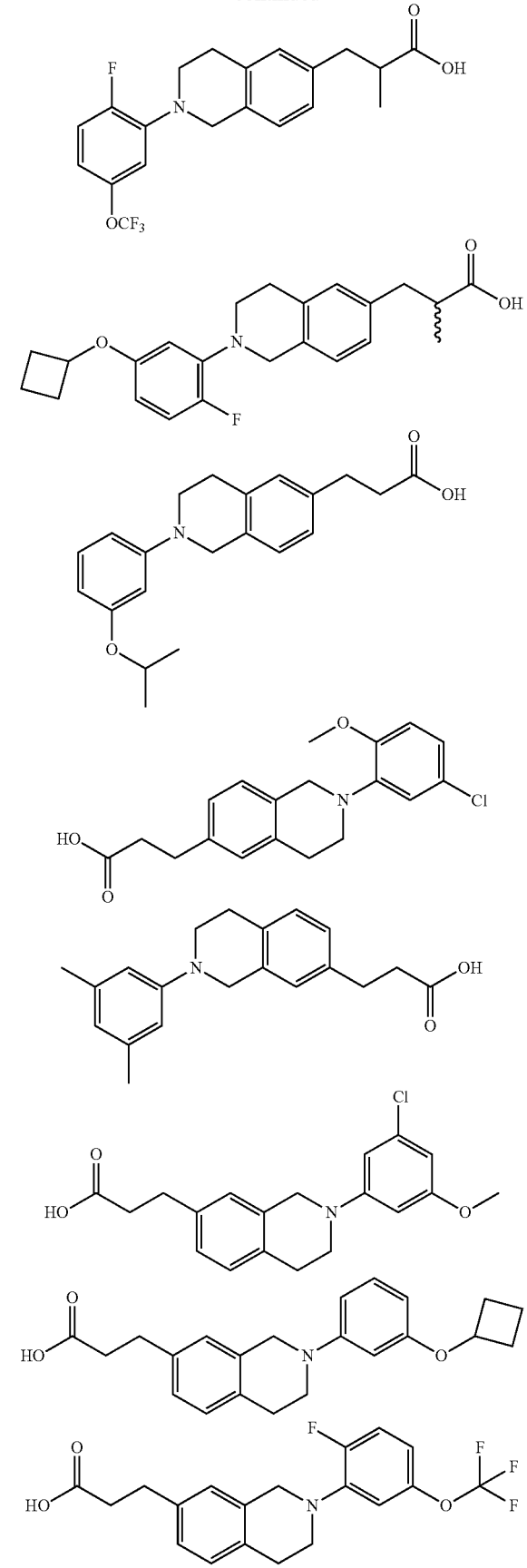

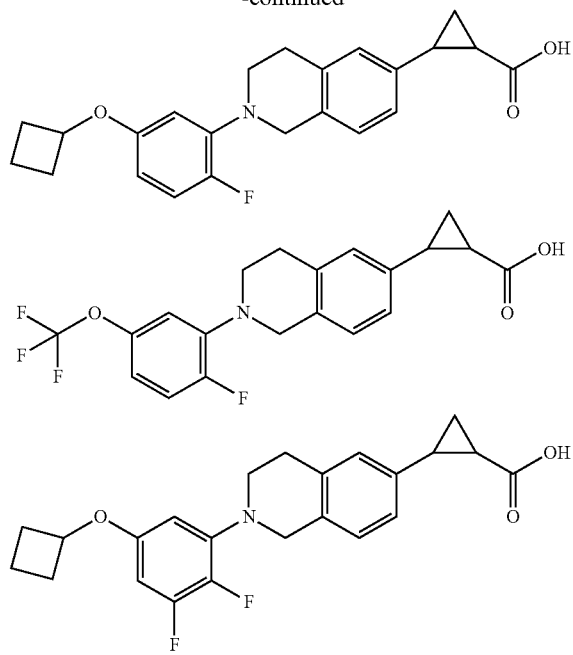
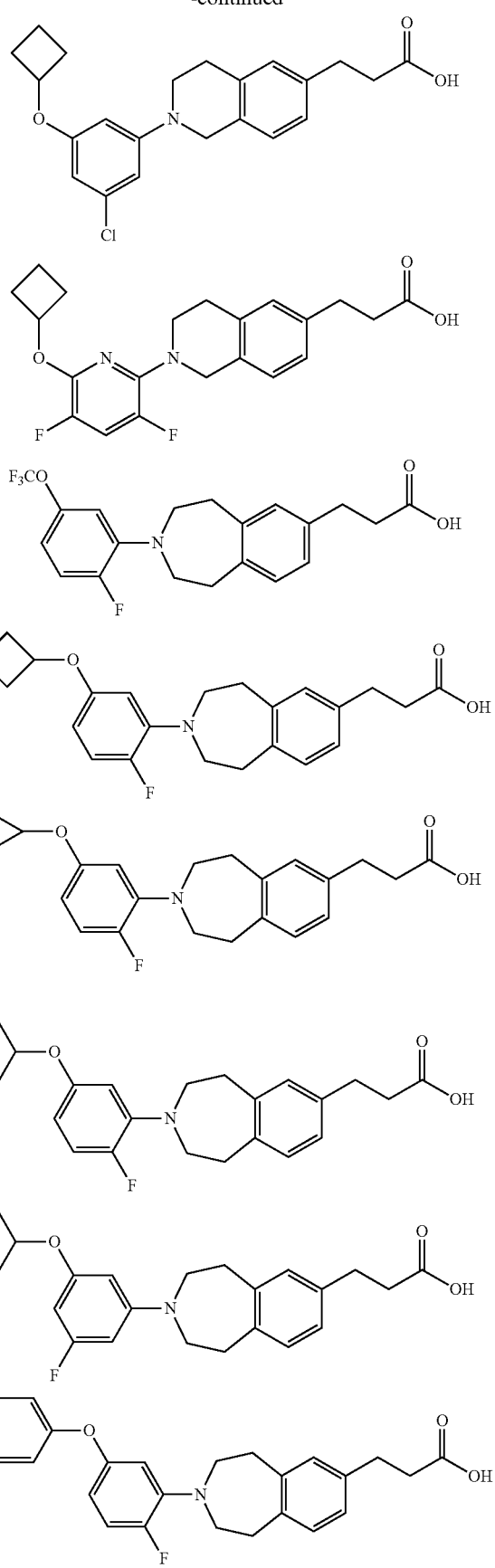

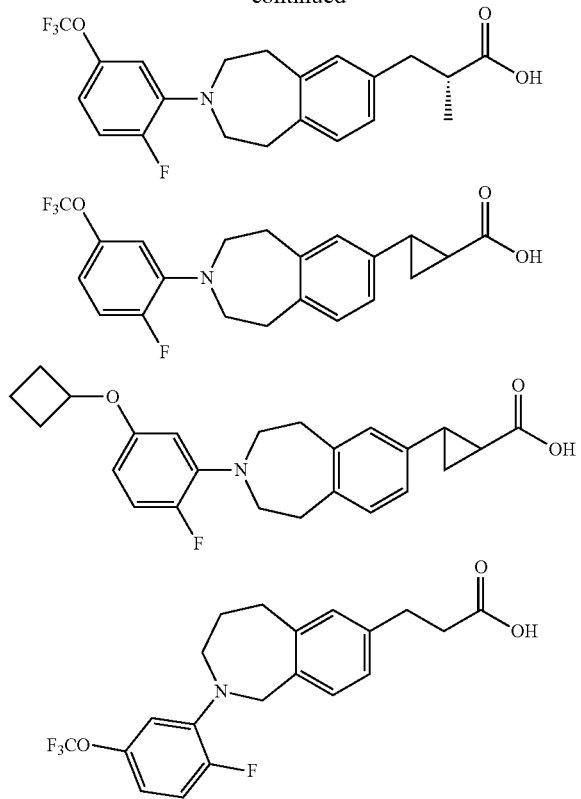
or a pharmaceutically acceptable salt or solvate (eg hydrate) thereof, or corresponding N-oxide or prodrug (eg ester prodrug).
Some preferred compounds of the invention are:
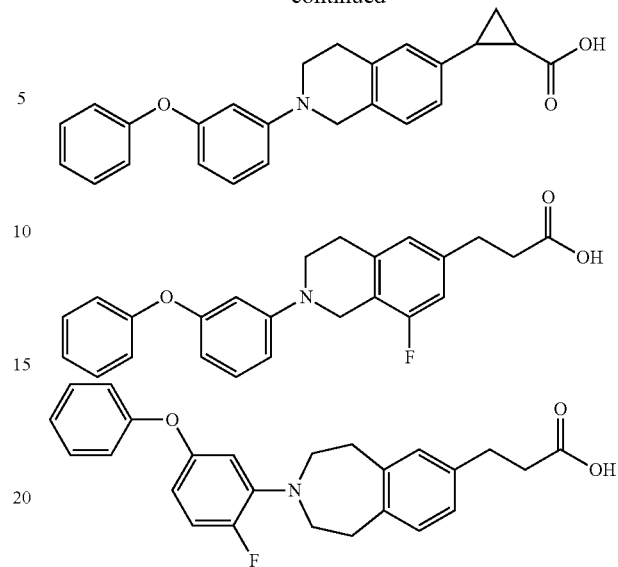
or a pharmaceutically acceptable salt or solvate (eg hydrate) thereof, or corresponding N-oxide or prodrug (eg ester prodrug).
Some preferred compounds of the invention are:

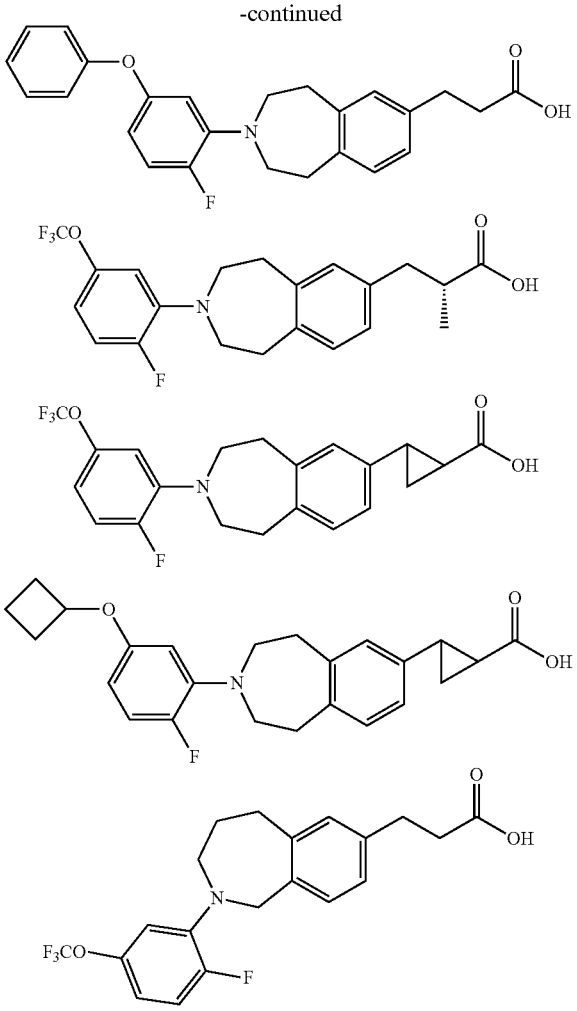

or a pharmaceutically acceptable salt or solvate (eg hydrate) thereof, or corresponding N-oxide or prodrug (eg ester prodrug).

The compound of the invention may be selected from the following group:
3-(2-(2-fluoro-5-(trifluoromethoxy)phenyl)-1,2,3,4-tetrahydroisoquinolin-6-yl)propanoic acid,
3-(2-(2-fluoro-5-(((1r,3r)-3-methoxycyclobutoxy)phenyl)-1,2,3,4-tetrahydroisoquinolin-6-yl)propanoic acid,
3-(2-(5-cyclobutoxy-2,3-difluorophenyl)-1,2,3,4-tetrahydroisoquinolin-6-yl)propanoic acid,
3-(2-(2-phenoxyphenyl)-1,2,3,4-tetrahydroisoquinolin-6-yl)propanoic acid,
3-(2-(2-cyclobutoxypyridin-3-yl)-1,2,3,4-tetrahydroisoquinolin-6-yl)propanoic acid,
3-(2-(2-cyano-5-(trifluoromethoxy)phenyl)-1,2,3,4-tetrahydroisoquinolin-6-yl)propanoic acid,
3-(2-(6-cyclobutoxy-3-fluoropyridin-2-yl)-1,2,3,4-tetrahydroisoquinolin-6-yl)propanoic acid,
3-(2-(4-cyclobutoxy-5-fluoropyrimidin-2-yl)-1,2,3,4-tetrahydroisoquinolin-6-yl)propanoic acid,
3-(2-(2-fluoro-5-phenoxyphenyl)-1,2,3,4-tetrahydroisoquinolin-6-yl)propanoic acid,
3-(2-(3-(trifluoromethoxy)phenyl)-1,2,3,4-tetrahydroisoquinolin-6-yl)propanoic acid,
3-(2-(2-chloro-5-cyclobutoxyphenyl)-1,2,3,4-tetrahydroisoquinolin-6-yl)propanoic acid,
3-(2-(3-cyclobutoxyphenyl)-1,2,3,4-tetrahydroisoquinolin-6-yl)propanoic acid,
3-(2-(5-cyclobutoxy-2-fluorophenyl)-1,2,3,4-tetrahydroisoquinolin-6-yl)propanoic acid,
3-(2-(5-cyclobutoxy-2-methylphenyl)-1,2,3,4-tetrahydroisoquinolin-6-yl)propanoic acid,
3-(2-(5-chloro-2,2-dimethyl-2,3-dihydrobenzofuran-7-yl)-1,2,3,4-tetrahydroisoquinolin-6-yl)propanoic acid,
3-(2-(3-(trifluoromethyl)phenyl)-1,2,3,4-tetrahydroisoquinolin-6-yl)propanoic acid,
3-(2-(4-cyanophenyl)-1,2,3,4-tetrahydroisoquinolin-6-yl)propanoic acid,
3-(2-(2-cyclopropylpyrimidin-4-yl)-1,2,3,4-tetrahydroisoquinolin-6-yl)propanoic acid,
3-(2-(3-cyclobutoxy-5-fluorophenyl)-1,2,3,4-tetrahydroisoquinolin-6-yl)propanoic acid,
3-(2-(3-phenoxyphenyl)-1,2,3,4-tetrahydroisoquinolin-6-yl)propanoic acid,
3-(2-(6-cyclobutoxypyridin-2-yl)-1,2,3,4-tetrahydroisoquinolin-6-yl)propanoic acid,
3-(2-(6-(trifluoromethoxy)pyridin-2-yl)-1,2,3,4-tetrahydroisoquinolin-6-yl)propanoic acid,
3-(2-([1,1'-biphenyl]-3-yl)-1,2,3,4-tetrahydroisoquinolin-6-yl)propanoic acid,
3-(2-(5-fluoro-[1,1'-biphenyl]-3-yl)-1,2,3,4-tetrahydroisoquinolin-6-yl)propanoic acid,
3-(2-(3-methoxy-5-(trifluoromethoxy)phenyl)-1,2,3,4-tetrahydroisoquinolin-6-yl)propanoic acid
3-(2-(2-fluoro-5-(trifluoromethoxy)phenyl)-1,2,3,4-tetrahydroisoquinolin-6-yl)-2-methylpropanoic acid,
3-(2-(5-cyclobutoxy-2-fluorophenyl)-1,2,3,4-tetrahydroisoquinolin-6-yl)-2-methylpropanoic acid 3-(2-(3-isopropoxyphenyl)-1,2,3,4-tetrahydroisoquinolin-6-yl)propanoic acid,
3-(2-(5-chloro-2-methoxyphenyl)-1,2,3,4-tetrahydroisoquinolin-6-yl)propanoic acid,
3-(2-(3,5-dimethylphenyl)-1,2,3,4-tetrahydroisoquinolin-7-yl)propanoic acid,
3-(2-(3-chloro-5-methoxyphenyl)-1,2,3,4-tetrahydroisoquinolin-7-yl)propanoic acid,
3-(2-(3-cyclobutoxyphenyl)-1,2,3,4-tetrahydroisoquinolin-7-yl)propanoic acid,
3-(2-(3,5-dimethylphenyl)-1,2,3,4-tetrahydroisoquinolin-7-yl)propanoic acid, 2-(2-(5-cyclobutoxy-2-fluorophenyl)-1,2,3,4-tetrahydroisoquinolin-6-yl)cyclopropanecarboxylic acid,
2-(2-(2-fluoro-5-(trifluoromethoxy)phenyl)-1,2,3,4-tetrahydroisoquinolin-6-yl)cyclopropane-1-carboxylic acid,
2-(2-(5-cyclobutoxy-2,3-difluorophenyl)-1,2,3,4-tetrahydroisoquinolin-6-yl)cyclopropane-1-carboxylic acid,
2-(2-(6-cyclobutoxy-3-fluoropyridin-2-yl)-1,2,3,4-tetrahydroisoquinolin-6-yl)cyclopropane-1-carboxylic acid,
2-(2-(3-Phenoxyphenyl)-1,2,3,4-tetrahydroisoquinolin-6-yl)cyclopropanecarboxylic acid,
3-(2-(5-cyclobutoxy-2-fluorophenyl)-7-fluoro-1,2,3,4-tetrahydroisoquinolin-6-yl)propanoic acid,
3-(8-fluoro-2-(2-fluoro-5-(trfluoromethoxy)phenyl)-1,2,3,4-tetrahydroisoquinolin-6-yl)propanoic acid,
3-(8-fluoro-2-(3-phenoxyphenyl)-1,2,3,4-tetrahydroisoquinolin-6-yl)propanoic acid,
3-(2-(3-Cyclobutoxy-5-fluorophenyl)-7-fluoro-1,2,3,4-tetrahydroisoquinolin-6-yl)propanoic acid,
3-(2-(3-chloro-5-cyclobutoxyphenyl)-1,2,3,4-tetrahydroisoquinolin-6-yl)propanoic acid,
3-(2-(6-Cyclobutoxy-3,5-difluoropyridin-2-yl)-1,2,3,4-tetrahydroisoquinolin-6-yl)propanoic acid, 3-(2-(2-Fluoro-5-(trifluoromethoxy)phenyl)-1,2,3,4-tetra-hydroisoquinolin-6-yl)propanoic acid,
3-(3-(5-cyclobutoxy-2-fluorophenyl)-2,3,4,5-tetrahydro-1H-benzo[d]azepin-7-yl)propanoic acid,
3-(3-(5-cyclopropoxy-2-fluorophenyl)-2,3,4,5-tetrahydro-1H-benzo[d]azepin-7-yl)propanoic acid,
3-(3-(2-fluoro-5-isopropoxyphenyl)-2,3,4,5-tetrahydro-1H-benzo[d]azepin-7-yl)propanoic acid,
3-(3-(3-fluoro-5-isopropoxyphenyl)-2,3,4,5-tetrahydro-1H-benzo[d]azepin-7-yl)propanoic acid,
3-(3-(2-fluoro-5-phenoxyphenyl)-2,3,4,5-tetrahydro-1H-benzo[d]azepin-7-yl)propanoic acid
(R)-3-(3-(2-fluoro-5-(trifluoromethoxy)phenyl)-2,3,4,5-tetrahydro-1H-benzo[d]azepin-7-yl)-2-methylpropanoic acid,
2-(3-(2-fluoro-5-(trifluoromethoxy)phenyl)-2,3,4,5-tetrahydro-1H-benzo[d]azepin-7-yl)cyclopropanecarboxylic acid,
3-(3-(5-cyclobutoxy-2-fluorophenyl)-2,3,4,5-tetrahydro-1H-benzo[d]azepin-7-yl)propanoic acid, and
3-(2-(2-Fluoro-5-(trifluoromethoxy)phenyl)-2,3,4,5-tetrahydro-1H-benzo[c]azepin-7-yl)propanoic acid,
or a pharmaceutically acceptable salt or solvate (eg hydrate) thereof, or corresponding N-oxide or prodrug (eg ester prodrug).

Particular compounds of the invention may be selected from the following group:
3-(2-(2-phenoxyphenyl)-1,2,3,4-tetrahydroisoquinolin-6-yl)propanoic acid,
3-(2-(2-fluoro-5-phenoxyphenyl)-1,2,3,4-tetrahydroisoquinolin-6-yl)propanoic acid,
3-(2-(3-phenoxyphenyl)-1,2,3,4-tetrahydroisoquinolin-6-yl)propanoic acid,
2-(2-(3-phenoxyphenyl)-1,2,3,4-tetrahydroisoquinolin-6-yl)cyclopropanecarboxylic acid,
3-(8-fluoro-2-(3-phenoxyphenyl)-1,2,3,4-tetrahydroisoquinolin-6-yl)propanoic acid, and
3-(3-(2-fluoro-5-phenoxyphenyl)-2,3,4,5-tetrahydro-1H-benzo[d]azepin-7-yl)propanoic acid,
or a pharmaceutically acceptable salt or solvate (eg hydrate) thereof, or corresponding N-oxide or prodrug (eg ester prodrug).

Particular compounds of the invention may be selected from the following group:
3-(3-(2-fluoro-5-(trifluoromethoxy)phenyl)-2,3,4,5-tetrahydro-1H-benzo[d]azepin-7-yl)propanoic acid,
3-(3-(5-cyclobutoxy-2-fluorophenyl)-2,3,4,5-tetrahydro-1H-benzo[d]azepin-7-yl)propanoic acid,
3-(3-(5-cyclopropoxy-2-fluorophenyl)-2,3,4,5-tetrahydro-1H-benzo[d]azepin-7-yl)propanoic acid,
3-(3-(3-fluoro-5-isopropoxyphenyl)-2,3,4,5-tetrahydro-1H-benzo[d]azepin-7-yl)propanoic acid,
3-(3-(2-fluoro-5-isopropoxyphenyl)-2,3,4,5-tetrahydro-1H-benzo[d]azepin-7-yl)propanoic acid,
3-(3-(2-fluoro-5-phenoxyphenyl)-2,3,4,5-tetrahydro-1H-benzo[d]azepin-7-yl)propanoic acid
(R)-3-(3-(2-fluoro-5-(trifluoromethoxy)phenyl)-2,3,4,5-tetrahydro-1H-benzo[d]azepin-7-yl)-2-methylpropanoic acid,
2-(3-(2-fluoro-5-(trifluoromethoxy)phenyl)-2,3,4,5-tetrahydro-1H-benzo[d]azepin-7-yl)cyclopropanecarboxylic acid,
3-(3-(5-cyclobutoxy-2-fluorophenyl)-2,3,4,5-tetrahydro-1H-benzo[d]azepin-7-yl)propanoic acid, and
3-(2-(2-fluoro-5-(trfluoromethoxy)phenyl)-2,3,4,5-tetrahydro-1H-benzo[c]azepin-7-yl)propanoic acid,
or a pharmaceutically acceptable salt or solvate (eg hydrate) thereof, or corresponding N-oxide or prodrug (eg ester prodrug).

In some embodiments, a compound of the present invention comprises a stereomerically pure S-enantiomer. In other embodiments, the compound comprises a stereomerically pure R-enantiomer. In yet other embodiments, the compound comprises a mixture of S- and R-enantiomers.

The compounds of the invention are believed to modulate (ie activate or inhibit) GPR120. In particular, the compounds of the invention are believed to be GPR120 agonists.

Accordingly, the compounds of the invention find use as therapeutic agents for modulating diseases or conditions associated with GPR120 activity. A disease or condition may be associated with GPR120 because it is responsive to modulation of GPR120, mediated by GPR120 and/or mediated by pancreatic beta-cells.

GPR120 agonists are thought to stimulate secretion of insulin, glucagon-like peptide 1 (GLP-1), and glucose-dependent insulinotropic polypeptide (GIP) in a mammal, thereby lowering blood glucose levels. Insulin is secreted by pancreatic beta-cells. Thus, by modulating GPR120, the compounds of the invention may be capable of regulating insulin levels in a subject, GLP-1 levels, blood glucose levels and/or insulin sensitivity.

Examples of diseases and conditions that are associated with GPR120 activity are type 1 or 2 diabetes, obesity, hyperglycaemia, glucose intolerance, insulin resistance, hyperinsulinaemia, hypercholesterolaemia, hypertension, hyperlipoproteinaemia, hyperlipidaemia, hypertriglylceridaemia, dyslipidaemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycaemia, hypertension, cancer, NASH and edema.

Thus, there is provided a compound of formula (I) for use in the treatment of a disease or condition associated with GPR120 activity. There is also provided the use of a compound of formula (I) in the manufacture of a medicament for the treatment of a disease or condition associated with GPR120 activity.

Further, there is provided a compound of formula (I) as described above for use in the treatment of a disease or condition selected form the group consisting of type 1 or 2 diabetes, obesity, hyperglycaemia, glucose intolerance, insulin resistance, hyperinsulinaemia, hypercholesterolaemia, hypertension, hyperlipoproteinaemia, hyperlipidaemia, hypertriglylceridaemia, dyslipidaemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycaemia, hypertension, cancer, NASH, and edema. Likewise, there is provided a compound for formula (I) as described above for use in the manufacture of a medicament for the treatment of a disease or condition selected from that list.

The invention also provides a method of treating a subject suffering from or susceptible to, a disease or condition associated with GPR120 activity, which method comprises administering to the subject a therapeutically or prophylactically effective amount of a compound of formula (I).

The invention provides a method for treating a disease or condition selected from the group consisting of type 1 or 2 diabetes, obesity, hyperglycaemia, glucose intolerance, insulin resistance, hyperinsulinaemia, hypercholesterolaemia, hypertension, hyperlipoproteinaemia, hyperlipidaemia, hypertriglylceridaemia, dyslipidaemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycaemia, hypertension, cancer, NASH, and edema. Such methods comprise administering to the subject a therapeutically or prophylactically effective amount of a compound of formula (I). The disease or condition may be type 2 diabetes.

In another aspect, the invention provides a method for modulating circulating insulin concentration in a subject, comprising administering to the subject a therapeutically or prophylactically effective amount of a compound of formula (I).

Additionally, the compounds may be useful for the treatment and/or prevention of complications of these diseases and conditions (eg, type 2 diabetes, sexual dysfunction, dyspepsia and so forth).

GPR agonists may be used to treat, counteract or prevent obesity as demonstrated by Ichimura et al (Nature; Published online 19 Feb. 2012). Also CNS and autoimmune diseases may be treated with GPR agonists. Thus, other diseases that may be treated by a compound of the invention include obesity and CNS and autoimmune diseases.

Cartoni et al (The Journal of Neuroscience, Jun. 23, 2010•30(25):8376-8382), Matsumura et al (Neuroscience Letters 450 (2009) 186-190), and Galindo et al (Chem. Senses 37: 123-139, 2012) demonstrate that GPR120 agonists appear to increase fat taste perception. Thus, the compounds of the present invention may also be useful as taste additives in food products.

While the compounds of the invention are believed to exert their effects by interacting with GPR120, the mechanism of action by which the compounds act is not a limiting embodiment of the invention.

In another aspect, the invention provides a pharmaceutical composition comprising a compound of formula (as defined above and one or more pharmaceutically acceptable excipients. The composition may also comprise a pharmaceutically acceptable carrier and/or diluent.

The term "composition" as used herein is intended to encompass a product comprising the specified ingredients (and in the specified amounts, if indicated), as well as any product which results, directly or indirectly, from combination of the specified ingredients in the specified amounts.

By "pharmaceutically acceptable" it is meant that the carrier, excipient, or diluent is compatible with the other ingredients of the formulation and is not deleterious to the recipient thereof.

Composition formulations may improve one or more pharmacokinetic properties (eg oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavouring agents, colouring agents and preserving agents in order to provide pharmaceutically elegant and palatable preparations.

Tablets may contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol.

Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative, and flavouring and colouring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions etc containing the compounds of the invention are employed. As used herein, topical application is also meant to include the use of mouthwashes and gargles.

The pharmaceutical compositions of the invention may further comprise other therapeutically active compounds, as noted herein, useful in the treatment of type 2 diabetes, obesity, hyperglycaemia, glucose intolerance, insulin resistance, hyperinsulinaemia, hypercholesterolaemia, hypertension, hyperlipoproteinaemia, hyperlipidaemia, hypertriglylceridaemia, dyslipidaemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycaemia, cancer, NASH, and edema.

Pharmaceutical compositions for use in the treatment of type 2 diabetes may additionally comprise other anti-diabetic drugs.

Depending on the disease to be treated and the subject's condition, the compounds and compositions of the invention may be administered by oral, parenteral (eg intramuscular, intraperitoneal, intravenous, ICV, intracisternal injection or infusion, subcutaneous injection or implant), inhalation, nasal, vaginal, rectal, sublingual, or topical (eg transdermal, local) routes of administration and may be formulated, alone or together, in suitable dosage unit formulations containing conventional non-toxic pharmaceutically acceptable carriers, adjuvants and vehicles appropriate for each route of administration.

The invention also contemplates administration of the compounds and compositions of the invention in a depot formulation, in which the active ingredient is released over a defined time period.

In the treatment or prevention of type 2 diabetes, obesity, hyperglycaemia, glucose intolerance, insulin resistance, hyperinsulinaemia, hypercholesterolaemia, hypertension, hyperlipoproteinaemia, hyperlipidaemia, hypertriglylceridaemia, dyslipidaemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycaemia, cancer, NASH, and edema or other conditions or disorders associated with GPR120, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type 2 diabetes, obesity, hyperglycaemia, glucose intolerance, insulin resistance, hyperinsulinaemia, hypercholesterolaemia, hypertension, hyperlipoproteinaemia, hyperlipidaemia, hypertriglylceridaemia, dyslipidaemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycaemia, cancer, NASH, and edema. Such other agents, or drugs, may be administered, by a route and in an amount commonly used, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition mediated by GPR120. In some embodiments, therapeutic compositions are provided that include a compound of the invention and a second therapeutic agent as a combined preparation for simultaneous, separate or sequential use in the prophylactic treatment of a subject at risk for a disease or condition associated with GPR120 activity. In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (eg lovastatin, simvastatin, pravastatin, fluvastatin, atorvastatin and other statins), bile acid sequestrants (eg cholestyramine and colestipol), vitamin B3 (also known as nicotinic acid, or niacin), vitamin B6 (pyridoxine), vitamin B12 (cyanocobalamin), fibric acid derivatives (eg gemfibrozil, clofibrate, fenofibrate and benzafibrate), probucol, nitroglycerin, and inhibitors of cholesterol absorption (eg beta-sitosterol and acylCoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (eg streptokinase, alteplase, anistreplase and reteplase), heparin, hirudin and warfarin derivatives, beta-blockers (eg atenolol), beta-adrenergic agonists (eg isoproterenol), ACE inhibitors and vasodilators (eg sodium nitroprusside, nicardipine hydrochloride, nitroglycerin and enaloprilat); and (c) anti-diabetic agents. In some embodiments, a compound of the invention may be administered along with a DPP-IV inhibitor, an SGLT-2 inhibitor or a GLP-I agonist.

The weight ratio of the compound of the invention to the second therapeutic ingredient may be varied and will depend upon the effective dose of each ingredient. Generally, an effective dose of each will be used. Combinations of a compound of the invention and other therapeutic ingredients will generally also be within the aforementioned range, but in each case, an effective dose of each therapeutic ingredient should be used.

In currently preferred embodiments, the compounds of the invention are used in the treatment of type 2 diabetes in combination with one or more anti-diabetic agents.

The anti-diabetic agent or agents used in combination with a compound of the invention may be any suitable anti-diabetic agent known in the art. In particular, suitable anti-diabetic drugs include, but are not limited to, the following:

Insulin and insulin mimetics, sulfonylureas (eg glyburide, meglinatide, glimepiride and glipizide), biguanides, eg metformin (GLUCOPHAGE®), glucosidase inhibitors (eg acarbose, miglitol and voglibose), insulin sensitisers, eg thiazolidinedione compounds, rosiglitazone (Avandia), troglitazone (Rezulin), pioglitazone (ACTOS®), Dipeptidyl Peptidase-4 inhibitors, eg vildagliptin (Galvus®), sitagliptin (Januvia), saxagliptin, linagliptin, alogliptin, septagliptin and teneligliptin, SGLT-2 inhibitors eg canagliflozin (Invokana), empagliflozin (Jardiance®) and dapagliflozin (Forxiga®), GLP-1 analogs, eg exenatide (Byetta), liraglutide, taspoglutide and lixisenatide, meglitinides, eg nateglinide, and gastric inhibitory peptide analogues.

There is provided a compound of formula (I) for use in the treatment of type 2 diabetes, wherein the treatment further comprises one or more anti-diabetic agents. Likewise, there is provided the use of a compound of formula (I) in the manufacture of a medicament for the treatment of type 2 diabetes, wherein the treatment further comprises one or more anti-diabetic agents.

There is also provided a compound for formula (I) for use in the treatment of type 2 diabetes, or the use of such a compound in the manufacture of a medicament for the treatment of diabetes, wherein the treatment further comprises one or more anti-diabetic agents selected from metformin, and thiazolidinedione drugs such as pioglitazone and rosiglitazone.

The compound of the invention may be administered before the one or more additional therapeutic agents, simultaneously with the one or more therapeutic agents, or after the one or more therapeutic agents. The compound or composition of the invention may be provided with one or more other therapeutic agents in a kit.

There is also provided a method of treating a subject having type 2 diabetes, which method comprises administration to the subject of a therapeutically or prophylactically effective amount of a compound of formula (I).

There is also provided a method of treating a subject having type 2 diabetes, which method comprises administration to the subject of a therapeutically or prophylactically effective amount of a compound of formula (I), in combination with one or more anti-diabetic agents.

There is also provided a method of treating a subject having type 2 diabetes, which method comprises administration to the subject of a therapeutically or prophylactically effective amount of a compound of formula (I), in combination with one or more anti-diabetic agents selected from metformin, a DPPIV inhibitor eg sitagliptin, an SGLT-2 inhibitor eg dapagliflozin and thiazolidinedione drugs such as pioglitazone and rosiglitazone.

With reference to the methods of the present invention, the following terms are used with the noted meanings:

The terms "treating" or "treatment" of a disease includes inhibiting the disease, ie arresting or reducing the development of the disease or its clinical symptoms, or relieving the disease, ie causing regression of the disease or its clinical symptoms.

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight etc of the mammal to be treated.

The term "mammal" includes, without limitation, humans, domestic animals (eg dogs or cats), farm animals (cows, horses, or pigs), and laboratory animals (mice, rats, hamsters, guinea pigs, pigs, rabbits, dogs, or monkeys).

The term "insulin resistance" can be defined generally as a disorder of glucose metabolism. More specifically, insulin resistance can be defined as the diminished ability of insulin to exert its biological action across a broad range of concentrations producing less than the expected biologic effect (see, eg, Reaven G M, J. Basic & Clin. Phys. & Pharm. (1998) 9:387-406 and Flie J, Ann. Rev. Med. (1983) 34:145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, metabolic syndrome, hypertension, obesity, atherosclerosis and a variety of other disorders. Eventually, the insulin resistant individuals can progress to a point where a diabetic state is reached.

The term "diabetes mellitus" or "diabetes" means a disease or condition that is generally characterised by metabolic defects in production and utilization of glucose that result in the failure to maintain appropriate blood sugar levels in the body. The result of these defects is elevated blood glucose, referred to as "hyperglycaemia". Two major forms of diabetes are type 1 diabetes and type 2 diabetes. As described above, type 1 diabetes is generally the result of an absolute deficiency of insulin, the hormone that regulates glucose utilisation. Type 2 diabetes often occurs in the face of normal, or even elevated levels of insulin and can result from the inability of tissues to respond appropriately to insulin. Most type 2 diabetic patients are insulin resistant and have a relative deficiency of insulin, in that insulin secretion cannot compensate for the resistance of peripheral tissues to respond to insulin. In addition, many type 2 diabetics are obese. Other types of disorders of glucose homeostasis include impaired glucose tolerance, which is a metabolic stage intermediate between normal glucose homeostasis and diabetes, and gestational diabetes mellitus, which is glucose intolerance in pregnancy in women with no previous history of type 1 or type 2 diabetes.

The term "metabolic syndrome" refers to a cluster of metabolic abnormalities including abdominal obesity, insulin resistance, glucose intolerance, diabetes, hypertension and dyslipidaemia. These abnormalities are known to be associated with an increased risk of vascular events.

The guidelines for diagnosis of type 2 diabetes, impaired glucose tolerance, and gestational diabetes have been outlined by the American Diabetes Association (see, eg, The Expert Committee on the Diagnosis and Classification of Diabetes Mellitus, Diabetes Care, (1999) Vol. 2 (Suppl 1):S5-19).

The term "secretagogue" means a substance or compound that stimulates secretion. For example, an insulin secretagogue is a substance or compound that stimulates secretion of insulin.

The reference to a "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, eg increased susceptibility to certain infections (especially fungal and staphylococcal infections), nausea, and ketoacidosis (enhanced production of ketone bodies in the blood).

The reference to a "complication" of diabetes includes, but is not limited to, microvascular complications and macrovascular complications. Microvascular complications are those complications that generally result in small blood vessel damage. These complications include, eg retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications that generally result from large blood vessel damage. These complications include, eg cardiovascular disease and peripheral vascular disease. Cardiovascular disease refers to diseases of blood vessels of the heart. See, eg Kaplan R M, et al, "Cardiovascular diseases" in Health and Human Behavior, pp. 206-242 (McGraw-Hill, New York 1993). Cardiovascular disease is generally one of several forms, including, eg hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognised and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "modulate" or "modulating" refers to the treating, prevention, suppression, enhancement, or induction of a function or condition. For example, compounds can modulate type 2 diabetes by increasing insulin in a human, thereby suppressing hyperglycaemia. Compounds can also modulate GPR120 by acting as GPR120 agonists. The term "triglyceride(s)" ("TGs"), as used herein, incorporates its common usage. TGs consist of three fatty acid molecules esterified to a glycerol molecule. TGs serve to store fatty acids that are used by muscle cells for energy production or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidaemia" refers to abnormal levels of lipoproteins in blood plasma including both depressed and/or elevated levels of lipoproteins (eg elevated levels of LDL and/or VLDL, and depressed levels of HDL).

The term "hyperlipidaemia" includes, but is not limited to, the following:

(1) Familial Hyperchylomicronaemia, a rare genetic disorder that causes a deficiency in an enzyme, LP lipase, that breaks down fat molecules. The LP lipase deficiency can cause the accumulation of large quantities of fat or lipoproteins in the blood;

(2) Familial Hypercholesterolaemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidaemia, also known as multiple lipoprotein-type hyperlipidaemia is an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine, which can cause reduced affinity of LDL particles for the LDL receptor. Consequently, this can cause high plasma LDL and total cholesterol levels;

(5) Familial Dysbetalipoproteinaemia, also referred to as type 3 Hyperlipoproteinaemia, is an uncommon inherited disorder resulting in moderate to severe elevations of serum TG and cholesterol levels with abnormal apolipoprotein E function. HDL levels are usually normal; and (6) Familial Hypertriglyceridaemia, is a common inherited disorder in which the concentration of plasma VLDL is elevated. This can cause mild to moderately elevated TG levels (and usually not cholesterol levels) and can often be associated with low plasma HDL levels.

Risk factors for hyperlipidaemia include, but are not limited to, the following: (1) disease risk factors, such as a history of type 1 diabetes, type 2 diabetes, Cushing's syndrome, hypothyroidism and certain types of renal failure; (2) drug risk factors, which include, birth control pills; hormones, such as oestrogen, and corticosteroids; certain diuretics; and various [beta]-blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index ("BMI") greater than 27.8 kg/m² for men and 27.3 kg/m² for women (BMI equals weight (kg)/height (m²)). Obesity is linked to a variety of medical conditions including diabetes and hyperlipidaemia. Obesity is also a known risk factor for the development of type 2 diabetes (see, eg, Barrett-Conner E, Epidemol. Rev. (1989) 11:172-181; and Knowler, et al, Am. J. Clin. Nutr. (1991) 53:1543-1551).

The term "insulin" refers to a polypeptide hormone that regulates glucose metabolism. Insulin binds to insulin receptors in insulin sensitive cells and mediates glucose uptake. Insulin is used to treat type 1 diabetes and may be used to treat type 2 diabetes.

The term "GLP-1" or "glucagon-like peptide" is a peptide hormone primarily produced by L cells in the gut. GLP-1 increases insulin secretion, decreases glucagon secretion, increases beta cell mass and insulin gene expression, inhibits acid secretion and gastric emptying in the stomach, and decreases food intake by increasing satiety.

The term "GIP" or "gastric inhibitory peptide" or "glucose dependent insulinotropic polypeptide" refers to a peptide hormone produced primarily by K cells in the gut. GIP stimulates insulin secretion. GIP also has significant effects on lipid metabolism.

The term "agonist" refers to a compound that binds to a receptor and triggers a response in a cell. An agonist mimics the effect of an endogenous ligand, a hormone for example, and produces a physiological response similar to that produced by the endogenous ligand.

Compounds of formula (I) may be prepared by various methods that will be familiar or readily apparent to those skilled in the art.

According to another aspect of the invention, there is provided a process for the preparation of compounds of formula I comprising:

reacting a compound of formula (II)

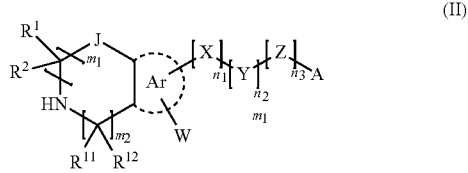

with a compound of formula (III)

wherein $R^1$, $R^2$, $R^{11}$, $R^{12}$, J, Ar, W, X, Y, Z, A, $m_1$, $m_2$, $n_1$, $n_2$, $n_3$, G and B are as set out above in relation to formula (I).

The compounds of formula (II) or formula (III) may be optionally provided with appropriate protecting groups in which case the process may additionally comprise a further step in which the product is deprotected to produce the compound of formula (I).

Abbreviations

AcOH: acetic acid; APCI: atmospheric pressure chemical ionisation; BINAP: (2,2'-bis(diphenylphosphino)-1,1'-binaphthyl); CDCl₃: deuterated chloroform; Cs₂CO₃: caesium carbonate; dba: dibenzylideneacetone; DCM: dichloromethane; DIAD: diisopropyl azodicarboxylate; DIPEA: N,N-diisopropylethylamine; DMAP: 4-dimethylaminopyridine; DMF: N,N-dimethylformamide; DMSO: dimethylsulfoxide; (ES⁺): electrospray ionization positive mode; EtOAc: ethyl acetate; EtOH: ethanol; h: hours; HCl: hydrochloric acid; HPLC: high performance liquid chromatography; K₂CO₃: potassium carbonate; KI: potassium iodide; LCMS: liquid chromatography—mass spectrometry; LiOH: lithium hydroxide; M: molar; [M+H]⁺: protonated molecular ion; MeCN: acetonitrile; MeI: methyl iodide; MeOH: methanol; min: minutes; $MgSO_4$: magnesium sulfate; MS: mass spectrometry; MTBE: methyl tert-butyl ether; m/z: mass-to-charge ratio; NaCl: sodium chloride; $Na_2CO_3$: sodium carbonate; NaH: sodium hydride; $NaHCO_3$: sodium bicarbonate; NaOH: sodium hydroxide; $Na_2SO_4$: sodium sulfate; $Na_2S_2O_3$: sodium thiosulfate; $NH_4Cl$: ammonium chloride; NMR: nuclear magnetic resonance; Pd/C: palladium on carbon; Pd-162: (chloro(crotyl)(tri-tert-butylphosphine)palladium(II); Pd-176: allyl[(R)-2,2'-bis(diphenylphosphino)-1,1'-binaphthalene]palladium(II) chloride; pet.: petroleum; $Ph_3P$: triphenylphosphine; Pt/C: platinum on carbon; RT: room temperature (ca. 20° C.); $R_t$: retention time; RuPhos: 2-dicyclohexylphosphino-2',6'-diisopropoxybiphenyl; sat: saturated; SCX: strong cation exchange; TBACl: tetrabutylammonium chloride; TBAI: tetrabutylammonium iodide; THF: tetrahydrofuran; TFA: trifluoroacetic acid; UPLC: ultra performance liquid chromatography; UV: ultra-violet.

EXAMPLES

General Experimental Conditions

All starting materials and solvents were obtained either from commercial sources or prepared according to literature methods.

Silica gel chromatography was performed on an automated flash chromatography system, such as CombiFlash Companion, CombiFlash Rf system or Reveleris X2 flash system using RediSep® Rf or Reveleris® or the GraceResolv™ pre-packed silica (230-400 mesh, 40-63 µm) cartridges.

Analytical LCMS experiments to determine retention times and associated mass ions were performed using either: Waters Acquity H-class UPLC system with a QDa mass detector; Agilent 1200 series HPLC system coupled to an Agilent 6110 or 6120 series single quadrupole mass spectrometer; or Dionex Ultimate 3000 series HPLC system coupled to an Advion expression CMS using APCI ionization.

Preparative HPLC purifications were performed using a Waters X-Select CSH C18, 5 µm, 19×50 mm column using a gradient of 0.1% formic acid in MeCN and 0.1% aqueous formic acid. Fractions were collected following detection by either UV at a single wavelength measured by a variable wavelength detector on a Gilson 215 or a Varian PrepStar preparative HPLC, or by mass ion and UV detection at a single wavelength measured by a ZQ single quadrupole mass spectrometer, with positive and negative ion electrospray, and dual wavelength detection on a Waters FractionLynx LCMS.

NMR spectra were recorded using a Bruker Avance III 400 MHz instrument or a Bruker Avance III HD 500 MHz instrument, using either residual non-deuterated solvent or tetra-methylsilane as reference.

High-resolution mass spectra (HRMS) were obtained on a Bruker micrOTOF-Q II (ESI).

pEC50 data was obtained by the following procedure:
Human GPR120-β Arrestin 2 Bio-Luminescence Resonance Energy Transfer (BRET) Agonist Assay Procedure HEK293T cells were cultured in growth media composed of DMEM L-glutamine media supplemented with 10% (v:v) fetal bovine serum (FBS) and 1% (v:v) 10,000 units penicillin/10 mgml⁻¹ streptomycin at 37° C., 5% $CO_2$. HEK293T cells transiently co-expressing human GPR120 (FFA1) and b-arrestin 2 were generated by transfection with plasmids encoding a construct of hGPR120 (FFA1) fused at its C terminal with enhanced yellow fluorescent protein (eYFP), and another encoding β-arrestin 2 fused to *Renilla* luciferase (RLuc), using Polyethylenimine (PEI) as the transfection reagent.

Transfected cells were cryopreserved in batches for consistency between replicate assays. Twenty-four hours post transfection, cells were harvested with non-enzymatic cell dissociation buffer and re-suspended in DMEM medium supplemented with 10% DMSO and 10% FBS before being transferred first to −80° C. overnight and then to liquid nitrogen for long-term storage. On the day prior to the assay, cells were thawed at 37° C. and re-suspended in growth media. A 96 well white opaque bottom microtitre plate was then seeded with 40,000 cells in a volume of 100 µl growth media per well and seeded plates were then incubated overnight at 37° C., 5% $CO_2$. On the day of the BRET experiment, cells were washed twice with BRET assay buffer (Hanks balanced salt solution (HBSS) supplemented with 10 mM HEPES (pH 7.4)), then 80 µl per well of BRET assay buffer was added before the plate was incubated for 30 minutes at 37° C., 5% $CO_2$. Then, *Renilla* luciferase substrate coelenterazine h (5 µM) was added to the cells and incubated at 37° C. for 10 minutes before the addition of GPR120 agonist (TUG-891) or test compound for a further 5 minutes at 37° C.

Bio-luminescence at λ 535 nm and λ 475 nm was then measured with a Pherastar FsX instrument, and the λ 535/λ 475 ratio of bio-luminescence was then used to calculate a BRET value. hGPR120 agonist potency values ($pEC_{50}$) were calculated by normalising the BRET values to the DMSO vehicle (0% control) and TUG-891 (100% control) and then fitting the normalised data to a 3-parameter concentration-response curve.

Experimental Scheme 1

Compound 1 3-(2-(2-Fluoro-5-(trifluoromethoxy) phenyl)-1,2,3,4-tetrahydroisoquinolin-6-yl)propanoic Acid

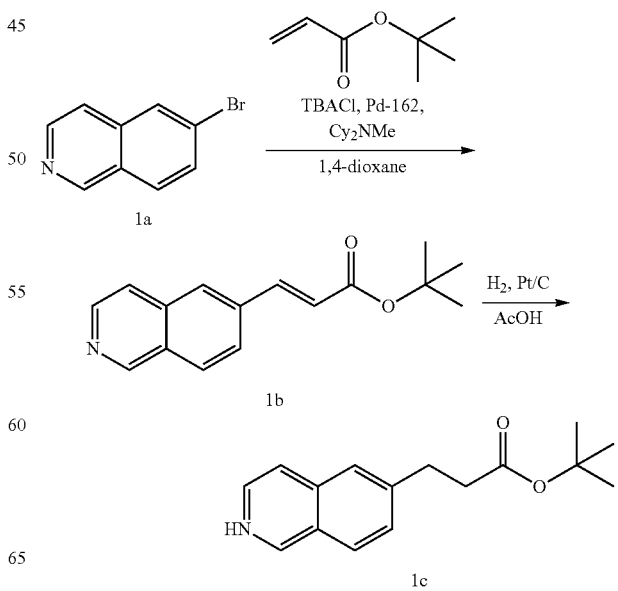

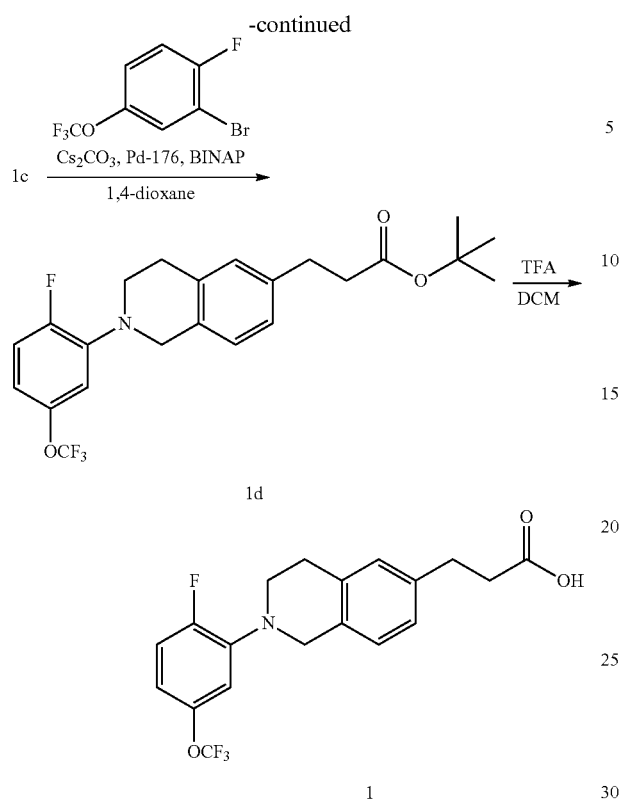

b) Procedure for the Preparation of 1c

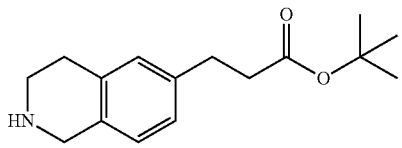

A mixture of (E)-tert-butyl 3-(isoquinolin-6-yl)acrylate 1b (1.1 g, 4.2 mmol) and platinum on carbon (0.82 g, 0.21 mmol) in AcOH (50 mL) was heated at 50° C. under hydrogen (5 Bar) for 2 h. The mixture was cooled to RT, filtered and the solvent concentrated in vacuo. NaOH solution (2 M) was added until pH was >10, then the product was extracted with EtOAc (600 mL). The organic solution was dried over $Na_2SO_4$, filtered and concentrated in vacuo. The product was purified by silica gel chromatography (0-10% (0.7 M Ammonia/MeOH) in DCM) to afford tert-butyl 3-(1,2,3,4-tetrahydroisoquinolin-6-yl)propanoate 1c as a colourless solid: m/z 262 $[M+H]^+$ ($ES^+$). $^1H$ NMR (400 MHz, $CDCl_3$) δ 6.98-6.86 (m, 3H), 3.83 (s, 2H), 2.96 (t, J=5.9 Hz, 2H), 2.73 (t, J=7.5 Hz, 2H), 2.66 (t, J=6.0 Hz, 2H), 2.46 (t, J=7.5 Hz, 2H), 1.37 (s, 9H).

c) Procedure for the Preparation of 1d a) Procedure for the Preparation of 1b

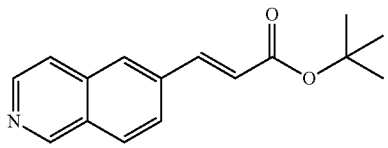 [SMILES: CC(C)(C)OC(=O)/C=C/c1ccc2cnccc2c1]

A mixture of 6-bromoisoquinoline 1a (5.0 g, 24 mmol), tetrabutylammonium chloride hydrate (0.71 g, 2.4 mmol), Pd-162 (0.48 g, 1.2 mmol), tert-butyl acrylate (3.9 mL, 26 mmol) and N-cyclohexyl-N-methylcyclohexanamine (7.7 mL, 36 mmol) in 1,4-dioxane (100 mL) was stirred at 80° C. for 20 h. The mixture was cooled to RT and then concentrated in vacuo. The residue was partitioned between water (100 mL) and DCM (100 mL) and the resultant white precipitate was collected by filtration. The solid was dissolved in a mixture of methanolic ammonia (1M, 100 mL) and DCM (100 mL) and the solution was washed with water (100 mL). Residual product was extracted from the aqueous solution using DCM (300 mL) and the combined organic phases were passed through a hydrophobic membrane and concentrated in vacuo. The product was purified by silica gel chromatography (0-50% EtOAc in isohexane) to afford (E)-tert-butyl 3-(isoquinolin-6-yl)acrylate 1b as a light brown solid: m/z 256 $[M+H]^+$ ($ES^+$). $^1H$ NMR (400 MHz, $CDCl_3$) δ 9.24 (s, J=1.0 Hz, 1H), 8.56 (d, J=5.7 Hz, 1H), 7.97 (dd, J=8.6, 0.8 Hz, 1H), 7.90-7.87 (m, 1H), 7.77 (dd, J=8.6, 1.7 Hz, 1H), 7.73 (d, J=16.1 Hz, 1H), 7.66 (dd, J=5.8, 1.0 Hz, 1H), 6.55 (d, J=16.0 Hz, 1H), 1.56 (s, 9H).

tert-Butyl 3-(1,2,3,4-tetrahydroisoquinolin-6-yl)propanoate 1c (3.0 g, 11 mmol), $Cs_2CO_3$ (6.0 g, 18 mmol), Pd-176 (1.7 g, 2.2 mmol) and BINAP (1.5 g, 2.4 mmol) were placed in a sealed vial which was then evacuated and backfilled with nitrogen three times. A solution of 2-bromo-1-fluoro-4-(trifluoromethoxy)benzene (2 mL, 12 mmol) in 1,4-dioxane (50 mL) was added and the mixture was stirred, under nitrogen at 105° C. After 16 h $Cs_2CO_3$ (6.0 g, 18 mmol) and DMF (6 mL) were added and the mixture was stirred at 115° C. for 3 h and then cooled to RT and filtered. The filtrate was diluted with EtOAc (200 mL) and then washed with 20% NaCl solution (200 mL). The organic solution was dried over $MgSO_4$, filtered and concentrated in vacuo. The product was purified by silica gel chromatography (0-20% EtOAc in isohexane) to afford tert-butyl 3-(2-(2-fluoro-5-(trifluoromethoxy)phenyl)-1,2,3,4-tetrahydroisoquinolin-6-yl)propanoate 1d: m/z 440 $[M+H]^+$ ($ES^+$). $^1H$ NMR (400 MHz, $CDCl_3$) δ 7.08-6.97 (m, 4H), 6.84 (dd, J=7.2, 2.7 Hz, 1H), 6.80-6.72 (m, 1H), 4.28 (s, 2H), 3.46 (t, J=5.8 Hz, 2H), 2.97 (t, J=5.8 Hz, 2H), 2.88 (t, J=7.8 Hz, 2H), 2.53 (t, J=7.8 Hz, 2H), 1.43 (s, 9H).

d) Preparation of Compound 1 3-(2-(2-Fluoro-5-(trifluoromethoxy)phenyl)-1,2,3,4-tetrahydroisoquinolin-6-yl)propanoic Acid

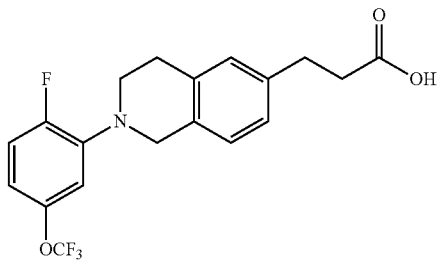

A solution of tert-butyl 3-(2-(2-fluoro-5-(trifluoromethoxy)phenyl)-1,2,3,4-tetrahydroisoquinolin-6-yl)propanoate 1d (3.0 g, 6.8 mmol) in DCM (10 mL) was treated with TFA (6.0 mL, 78 mmol) and the mixture was stirred at RT for 2 h and then concentrated in vacuo. Residual solvents were removed by co-evaporation with toluene (10 mL) and then the product was purified by reverse-phase flash chromatography (15-75% MeCN in Water, 0.1% formic acid, C18) to afford 3-(2-(2-fluoro-5-(trifluoromethoxy)phenyl)-1,2,3,4-tetrahydroisoquinolin-6-yl)propanoic acid 1 as a cream solid: m/z 384 [M+H]$^+$ (ES$^+$), 382 [M−H]$^-$ (ES$^-$). $^1$H NMR (400 MHz, DMSO-$d_6$) δ 12.13 (s, 1H), 7.29 (dd, J=12.5, 8.8 Hz, 1H), 7.13-7.00 (m, 4H), 6.98-6.89 (m, 1H), 4.25 (s, 2H), 3.41 (t, J=5.8 Hz, 2H), 2.89 (t, J=5.8 Hz, 2H), 2.78 (t, J=7.6 Hz, 2H), 2.56-2.51 (m, 2H).

Human GPR12 pEC$_{50}$: 7.4

The following compounds were prepared using appropriate starting materials in analogous procedure to that described in Experimental Scheme 1. Where the starting materials are not described in the literature, their synthesis is described below.

| Compound | Structure | [M + H]+ | NMR | hGPR120 pEC50 |
|---|---|---|---|---|
| 2 | 3-(2-(2-fluoro-5-((1r,3r)-3-methoxycyclobutyloxy)phenyl)-1,2,3,4-tetrahydroisoquinolin-6-yl)propanoic acid | 400 | (DMSO-$d_6$) δ 7.10-7.05 (m, 1H), 7.05-6.97 (m, 3H), 6.48 (dd, J = 7.5, 2.9 Hz, 1H), 6.34 (dt, J = 8.8, 3.1 Hz, 1H), 4.76 (tt, J = 6.9, 4.4 Hz, 1H), 4.19 (s, 2H), 4.04 (tt, J = 6.9, 4.2 Hz, 1H), 3.37-3.34 (m, 2H), 3.16 (s, 3H), 2.84 (t, J = 5.9 Hz, 2H), 2.77 (t, J = 7.6 Hz, 2H), 2.39-2.32 (m, 2H), 2.29-2.19 (m, 2H). | 6.8 |
| 3 | 3-(2-(5-cyclobutoxy-2,3-difluorophenyl)-1,2,3,4-tetrahydroisoquinolin-6-yl)propanoic acid | 388 | (DMSO-$d_6$) δ 12.13 (s, 1H), 7.09 (d, J = 7.9 Hz, 1H), 7.07-6.99 (m, 2H), 6.50-6.42 (m, 1H), 6.30 (dt, J = 6.5, 2.5 Hz, 1H), 4.64 (quint, J = 7.2 Hz, 1H), 4.23 (s, 2H), 3.40 (t, J = 5.9 Hz, 2H), 2.86 (t, J = 5.8 Hz, 2H), 2.78 (t, J = 7.7 Hz, 2H), 2.44-2.30 (m, 2H), 2.05-1.92 (m, 2H), 1.76 (q, J = 10.2 Hz, 1H), 1.68-1.54 (m, 1H). | 8 |
| 4 | 3-(2-(2-phenoxyphenyl)-1,2,3,4-tetrahydroisoquinolin-6-yl)propanoic acid | 374 | (Methanol-$d_4$) δ 7.31-7.24 (m, 2H), 7.19-7.10 (m, 2H), 7.06-6.98 (m, 4H), 6.97-6.88 (m, 4H), 4.23 (s, 2H), 3.42 (t, J = 5.8 Hz, 2H), 2.85 (t, J = 7.7 Hz, 2H), 2.77 (t, J = 5.8 Hz, 2H), 2.56 (t, J = 7.7 Hz, 2H). | 6.8 |

-continued

| Compound | Structure | [M + H]+ | NMR | hGPR120 pEC50 |
|---|---|---|---|---|
| 5 | 3-(2-(2-cyclobutoxypyridin-3-yl)-1,2,3,4-tetrahydroisoquinolin-6-yl)propanoic acid | 353 | (DMSO-$d_6$) δ 7.72 (dd, J = 4.9, 1.6 Hz, 1H), 7.24 (dd, J = 7.7, 1.7 Hz, 1H), 7.04-6.99 (m, 2H), 6.91 (dd, J = 7.6, 4.9 Hz, 1H), 5.9-5.88 (m, 1H), 5.21-5.06 (m, 2H), 4.36 (t, J = 6.4 Hz, 2H), 4.16 (s, 2H), 3.34 (t, J = 5.8 Hz, 2H), 2.85 (t, J = 5.9 Hz, 2H), 2.77 (t, J = 7.7 Hz, 2H), 2.50-2.45 (m, 2H). | 5.1 |
| 6 | 3-(2-(2-cyano-5-(trifluoromethoxy)phenyl)-1,2,3,4-tetrahydroisoquinolin-6-yl)propanoic acid | 391 | (DMSO-$d_6$) δ 12.13 (s, 1H), 7.87 (d, J = 8.6 Hz, 1H), 7.14-7.05 (m, 4H), 7.04-6.97 (m, 1H), 4.40 (s, 2H), 3.63 (t, J = 5.8 Hz, 2H), 2.98 (t, J = 5.8 Hz, 2H), 2.79 (t, J = 7.6 Hz, 2H), 2.57-2.50 (m, 2H). | 7.1 |
| 7 | 3-(2-(6-cyclobutoxy-3-fluoropyridin-2-yl)-1,2,3,4-tetrahydroisoquinolin-6-yl)propanoic acid | 371 | (DMSO-$d_6$) δ 12.12 (s, 1H), 7.43 (dd, J = 12.8, 8.4 Hz, 1H), 7.10 (d, J = 7.8 Hz, 1H), 7.07-6.98 (m, 2H), 6.08 (dd, J = 8.4, 1.7 Hz, 1H), 4.97 (quint, J = 7.3 Hz, 1H), 4.58 (s, 2H), 3.72 (t, J = 5.9 Hz, 2H), 2.87 (t, J = 5.9 Hz, 2H), 2.77 (t, J = 7.6 Hz, 2H), 2.51-2.46 (m, 2H), 2.44-2.31 (m, 2H), 2.10-1.94 (m, 2H), 1.84-1.70 (m, 1H), 1.73-1.57 (m, 1H). | 7.8 |
| 8 | 3-(2-(4-cyclobutoxy-5-fluoropyrimidin-2-yl)-1,2,3,4-tetrahydroisoquinolin-6-yl)propanoic acid | 372 | (DMSO-$d_6$) δ 12.12 (s, 1H), 8.19 (d, J = 3.2 Hz, 1H), 7.14 (d, J = 7.7 Hz, 1H), 7.05 (d, J = 8.3 Hz, 2H), 5.23 (quint, J = 7.7 Hz, 1H), 4.74 (s, 2H), 3.88 (t, J = 5.9 Hz, 2H), 2.82 (t, J = 5.9 Hz, 2H), 2.78 (t, J = 7.6 Hz, 2H), 2.57-2.48 (m, 2H, overlapping with DMSO peak), 2.52-2.40 (m, 2H, overlapping with DMSO peak), 2.23-2.07 (m, 2H), 1.89-1.78 (m, 1H), 1.80-1.63 (m, 1H). | 7.2 |

| Compound | Structure | [M + H]+ | NMR | hGPR120 pEC50 |
|---|---|---|---|---|
| 9 | 3-(2-(2-fluoro-5-phenoxyphenyl)-1,2,3,4-tetrahydroisoquinolin-6-yl)propanoic acid | 392 | (CDCl$_3$) δ 7.35-7.28 (m, 2H), 7.11-7.05 (m, 1H), 7.03-6.94 (m, 6H), 6.72 (dd, J = 7.4, 2.9 Hz, 1H), 6.55-6.49 (m, 1H), 4.24 (s, 2H), 3.43 (t, J = 5.8 Hz, 2H), 3.01-2.88 (m, 4H), 2.67 (t, J = 7.8 Hz, 2H) | 7.7 |

Intermediate 1 (I-1)

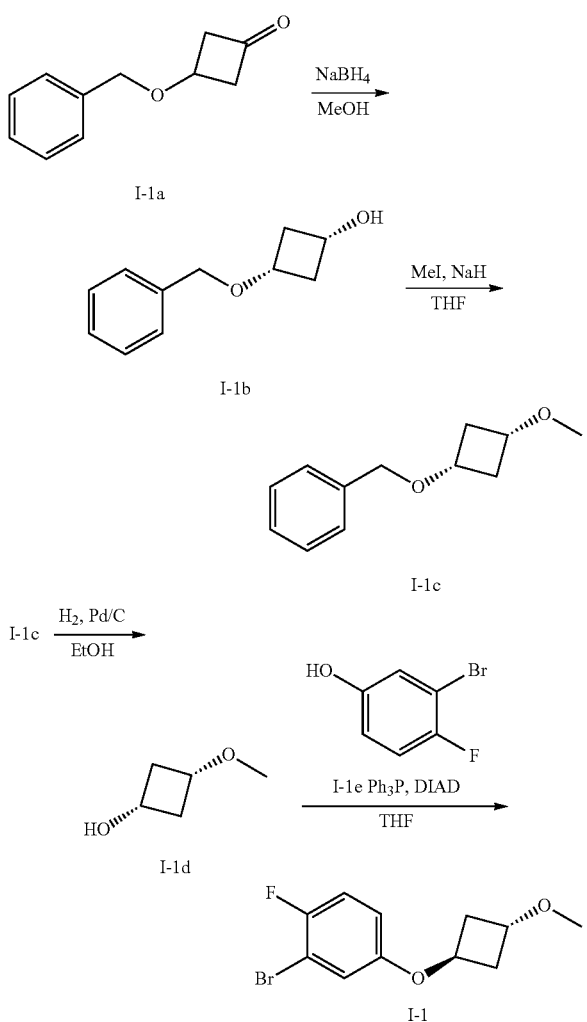

Step 1:

Sodium tetrahydroborate (0.6 g, 16 mmol) was added portionwise to a solution of 3-(benzyloxy)cyclobutanone I-1a (2.8 g, 16 mmol) in MeOH (50 mL) at 0° C. and the mixture was stirred at 0° C. for 3 h. Sat. NaHCO$_3$ solution (70 mL) was added and the product was extracted with EtOAc (300 mL). The organic solution was dried over MgSO$_4$, filtered and concentrated in vacuo. The product was purified by silica gel chromatography (0-50% EtOAc in isohexane) to afford (1s,3s)-3-(benzyloxy)cyclobutanol 1-1b as a colourless oil: $^1$H NMR (400 MHz, CDCl$_3$) δ δ 7.32-7.16 (m, 5H), 4.34 (s, 2H), 3.84 (dtd, J=7.9, 7.2, 6.5 Hz, 1H), 3.56 (tt, J=7.0, 6.2 Hz, 1H), 2.65 (dtd, J=9.4, 6.6, 3.0 Hz, 2H), 1.86 (dtd, J=9.4, 7.6, 2.9 Hz, 2H).

Step 2:

NaH (60% w/w in oil, 0.6 g, 14 mmol) was added to a solution of (1s,3s)-3-(benzyloxy)cyclobutanol I-1b (1.7 g, 9.4 mmol) in THF (30 mL) at 0° C. The mixture was stirred for 15 min before MeI (0.7 mL, 11 mmol) was added. The mixture was stirred at 0° C. for a further 15 min then warmed to RT and stirred for 16 h. Sat. NaHCO$_3$ solution (100 mL) was added and the product was extracted with DCM (300 mL). The combined organic phases were dried over Na$_2$SO$_4$, filtered and concentrated in vacuo. The product was purified by silica gel chromatography (0-50% EtOAc in isohexane) to afford (((1s,3s)-3-methoxycyclobutoxy)methyl)benzene I-1c as a colourless oil: m/z 193 [M+H]$^+$ (ES$^+$). $^1$H NMR (400 MHz, CDCl$_3$) δ δ 7.31-7.16 (m, 5H), 4.35 (s, 2H), 3.66-3.56 (m, 1H), 3.48-3.39 (m, 1H), 3.16 (s, 3H), 2.61-2.51 (m, 2H), 1.92-1.81 (m, 2H).

Step 3:

A mixture of (((1s,3s)-3-methoxycyclobutoxy)methyl)benzene 1-1c (1.4 g, 7.3 mmol) and Pd/C (JM Type 39, 10%, 50% w/w) (0.155 g, 0.073 mmol) in EtOH (50 mL) was stirred at RT under an atmosphere of hydrogen (5 Bar) for 16 h. The reaction mixture was filtered through a pad of celite and the filtrate was concentrated in vacuo. The product was purified by silica gel chromatography (0-60% EtOAc in isohexane) to afford (1s,3s)-3-methoxycyclobutanol I-1d as a yellow oil: $^1$H NMR (400 MHz, CDCl$_3$) δ 3.92 (quint, J=7.2 Hz, 1H), 3.46 (quint, J=6.8 Hz, 1H), 3.23 (s, 3H), 2.79-2.64 (m, 2H), 2.01 (s, 1H), 1.91-1.79 (m, 2H).

Step 4:

A mixture of (1s,3s)-3-methoxycyclobutanol I-1d (0.15 g, 1.5 mmol), 3-bromo-4-fluorophenol I-1e (0.28 g, 1.5 mmol), Ph$_3$P (0.39 g, 1.5 mmol) and DIAD (0.286 ml, 1.469 mmol) in THF (20 mL) was heated at 80° C. for 2 days. The reaction mixture was cooled to RT and concentrated in vacuo. The product was purified by silica gel chromatography (0-20% EtOAc in isohexane) to afford 2-bromo-1-fluoro-4-(((1r,3r)-3-methoxycyclobutoxy)benzene I-1 as a colourless oil: $^1$H NMR (400 MHz, CDCl$_3$) δ 6.95 (dd, J=9.0, 8.1 Hz, 1H), 6.88 (dd, J=5.6, 3.0 Hz, 1H), 6.62 (ddd, J=9.0, 3.8, 3.0 Hz, 1H), 4.69 (tt, J=6.7, 4.5 Hz, 1H), 4.05 (tt, J=6.8, 4.5 Hz, 1H), 3.20 (s, 3H), 2.45-2.25 (m, 4H).

Intermediate 2 (I-2)

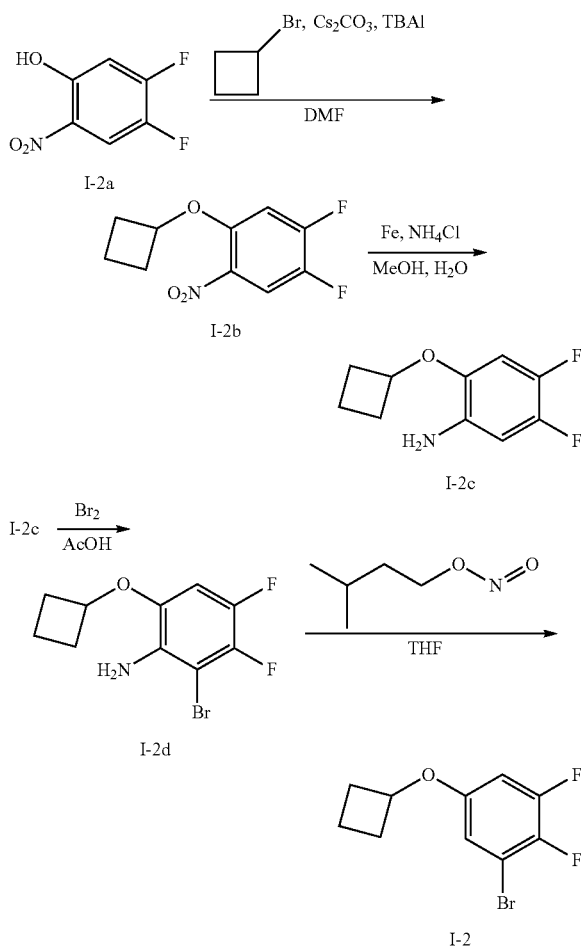

Step 1:
A mixture of 4,5-difluoro-2-nitrophenol I-2a (2.2 g, 13 mmol), bromocyclobutane (2.4 mL, 25 mmol), TBAI (4.7 g, 13 mmol) and $Cs_2CO_3$ (4.1 g, 13 mmol) in DMF (10 mL) was stirred at 90° C. for 16 h. The mixture was cooled to RT, diluted with water (100 mL) and the product was extracted with TBME (300 mL). The organic solution was washed with brine (50 mL) and dried over $Na_2SO_4$, filtered and concentrated in vacuo. The product was purified by silica gel chromatography (0-10% EtOAc in isohexane) to afford 1-cyclobutoxy-4,5-difluoro-2-nitrobenzene I-2b as a light yellow solid: $^1$H NMR (400 MHz, $CDCl_3$) δ 7.83 (dd, J=9.6, 8.1 Hz, 1H), 6.74 (dd, J=11.5, 6.5 Hz, 1H), 4.69 (quint, J=7.5 Hz, 1H), 2.56-2.42 (m, 2H), 2.36-2.21 (m, 2H), 2.01-1.86 (m, 1H), 1.81-1.66 (m, 1H).

Step 2:
A mixture of 1-cyclobutoxy-4,5-difluoro-2-nitrobenzene I-2b (1.3 g, 5.6 mmol), $NH_4Cl$ (3.0 g, 56 mmol) and iron (1.6 g, 28 mmol) in MeOH (30 mL) was stirred at 90° C. for 1 h, then cooled to RT and filtered through a pad of celite. The filtrate was concentrated in vacuo and the residue was partitioned between EtOAc (50 mL) and water (50 mL). Residual product was extracted from the aqueous solution with EtOAc (100 mL). The combined organic phases were dried over $Na_2SO_4$, filtered and concentrated in vacuo. The product was purified by silica gel chromatography (0-100% EtOAc in isohexane) to afford 2-cyclobutoxy-4,5-difluoroaniline I-2c as a red oil: m/z 200 $[M+H]^+$ ($ES^+$). $^1$H NMR (400 MHz, $CDCl_3$) δ δ 6.53-6.42 (m, 2H), 4.61-4.49 (m, 1H), 3.74-3.63 (m, 2H), 2.50-2.37 (m, 2H), 2.24-2.10 (m, 2H), 1.92-1.80 (m, 1H), 1.76-1.61 (m, 1H).

Step 3:
$Br_2$ (0.3 mL, 6 mmol) was added dropwise to a solution of 2-cyclobutoxy-4,5-difluoroaniline I-2c (1.0 g, 5 mmol) in AcOH (35 mL). The reaction was stirred at RT for 16 h and then sat. $Na_2S_2O_3$ solution (50 mL) was added. The product was extracted with EtOAc (125 mL) and the organic solution was dried over $Na_2SO_4$, filtered and concentrated in vacuo. The product was purified by silica gel chromatography (0-10% EtOAc in isohexane) to afford 2-bromo-6-cyclobutoxy-3,4-difluoroaniline I-2d as a yellow solid: m/z 278 $[M+H]^+$ ($ES^+$). $^1$H NMR (400 MHz, $CDCl_3$) δ 6.49 (dd, J=11.4, 7.1 Hz, 1H), 4.57 (quint, J=7.1 Hz, 1H), 4.11 (s, 2H), 2.52-2.39 (m, 2H), 2.25-2.11 (m, 2H), 1.95-1.83 (m, 1H), 1.78-1.61 (m, 1H).

Step 4:
Isoamyl nitrite (0.73 mL, 5.4 mmol) was added to a solution of 2-bromo-6-cyclobutoxy-3,4-difluoroaniline I-2d (0.75 g, 2.7 mmol) in THF (10 mL) and the mixture was stirred at 70° C. for 16 h and then cooled to RT. Water (50 mL) was added and the product was extracted with DCM (150 mL). The organic solution was passed through a hydrophobic membrane and then concentrated in vacuo. The product was purified by silica gel chromatography (0-10% EtOAc in isohexane) to afford 1-bromo-5-cyclobutoxy-2,3-difluorobenzene I-2 as a colourless oil: $^1$H NMR (400 MHz, $CDCl_3$) δ 6.74 (ddd, J=4.9, 3.0, 2.2 Hz, 1H), 6.59 (ddd, J=11.5, 6.1, 3.0 Hz, 1H), 4.60-4.49 (m, 1H), 2.50-2.37 (m, 2H), 2.21-2.07 (m, 2H), 1.94-1.81 (m, 1H), 1.76-1.61 (m, 1H).

Intermediate 3 (I-3)

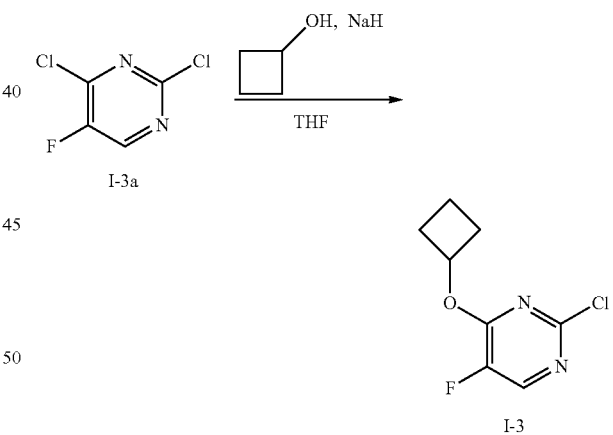

A solution of cyclobutanol (125 μL, 1.60 mmol) in dry THF (1 mL) was added dropwise to a suspension of NaH (60% w/w in oil, 65 mg, 1.6 mmol) in dry THF (5 mL) under nitrogen. The mixture was stirred at RT for 10 min before a solution of 2,4-dichloro-5-fluoropyrimidine I-3a (250 mg, 1.5 mmol) in THF (1 mL) was added dropwise. The reaction mixture was stirred at RT for 16 h then partitioned between sat. aq. $NH_4Cl$ (50 mL) and EtOAc (100 mL). The organic solution was dried over $MgSO_4$, filtered and concentrated in vacuo. The residue was purified by silica gel chromatography (0-10% EtOAc in isohexane) to afford 2-chloro-4-cyclobutoxy-5-fluoropyrimidine I-3 as a colourless oil: $^1$H NMR (400 MHz, $CDCl_3$) δ 8.19 (d, J=2.3 Hz, 1H), 5.41-

5.28 (m, 1H), 2.60-2.44 (m, 2H), 2.35-2.16 (m, 2H), 1.99-1.85 (m, 1H), 1.82-1.65 (m, 1H).

Intermediate 4 (I-4)

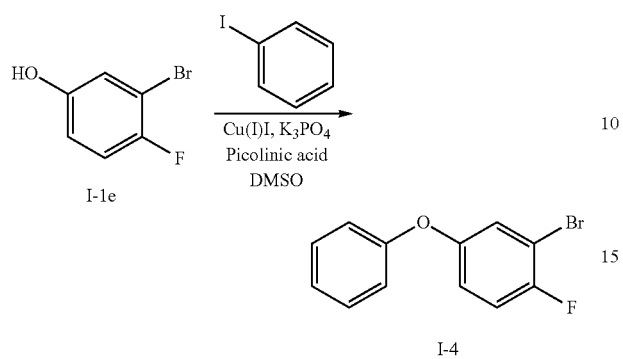

A vial was charged with 3-bromo-4-fluorophenol I-1e (300 mg, 1.57 mmol), copper(I) iodide (30 mg, 0.157 mmol), 2-picolinic acid (39 mg, 0.314 mmol), anhydrous potassium phosphate tribasic (0.67 g, 3.14 mmol) and anhydrous DMSO (3.1 mL). The vial was evacuated and back filled with argon (4×). Iodobenzene (641 mg, 3.14 mmol) was added and the mixture was heated at 90° C. for 36 h. The reaction mixture was cooled to RT, diluted with 2 mL water and the product was extracted with EtOAc (4×). The combined organic phases were washed with brine, dried with $Na_2SO_4$, filtered and concentrated under vacuo. The residue was purified by chromatography on silica (petroleum ether) to afford 2-bromo-1-fluoro-4-phenoxybenzene as a colourless oil: $^1$H NMR (400 MHz, $CDCl_3$) δ δ 7.39-7.33 (m, 2H), 7.19 (dd, J=5.7, 2.9 Hz, 1H), 7.16-7.11 (m, 1H), 7.11-7.06 (m, 1H), 7.01-6.97 (m, 2H), 6.96-6.90 (m, 1H).

Experimental Scheme 2

Compound 10 3-(2-(3-(Trifluoromethoxy)phenyl)-1,2,3,4-tetrahydroisoquinolin-6-yl)propanoic Acid

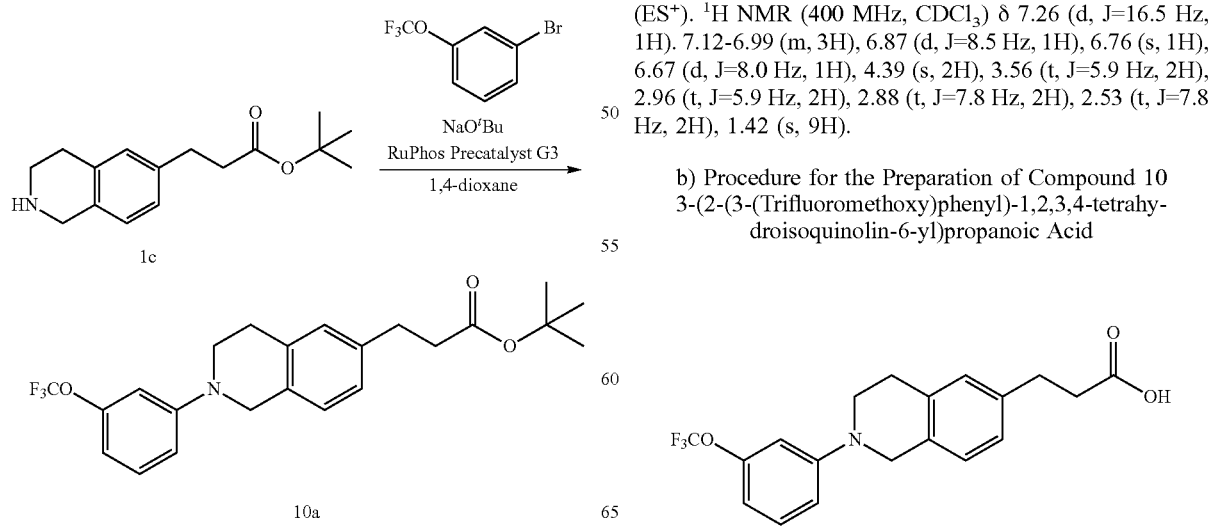

a) Procedure for the Preparation of 10a tert-Butyl 3-(1,2,3,4-tetrahydroisoquinolin-6-yl)propanoate 1c (100 mg, 0.4 mmol), NaO$^t$Bu (60 mg, 0.62 mmol), 1-bromo-3-(trifluoromethoxy)benzene (100 mg, 0.4 mmol) and RuPhos precatalyst G3 (10 mg, 12 μmol) were placed in a sealed vial which was then evacuated and backfilled with nitrogen three times. 1,4-Dioxane (2 mL) was added and the vial was again evacuated and backfilled with nitrogen three times. The mixture was stirred, under nitrogen at 85° C. for 30 min and then cooled to RT and AcOH (50 μL, 0.9 mmol) was added. The mixture was diluted with sat. aq. NH$_4$Cl (5 mL) and the product was extracted with EtOAc (5 mL). The organic solution was dried over MgSO$_4$, filtered and concentrated in vacuo. The product was purified by silica gel chromatography (0-50% EtOAc in isohexane) to afford tert-butyl 3-(2-(3-(trifluoromethoxy)phenyl)-1,2,3,4-tetrahydroisoquinolin-6-yl)propanoate 10a: m/z 422 [M+H]$^+$ (ES$^+$). $^1$H NMR (400 MHz, CDCl$_3$) δ 7.26 (d, J=16.5 Hz, 1H). 7.12-6.99 (m, 3H), 6.87 (d, J=8.5 Hz, 1H), 6.76 (s, 1H), 6.67 (d, J=8.0 Hz, 1H), 4.39 (s, 2H), 3.56 (t, J=5.9 Hz, 2H), 2.96 (t, J=5.9 Hz, 2H), 2.88 (t, J=7.8 Hz, 2H), 2.53 (t, J=7.8 Hz, 2H), 1.42 (s, 9H).

b) Procedure for the Preparation of Compound 10 3-(2-(3-(Trifluoromethoxy)phenyl)-1,2,3,4-tetrahydroisoquinolin-6-yl)propanoic Acid A solution of tert-butyl 3-(2-(3-(trifluoromethoxy)phenyl)-1,2,3,4-tetrahydroisoquinolin-6-yl)propanoate 10a (60 mg, 0.14 mmol) in DCM (200 μL) was treated with TFA (100 μL, 0.14 mmol) and the mixture was stirred at RT for 2 h and then concentrated in vacuo. Residual solvents were removed by co-evaporation with 10% (7N $NH_3$ in MeOH) in DCM and then the product was purified by silica gel chromatography (0-50% EtOAc in isohexane) to afford 3-(2-(3-(trifluoromethoxy)phenyl)-1,2,3,4-tetrahydroisoquinolin-6-yl)propanoic acid 10 as a white solid: m/z 366 [M+H]$^+$ (ES$^+$). $^1$H NMR (400 MHz, DMSO-d$_6$) 12.15 (s, 1H), 7.31 (t, J=8.3 Hz, 1H), 7.15 (d, J=7.9 Hz, 1H), 7.09-7.02 (m, 2H), 6.98 (dd, J=8.5, 2.5 Hz, 1H), 6.87 (s, 1H), 6.65 (d, J=7.8 Hz, 1H), 4.39 (s, 2H), 3.55 (t, J=5.9 Hz, 2H), 2.87 (t, J=5.9 Hz, 2H), 2.78 (t, J=7.6 Hz, 2H), 2.56-2.51 (m, 2H).

Human GPR120 pEC$_{50}$: 6.8

The following compounds were prepared using appropriate starting materials in an analogous procedure to that described in Experimental Scheme 2. Where the starting materials are not described in the literature, their synthesis is described below.

| Example | Structure | [M + H]+ | NMR | hGPR120 pEC50 |
|---|---|---|---|---|
| 11 | 3-(2-(2-chloro-5-cyclobutoxyphenyl)-1,2,3,4-tetrahydroisoquinolin-6-yl)propanoic acid | 386 | (CDCl$_3$) δ 7.17 (d, J = 8.7, 1H), 6.99-6.92 (m, 3 H), 6.53 (d, J 2.8, 1 H), 6.35 (dd, J 8.7, 2.8, 1H), 4.59-4.44 (m, 1 H), 4.14 (s, 2 H), 3.30 (t, J 5.8, 2 H), 2.92 (t, J 5.8, 2 H), 2.86 (t, J 7.8, 2 H), 2.61 (dd, J 8.4, 7.2, 2 H), 2.38-2.24 (m, 2 H), 2.07 (dtd, J 12.6, 10.0, 7.9, 2 H). | 7.3 |
| 12 | 3-(2-(3-cyclobutoxyphenyl)-1,2,3,4-tetrahydroisoquinolin-6-yl)propanoic acid | 352 | (CDCl$_3$) δ 7.08 (t, J 8.2, 1 H), 7.03-6.90 (m, 3 H), 6.49 (ddd, J 8.3, 2.4, 0.8, 1 H), 6.37 (t, J 2.4, 1 H), 6.20 (ddd, J 8.1, 2.3, 0.8, 1 H), 4.63-4.46 (m, 1 H), 4.29 (s, 2 H), 3.45 (t, J 5.9, 2 H), 2.90-2.81 (m, 4 H), 2.60 (dd, J 8.4, 7.2, 2 H), 2.44-2.27 (m, 2 H), 2.10 (dtd, J 12.6, 10.0, 7.9, 2 H) | 6.8 |
| 13 | 3-(2-(5-cyclobutoxy-2-fluorophenyl)-1,2,3,4-tetrahydroisoquinolin-6-yl)propanoic acid | 370 | (CDCl$_3$) δ 6.97-6.90 (m, 3 H), 6.85 (dd, J 12.2, 8.8, 1 H), 6.42 (dd, J 7.4, 2.9, 1 H), 6.23 (dt, J 8.8, 3.1, 1 H), 4.54-4.40 (m, 1 H), 4.18 (s, 2 H), 3.35 (t, J 5.8, 2 H), 2.92-2.78 (m, 4 H), 2.61 (dd, J 8.4, 7.2, 2 H), 2.33 (dddt, J 9.5, 8.1, 6.8, 2.7, 2 H), 2.15-1.99 (m, 2 H), 1.83-1.69 (m, 1 H), 1.66-1.51 (m, 1 H). | 7.7 |
| 14 | 3-(2-(5-cyclobutoxy-2-methylphenyl)-1,2,3,4-tetrahydroisoquinolin-6-yl)propanoic acid | 366 | (DMSO-d$_6$) δ 12.13 (s, 1H), 7.09-6.98 (m, 4H), 6.55 (d, J = 2.5 Hz, 1H), 6.44 (dd, J = 8.2, 2.5 Hz, 1H), 4.62 (quint, J = 7.1 Hz, 1H), 4.00 (s, 2H), 3.11 (t, J = 5.8 Hz, 2H), 2.87 (t, J = 5.8 Hz, 2H), 2.78 (t, J = 7.6 Hz, 2H), 2.56-2.52 (m, 2H), 2.44-2.32 (m, 2H), 2.17 (s, 3H), 2.11-1.93 (m, 2H), 1.82-1.70 (m, 1H), 1.70-1.55 (m, 1H). | 7.3 |

-continued

| Example | Structure | [M + H]+ | NMR | hGPR120 pEC50 |
|---|---|---|---|---|
| 15 | 3-(2-(5-chloro-2,2-dimethyl-2,3-dihydrobenzofuran-7-yl)-1,2,3,4-tetrahydroisoquinolin-6-yl)propanoic acid | 386 | (DMSO-d$_6$) δ 7.06 (d, J = 7.9 Hz, 1H), 7.03 (s, 1H), 7.00 (d, J = 7.8 Hz, 1H), 6.81 (d, J = 2.1 Hz, 1H), 6.69 (d, J = 2.2 Hz, 1H), 4.21 (s, 2H), 3.42 (t, J = 5.8 Hz, 2H), 2.99 (s, 2H), 2.82 (t, J = 5.7 Hz, 2H), 2.77 (t, J = 7.7 Hz, 2H), 1.44 (s, 6H). | 6.2 |
| 16 | 3-(2-(3-(trifluoromethyl)phenyl)-1,2,3,4-tetrahydroisoquinolin-6-yl)propanoic acid | 350 | (DMSO-d$_6$) δ 12.11 (s, 1H), 7.43 (td, J = 8.0, 7.5, 0.9 Hz, 1H), 7.26 (dd, J = 8.4, 2.6 Hz, 1H), 7.21-7.12 (m, 2H), 7.10-6.96 (m, 3H), 4.43 (s, 2H), 3.59 (t, J = 5.9 Hz, 2H), 2.89 (t, J = 5.9 Hz, 2H), 2.78 (t, J = 7.6 Hz, 2H), 2.54-2.50 (m, 2H). | 6.3 |
| 17 | 3-(2-(4-cyanophenyl)-1,2,3,4-tetrahydroisoquinolin-6-yl)propanoic acid | 307 | (DMSO-d$_6$) δ 7.62-7.57 (m, 2H), 7.16 (d, J = 8.4 Hz, 1H), 7.09-7.00 (m, 4H), 4.50 (s, 2H), 3.63 (t, J = 5.9 Hz, 2H), 2.89 (t, J = 5.9 Hz, 2H), 2.79 (t, J = 7.6 Hz, 2H). | 5.1 |
| 18 | 3-(2-(2-cyclopropylpyrimidin-4-yl)-1,2,3,4-tetrahydroisoquinolin-6-yl)propanoic acid | 324 | (DMSO-d$_6$) δ 12.19 (s, 1H), 8.16 (d, J = 6.2 Hz, 1H), 7.27-7.21 (m, 1H), 7.16 (d, J = 7.0 Hz, 2H), 6.72 (d, J = 6.3 Hz, 1H), 4.77 (s, 2H), 3.89 (s, 2H), 2.96-2.82 (m, 4H), 2.06 (tt, J = 7.9, 4.9 Hz, 1H), 1.10-0.95 (m, 4H). | 4.6 |

| Example | Structure | [M + H]+ | NMR | hGPR120 pEC50 |
|---|---|---|---|---|
| 19 | 3-(2-(3-cyclobutoxy-5-fluorophenyl)-1,2,3,4-tetrahydroisoquinolin-6-yl)propanoic acid | 370 | (CDCl₃) δ 7.10-7.00 (m, 3H), 6.23 (dt, J = 12.2, 2.2 Hz, 1H), 6.17 (t, J = 1.8 Hz, 1H), 5.97 (dt, J = 10.5, 2.1 Hz, 1H), 4.65-4.56 (m, 1H), 4.35 (s, 2H), 3.50 (t, J = 5.9 Hz, 2H), 2.96-2.90 (m, 4H), 2.68 (t, J = 7.8 Hz, 2H), 2.49-2.39 (m, 2H), 2.22-2.10 (m, 2H), 1.91-1.80 (m, 1H), 1.75-1.62 (m, 1H) | 7.6 |
| 20 | 3-(2-(3-phenoxyphenyl)-1,2,3,4-tetrahydroisoquinolin-6-yl)propanoic acid | 374 | (DMSO-d₆) δ 12.14 (s, 1H), 7.41-7.32 (m, 2H), 7.21 (t, J = 8.2 Hz, 1H), 7.15-7.08 (m, 2H), 7.04 (d, J = 6.8 Hz, 2H), 7.01-6.96 (m, 2H), 6.81-6.75 (m, 1H), 6.66 (t, J = 2.3 Hz, 1H), 6.30 (ddd, J = 8.0, 2.2, 0.8 Hz, 1H), 4.34 (s, 2H), 3.51 (t, J = 5.9 Hz, 2H), 2.86 (t, J = 5.9 Hz, 2H), 2.78 (t, J = 7.6 Hz, 2H). | 7.6 |
| 21 | 3-(2-(6-cyclobutoxypyridin-2-yl)-1,2,3,4-tetrahydroisoquinolin-6-yl)propanoic acid | 353 | (DMSO-d₆) δ 12.11 (s, 1H), 7.49-7.40 (m, 1H), 7.14 (d, J = 7.7 Hz, 1H), 7.08-6.99 (m, 2H), 6.33 (dd, J = 8.0, 3.9 Hz, 1H), 5.96 (d, J = 7.8 Hz, 1H), 5.11-5.00 (m, 1H), 4.58 (s, 2H), 3.76 (t, J = 5.8 Hz, 2H), 2.84 (t, J = 5.9 Hz, 2H), 2.78 (t, J = 7.6 Hz, 2H), 2.41 (dddt, J = 9.5, 7.9, 6.9, 2.6 Hz, 2H), 2.10-1.96 (m, 2H), 1.85-1.72 (m, 1H), 1.72-1.59 (m, 1H). | 7.4 |
| 22 | 3-(2-(6-(trifluoromethoxy)pyridin-2-yl)-1,2,3,4-tetrahydroisoquinolin-6-yl)propanoic acid | 367 | (DMSO-d₆) δ 12.11 (s, 1H), 7.71 (dd, J = 8.4, 7.6 Hz, 1H), 7.14 (d, J = 8.4 Hz, 1H), 7.06 (d, J = 6.8 Hz, 2H), 6.80 (d, J = 8.4 Hz, 1H), 6.38 (d, J = 7.6 Hz, 1H), 4.61 (s, 2H), 3.77 (t, J = 5.9 Hz, 2H), 2.86 (t, J = 5.9 Hz, 2H), 2.78 (t, J = 7.6 Hz, 2H). | 6.5 |
| 23 | 3-(2-([1,1'-biphenyl-3-yl)-1,2,3,4-tetrahydroisoquinolin-6-yl)propanoic acid | 358 | (DMSO-d₆) δ 12.12 (s, 1H), 7.72-7.63 (m, 2H), 7.50-7.42 (m, 2H), 7.40-7.34 (m, 1H), 7.31 (t, J = 7.9 Hz, 1H), 7.20 (t, J = 2.1 Hz, 1H), 7.18-7.13 (m, 1H), 7.07-6.97 (m, 4H), 4.43 (s, 2H), 3.60 (t, J = 5.9 Hz, 2H), 2.91 (t, J = 5.9 Hz, 2H), 2.78 (t, J = 7.6 Hz, 2H). | 6.4 |

| Example | Structure | [M + H]+ | NMR | hGPR120 pEC50 |
|---|---|---|---|---|
| 24 | 3-(2-(5-fluoro-[1,1'-biphenyl-3-yl)-1,2,3,4-tetrahydroisoquinolin-6-yl)propanoic acid | 376 | (DMSO-$d_6$) δ 12.11 (s, 1H), 7.72-7.67 (m, 2H), 7.51-7.43 (m, 2H), 7.43-7.34 (m, 1H), 7.17 (d, J = 8.3 Hz, 1H), 7.08-7.04 (m, 2H), 7.02 (t, J = 1.9 Hz, 1H), 6.83-6.79 (m, 1H), 6.77 (d, J = 1.8 Hz, 1H), 4.46 (s, 2H), 3.62 (t, J = 5.9 Hz, 2H), 2.90 (t, J = 5.9 Hz, 2H), 2.79 (t, J = 7.6 Hz, 2H). | 6.4 |
| 25 | 3-(2-(3-methoxy-5-(trifluoromethoxy)phenyl)-1,2,3,4-tetrahydroisoquinolin-6-yl)propanoic acid | 396 | (DMSO-$d_6$) δ 12.13 (s, 1H), 7.15 (d, J = 8.4 Hz, 1H), 7.05 (d, J = 6.6 Hz, 2H), 6.49 (d, J = 2.1 Hz, 2H), 6.25 (d, J = 1.1 Hz, 1H), 4.38 (s, 2H), 3.77 (s, 3H), 3.54 (t, J = 5.9 Hz, 2H), 2.87 (t, J = 5.8 Hz, 2H), 2.78 (t, J = 7.6 Hz, 2H), 2.57-2.52 (m, 2H, overlapping with DMSO peak) | 7.2 |

Intermediate 5 (I-5)

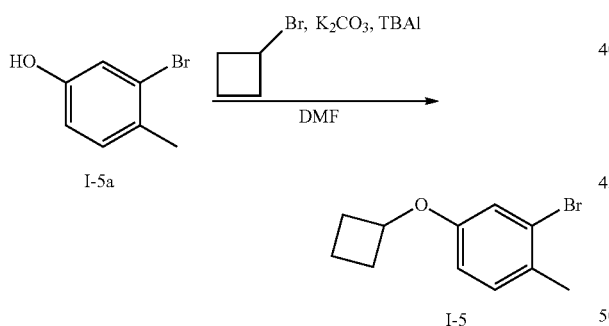

Intermediate 6 (I-6)

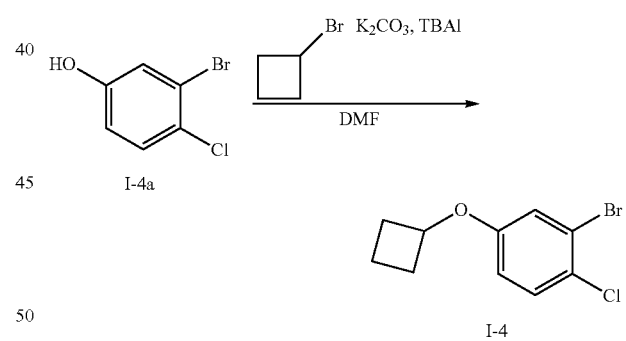

A mixture of solution of 3-bromo-4-methylphenol I-5a (250 mg, 1.3 mmol), $K_2CO_3$ (380 mg, 2.8 mmol), KI (10 mg, 60 μmol) and bromocyclobutane (0.2 mL, 2 mmol) in DMF (3 ml) was stirred at 95° C. for 16 h, then cooled to RT and 20% w/w NaCl solution (50 mL) was added. The product was extracted with EtOAc (20 mL), the organic solution was dried over $MgSO_4$, filtered and concentrated in vacuo. The product was purified by silica gel chromatography (0-10% EtOAc in isohexane) to afford 2-bromo-4-cyclobutoxy-1-methylbenzene I-5 as a colourless oil: $^1$H NMR (400 MHz, $CDCl_3$) δ 7.12 (dd, J=8.4, 0.8 Hz, 1H), 7.02 (d, J=2.6 Hz, 1H), 6.70 (dd, J=8.4, 2.6 Hz, 1H), 4.66-4.54 (m, 1H), 2.52-2.39 (m, 2H), 2.33 (d, J=0.6 Hz, 3H), 2.24-2.08 (m, 2H), 1.94-1.80 (m, 1H), 1.78-1.61 (m, 1H).

A mixture of solution of 3-bromo-4-chlorophenol I-4a (0.3 g, 1.446 mmol), $K_2CO_3$ (0.50 g, 3.6 mmol) and bromocyclobutane (0.16 mL, 1.7 mmol) in DMF (5 ml) was stirred at 100° C. for 16 h, then cooled to RT and sat. $NaHCO_3$ solution (15 mL) was added. The product was extracted with MTBE (90 mL), the organic solution was dried over $Na_2SO_4$, filtered and concentrated in vacuo. The product was purified by silica gel chromatography (0-10% EtOAc in isohexane) to afford 2-bromo-1-chloro-4-cyclobutoxybenzene I-4 as a colourless oil: $^1$H NMR (400 MHz, $CDCl_3$) δ 7.31-7.21 (m, 1H), 7.03 (d, J=2.8 Hz, 1H), 6.68 (dd, J=8.9, 2.9 Hz, 1H), 4.61-4.50 (m, 1H), 2.47-2.35 (m, 2H), 2.19-2.05 (m, 2H), 1.90-1.78 (m, 1H), 1.74-1.59 (m, 1H).

Experimental Scheme 3

Compound 26 3-(2-(2-Fluoro-5-(trifluoromethoxy)phenyl)-1,2,3,4-tetrahydroisoquinolin-6-yl)-2-methylpropanoic Acid

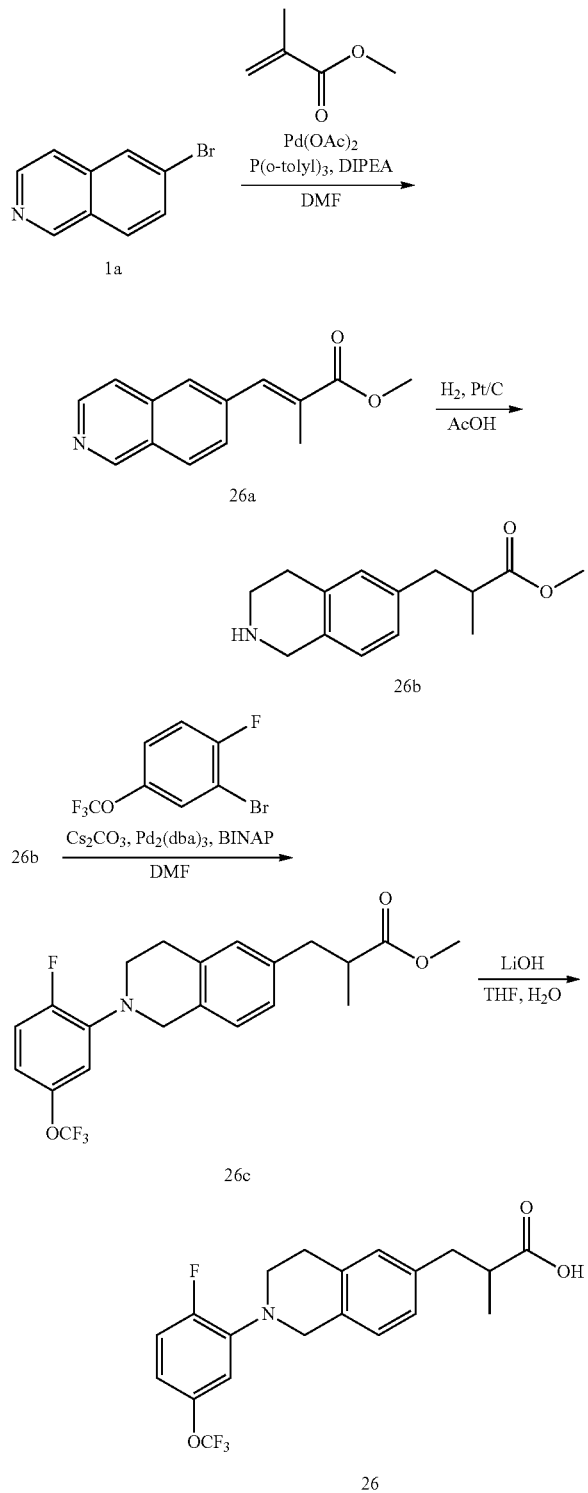

a) Procedure for the Preparation of 26a

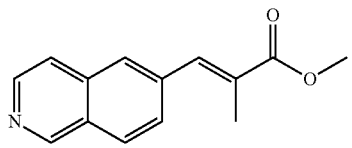 [SMILES: COC(=O)/C(C)=C/c1ccc2cnccc2c1]

A flask was charged with 6-bromoisoquinoline 1a (500 mg, 2.4 mmol), Pd(OAc)$_2$ (22 mg, 0.10 mmol), tri(o-tolyl)phosphine (52 mg, 0.17 mmol), DIPEA (0.84 mL, 4.8 mmol) and DMF (4.8 mL). The flask was evacuated and backfilled with argon three times before the addition of methyl methacrylate (0.5 mL, 0.2 mmol). The mixture was stirred at 80° C. for 2.5 h and then cooled to RT, diluted with EtOAc and filtered. The filtrate was diluted with water and extracted with EtOAc (×3). The combined organic phases were washed with brine, dried over Na$_2$SO$_4$, filtered and concentrated in vacuo onto celite. Purification by silica gel chromatography (25-50% EtOAc in pet. ether) afforded a mixture of methyl 3-(isoquinolin-6-yl)-2-methylacrylate 26a (contaminated with the minor isomer methyl 2-(isoquinolin-6-ylmethyl)acrylate) as a yellow oil that was used in the next step without further purification: $^1$H NMR (400 MHz, CDCl$_3$) δ 9.25 (s, 1H), 8.55 (d, J=5.8 Hz, 1H), 7.96 (d, J=8.5 Hz, 1H), 7.80 (d, J=12.1 Hz, 2H), 7.67-7.56 (m, 2H), 3.86 (s, 3H), 2.18 (d, J=1.5 Hz, 3H); ESI-HRMS calculated for C$_{14}$H$_{14}$NO$_2$ (M+H$^+$) 228.1019, found 228.1024.

b) Procedure for the Preparation of 26b

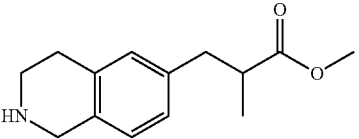 [SMILES: COC(=O)C(C)Cc1ccc2c(c1)CCNC2]

A mixture of methyl 3-(isoquinolin-6-yl)-2-methylacrylate and methyl 2-(isoquinolin-6-ylmethyl)acrylate 26a (278 mg, 1.22 mmol) and 5% Pt/C (239.2 mg, 61 μmol Pt) in AcOH (12 mL) was heated at 50° C. under an atmosphere of H$_2$. After 22 h the mixture was cooled to RT and filtered through a plug of celite, washing through with EtOAc. The filtrate was concentrated in vacuo and the oil was partitioned between EtOAc and sat. Na$_2$CO$_3$ (30 mL). The organic solution was washed with brine, dried over Na$_2$SO$_4$, filtered and concentrated in vacuo. The residue was dissolved in DCM and concentrated in vacuo to give methyl 2-methyl-3-(1,2,3,4-tetrahydroisoquinolin-6-yl)propanoate 26b as a yellow oil that was used without further purification: $^1$H NMR (400 MHz, CDCl$_3$) δ 6.93-6.91 (m, 2H), 6.88 (s, 1H), 3.98 (s, 2H), 3.65 (s, 3H), 3.12 (t, J=6.0 Hz, 2H), 3.01-2.93 (m, 1H), 2.76 (t, J=5.8 Hz, 2H), 2.75-2.66 (m, 1H), 2.59 (dd, J=13.3, 7.8 Hz, 1H), 1.14 (d, J=6.9 Hz, 3H); ESI-HRMS calculated for C$_{14}$H$_{20}$NO$_2$ (M+H$^+$) 234.1489, found 234.1494.

c) Procedure for the Preparation of 26c d) Procedure for the Preparation of Compound 26
3-(2-(2-Fluoro-5-(trifluoromethoxy)phenyl)-1,2,3,4-tetrahydroisoquinolin-6-yl)-2-methylpropanoic Acid

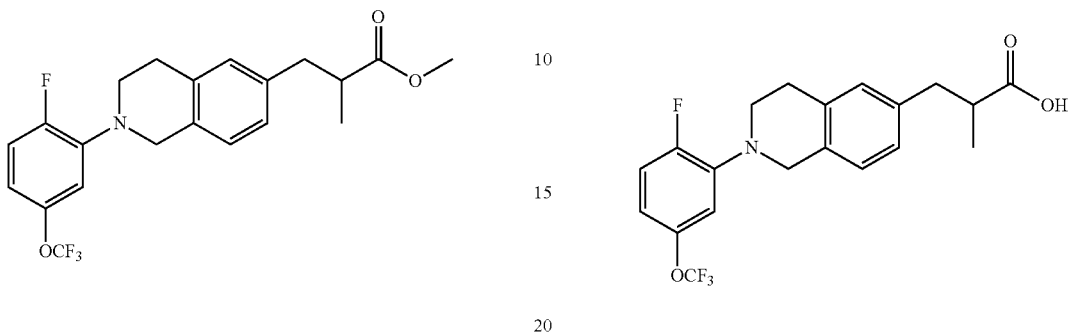

Methyl 2-methyl-3-(1,2,3,4-tetrahydroisoquinolin-6-yl)propanoate 26b (110 mg, 0.48 mmol), Cs$_2$CO$_3$ (310 mg, 0.96 mmol), Pd$_2$(dba)$_3$ (45 mg, 49 μmol), BINAP (60.9 mg, 98 μmol), 2-bromo-1-fluoro-4-(trifluoromethoxy)benzene (140 mg, 0.54 mmol) and DMF (3.7 mL) were placed in a sealed vial which was then evacuated and back filled with argon three times. The mixture was heated at 90° C. for 24 h and then cooled to room temperature and filtered through a plug of silica (EtOAc as eluent). The filtrate was diluted with water and the product was extracted with EtOAc. The organic solution was washed with brine, dried over Na$_2$SO$_4$, filtered and concentrated in vacuo. The product was purified by silica gel chromatography (1-5% EtOAc in pet. ether) to give methyl 3-(2-(2-fluoro-5-(trifluoromethoxy)phenyl)-1,2,3,4-tetrahydroisoquinolin-6-yl)-2-methylpropanoate 26c as a colourless oil: $^1$H NMR (400 MHz, CDCl$_3$) δ 7.06-6.94 (m, 4H), 6.85-6.80 (m, 1H), 6.79-6.73 (m, 1H), 4.27 (s, 2H), 3.65 (s, 3H), 3.45 (t, J=5.9 Hz, 2H), 3.04-2.94 (m, 3H), 2.78-2.68 (m, 1H), 2.66-2.59 (m, 1H), 1.16 (d, J=6.9 Hz, 3H); ESI-HRMS calculated for C$_{21}$H$_{22}$F$_4$NO$_3$ (M+H$^+$) 412.1530, found 412.1519.

A mixture of methyl 3-(2-(2-fluoro-5-(trifluoromethoxy)phenyl)-1,2,3,4-tetrahydroisoquinolin-6-yl)-2-methylpropanoate 26c (81 mg, 0.20 mmol) and LiOH.H$_2$O (35 mg, 0.84 mmol) in THF (1.5 mL) and water (1.5 mL) was stirred at 45° C. for 5 h. The reaction mixture was cooled to RT and acidified (pH 1) by the addition of 1 M HCl (aq). The product was extracted with EtOAc and the organic solution was washed with brine, dried over Na$_2$SO$_4$, filtered and concentrated in vacuo. The product was purified by silica gel chromatography (38% EtOAc with 0.01% AcOH in pet. ether) to afford 3-(2-(2-fluoro-5-(trifluoromethoxy)phenyl)-1,2,3,4-tetrahydroisoquinolin-6-yl)-2-methylpropanoic acid 26 as a white solid: $^1$H NMR (400 MHz, CDCl$_3$) δ 7.06-6.97 (m, 4H), 6.83 (dd, J=7.2, 2.7 Hz, 1H), 6.79-6.74 (m, 1H), 4.27 (s, 2H), 3.45 (t, J=5.8 Hz, 2H), 3.09-3.01 (m, 1H), 2.98 (t, J=5.8 Hz, 2H), 2.81-2.72 (m, 1H), 2.68-2.60 (m, 1H), 1.19 (d, J=6.9 Hz, 3H); ESI-HRMS calculated for C$_{20}$H$_{20}$F$_4$NO$_3$ (M+H$^+$) 398.1374, found 398.1383.

Human GPR120 pEC$_{50}$: 7.1

The following compounds were prepared using appropriate starting materials in an analogous procedure to that described in Experimental Scheme 3.

| Example | Structure | [M + H]+ | NMR | hGPR120 pEC50 |
|---|---|---|---|---|
| 27 | 3-(2-(5-cyclobutoxy-2-fluorophenyl)-1,2,3,4-tetrahydroisoquinolin-6-yl)-2-methylpropanoic acid | 384 | (CDCl$_3$) δ 7.05-6.88 (m, 4H), 6.52-6.47 (m, 1H), 6.33-6.27 (m, 1H), 4.59-4.50 (m, 1H), 4.25 (s, 2H), 3.41 (t, J = 5.8 Hz, 2H), 3.08-3.00 (m, 1H), 2.94 (t, J = 5.7 Hz, 2H), 2.80-2.70 (m, 1H), 2.66-2.58 (m, 1H), 2.44-2.34 (m, 2H), 2.19-2.07 (m, 2H), 1.89-1.78 (m, 1H), 1.72-1.59 (m, 1H), 1.18 (d, J = 6.9 Hz, 3H) | 7.0 |

Experimental Scheme 4

Compound 28 3-(2-(3-Isopropoxyphenyl)-1,2,3,4-tetrahydroisoquinolin-6-yl)propanoic Acid

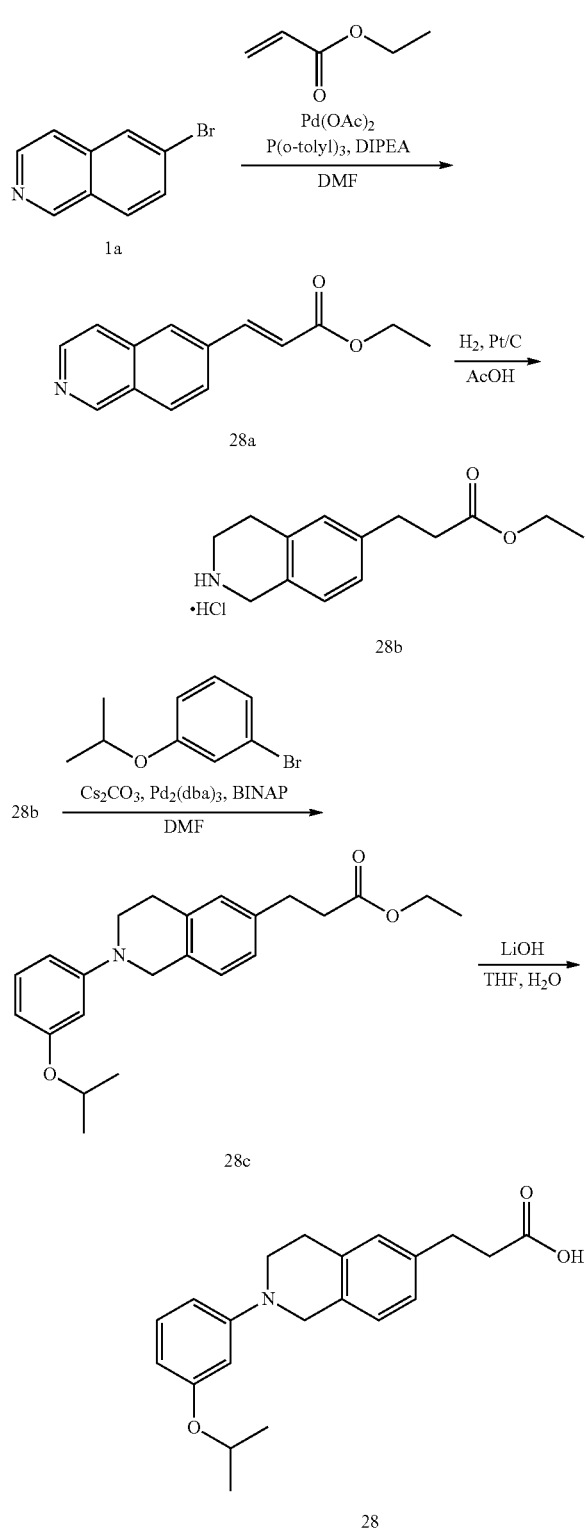

a) Procedure for the Preparation of 28a

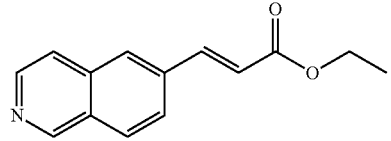 [SMILES: CCOC(=O)/C=C/c1ccc2cnccc2c1]

A flask was charged with 6-bromoisoquinoline 1a (5.1 g, 24 mmol), Pd(OAc)$_2$ (58 mg, 0.26 mmol), tri(o-tolyl)phosphine (156 mg, 0.513 mmol), DMF (33 mL) and DIPEA (8.4 mL, 48 mmol). The flask was evacuated and backfilled with argon three times before the addition of ethyl acrylate (3.9 mL, 37 mmol) and heated at 90° C. for 18 h. The reaction was cooled to RT, diluted with EtOAc and filtered through a short plug of silica. The filtrate was diluted with water and the product was extracted with EtOAc. The organic solution was washed with brine, dried over Na$_2$SO$_4$, filtered and concentrated in vacuo. The product was purified by recrystallisation from EtOAc to give ethyl (E)-3-(isoquinolin-6-yl)acrylate 28a as light yellow crystals: $^1$H NMR (400 MHz, CDCl$_3$) δ 9.25 (s, 1H), 8.57 (d, J=5.7 Hz, 1H), 7.97 (d, J=8.5 Hz, 1H), 7.90 (s, 1H), 7.83 (d, J=16.1 Hz, 1H), 7.78 (dd, J=8.6, 1.6 Hz, 1H), 7.66 (d, J=5.8 Hz, 1H), 6.61 (d, J=16.0 Hz, 1H), 4.31 (q, J=7.1 Hz, 2H), 1.37 (t, J=7.1 Hz, 3H); ESI-HRMS calculated for C$_{14}$H$_{14}$NO$_2$ (M+H$^+$) 228.1019, found 228.1024.

b) Procedure for the Preparation of 28b

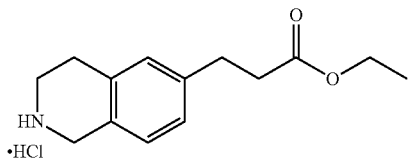 [SMILES: CCOC(=O)CCc1ccc2c(c1)CCNC2 ; Cl]

Ethyl (E)-3-(isoquinolin-6-yl)acrylate 28a (3.1 g, 14 mmol) was dissolved in glacial AcOH (130 mL) and under a blanket of argon, 5% Pt/C (2.3 g, 0.58 mmol) was added. The flask was evacuated and backfilled with H$_2$ three times and the mixture was stirred at 50° C. under an atmosphere of H$_2$. After 18 h the mixture was cooled to RT, filtered through a plug of celite, washing through with EtOAc. The filtrate was concentrated in vacuo, then the residue was dissolved in DCM and concentrated in vacuo. The resulting oil was cooled to 0° C. and 4 M HCl in dioxane (12 mL) was added. The mixture was stirred for 5 min where after white precipitate formed. The solid was resuspended in DCM and concentrated in vacuo to give ethyl 3-(1,2,3,4-tetrahydroisoquinolin-6-yl)propanoate hydrochloride 28b as a white solid: 1H NMR (400 MHz, CDCl$_3$) δ 8.68 (br s, 2H), 7.13-6.96 (m, 3H), 4.27 (br s, 2H), 4.13 (q, J=7.1 Hz, 2H), 3.39 (br s, 2H), 3.09 (br s, 2H), 2.90 (t, J=7.7 Hz, 2H), 2.59 (t, J=7.7 Hz, 2H), 1.24 (t, J=7.1 Hz, 3H); ESI-HRMS calculated for C$_{14}$H$_{20}$NO$_2$ (M+H$^+$) 234.1489, found 234.1493.

c) Procedure for the Preparation of 28c

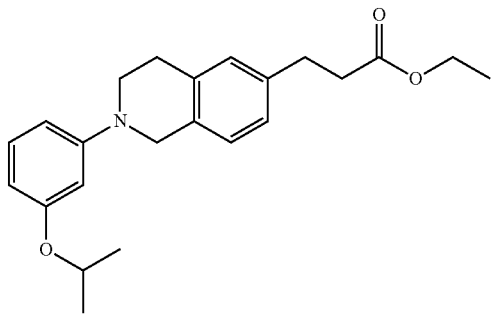 [SMILES: CCOC(=O)CCc1ccc2c(c1)CCN(c1cccc(OC(C)C)c1)C2]

Ethyl 3-(1,2,3,4-tetrahydroisoquinolin-6-yl)propanoate hydrochloride 28b (136.2 mg, 0.50 mmol), $Cs_2CO_3$ (586 mg, 1.8 mmol), XPhos Pd G4 precatalyst (12.4 mg, 14.5 μmol), 1-bromo-3-isopropoxybenzene (119.5 mg, 0.55 mmol) and dioxane (2 mL) were placed in a sealed vial which was then evacuated and back filled with argon three times. The mixture was stirred at 90° C. for 18 h then cooled to RT. The mixture was filtered through a plug of silica, washing through with EtOAc and the filtrate was concentrated in vacuo. The product was purified by silica gel chromatography (0-8% EtOAc in pet. ether) to give ethyl 3-(2-(3-isopropoxyphenyl)-1,2,3,4-tetrahydroisoquinolin-6-yl)propanoate 28c as a colourless oil: $^1$H NMR (400 MHz, $CDCl_3$) δ δ 7.16 (t, J=8.2 Hz, 1H), 7.09-6.97 (m, 3H), 6.55 (dd, J=8.2, 2.0 Hz, 1H), 6.49 (t, J=2.1 Hz, 1H), 6.37 (dd, J=8.1, 1.9 Hz, 1H), 4.61-4.50 (m, 1H), 4.36 (s, 2H), 4.13 (q, J=7.1 Hz, 2H), 3.52 (t, J=5.8 Hz, 2H), 2.97-2.87 (m, 4H), 2.60 (t, J=7.8 Hz, 2H), 1.34 (d, J=6.1 Hz, 6H), 1.24 (t, J=7.1 Hz, 3H); ESI-HRMS calculated for $C_{23}H_{30}NO_3$ (M+H$^+$) 368.2220, found 368.2233.

d) Procedure for the Preparation of Compound 28
3-(2-(3-Isopropoxyphenyl)-1,2,3,4-tetrahydroisoquinolin-6-yl)propanoic Acid

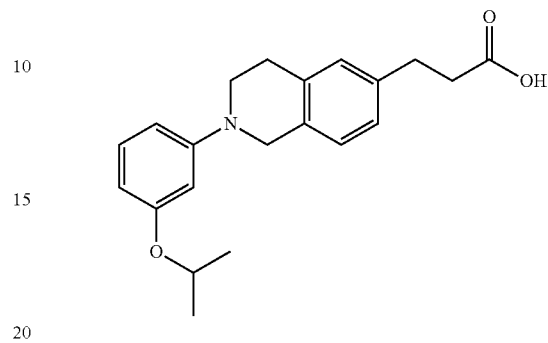

A mixture of ethyl 3-(2-(3-isopropoxyphenyl)-1,2,3,4-tetrahydroisoquinolin-6-yl)propanoate 28c (120 mg, 0.32 mmol) and $LiOH \cdot H_2O$ (54 mg, 1.3 mmol) in THF (5 mL) and water (5 mL) was stirred at RT for 18 h. The mixture was acidified (pH 4) by the addition of 1 M HCl (aq) and the product was extracted with EtOAc. The organic solution was washed with brine, dried over $Na_2SO_4$, filtered and concentrated in vacuo. The product was purified by silica gel chromatography (0-22% (0.01% AcOH in EtOAc) in pet. ether) to afford 3-(2-(3-isopropoxyphenyl)-1,2,3,4-tetrahydroisoquinolin-6-yl)propanoic acid 28 as a white solid: $^1$H NMR (400 MHz, $CDCl_3$) δ 7.16 (t, J=8.2 Hz, 1H), 7.10-6.99 (m, 3H), 6.56 (dd, J=8.1, 2.1 Hz, 1H), 6.50 (t, J=2.3 Hz, 1H), 6.37 (dd, J=8.0, 2.2 Hz, 1H), 4.61-4.50 (m, 1H), 4.36 (s, 2H), 3.53 (t, J=5.9 Hz, 2H), 2.93 (dd, J=11.9, 6.7 Hz, 4H), 2.68 (t, J=7.8 Hz, 2H), 1.34 (d, J=6.1 Hz, 6H); ESI-HRMS calculated for $C_{21}H_{26}NO_3$ (M+H$^+$) 340.1907, found 340.1917.

Human GPR120 pEC$_{50}$: 6.3

The following compound was prepared using appropriate starting materials in an analogous procedure to that described in Experimental Scheme 4.

| Compound | Structure | [M + H]+ | NMR | hGPR120 pEC50 |
|---|---|---|---|---|
| 29 | 3-(2-(5-chloro-2-methoxyphenyl)-1,2,3,4-tetrahydroisoquinolin-6-yl)propanoic acid | 346/348 | (DMSO-d$_6$) δ 7.22-6.75 (m, 6H), 4.13 (s, 2H), 3.80 (s, 3H), 3.28 (t, J = 5.8 Hz, 2H), 2.84 (t, J = 5.8 Hz, 2H), 2.76 (t, J = 7.6 Hz, 2H), 2.46 (d, J = 7.6 Hz, 2H). | 6.0 |

Experimental Scheme 5

Compound 30 3-(2-(3,5-Dimethylphenyl)-1,2,3,4-tetrahydroisoquinolin-7-yl)propanoic Acid

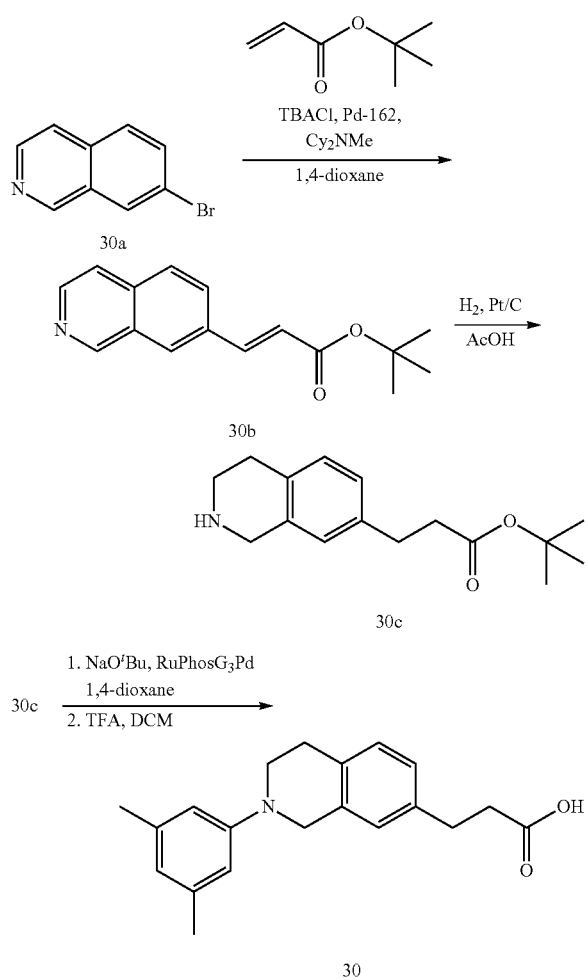

a) Procedure for the Preparation of 24b

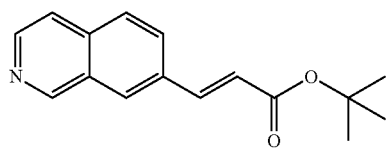 [SMILES: CC(C)(C)OC(=O)/C=C/c1ccc2ccncc2c1]

tert-Butyl (E)-3-(isoquinolin-7-yl)acrylate 30b was prepared from 7-bromoisoquinoline (5 g, 24 mmol) 30a using a procedure essentially the same as for compound 1a: m/z 256 [M+H]$^+$ (ES$^+$). $^1$H NMR (400 MHz, CDCl$_3$) δ 9.30 (s, 1H), 8.58 (d, J=5.7 Hz, 1H), 8.07 (s, 1H), 7.91 (dd, J=8.6, 1.7 Hz, 1H), 7.86 (d, J=8.6 Hz, 1H), 7.78 (d, J=16.0 Hz, 1H), 7.69 (dt, J=5.8, 1.0 Hz, 1H), 6.55 (d, J=16.0 Hz, 1H), 1.58 (s, 9H).

b) Procedure for the Preparation of 30c

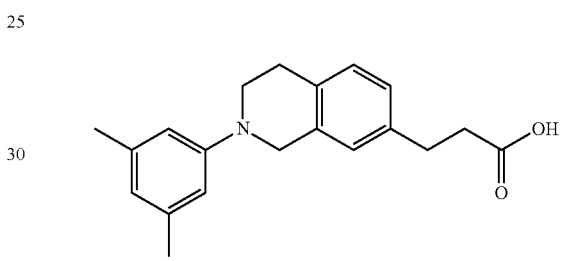

tert-Butyl 3-(1,2,3,4-tetrahydroisoquinolin-7-yl)propanoate 30c was prepared from tert-butyl (E)-3-(isoquinolin-7-yl)acrylate 30b (5 g, 19.6 mmol) using a procedure essentially the same as for compound 1c: m/z 262 [M+H]$^+$ (ES$^+$); $^1$H NMR (400 MHz, CDCl$_3$) δ 6.97-6.86 (m 2H), 6.81-6.75 (m, 1H), 3.91 (d, J=1.0 Hz, 2H), 3.05 (t, J=6.0 Hz, 2H), 2.77 (t, J=7.9 Hz, 2H), 2.69 (t, J=6.0 Hz, 2H), 2.48-2.39 (m, 2H), 1.36 (s, 9H).

c) Procedure for the Preparation of Compound 30 3-(2-(3,5-dimethylphenyl)-1,2,3,4-tetrahydroisoquinolin-7-yl)propanoic Acid RuPhos G3 Precatalyst (10 mg, 12 μmol) and NaO$^t$Bu (75 mg, 0.78 mmol) were placed in a sealed vial which was then evacuated and backfilled with nitrogen three times. A solution of tert-butyl 3-(1,2,3,4-tetrahydroisoquinolin-7-yl)propanoate 30c (100 mg, 0.4 mmol) and 1-bromo-3,5-dimethylbenzene (55 μL, 0.41 mmol) in 1,4-dioxane (2 mL) was added and the mixture was stirred, under nitrogen at 90° C. The mixture was cooled to RT and AcOH (55 μL, 0.96 mmol) was added. The mixture was partitioned between EtOAc (5 mL) and sat. NH$_4$Cl solution (5 mL) and the organic solution was dried over MgSO$_4$, filtered and concentrated in vacuo. The product was purified by silica gel chromatography (0-20% EtOAc in isohexane) to afford a mixture of the title compound and its tert-butyl ester. The mixture was dissolved in DCM (2 mL), treated with TFA (1 mL, 13 mmol) for 16 h and then concentrated in vacuo. Partial oxidation of the heterocycle was observed and so the residue was dissolved in DCM (5 mL), sodium triacetoxyborohydride (50 mg, 0.24 mmol) was added and the mixture was stirred at RT for 10 min and then concentrated in vacuo. The product was purified by reverse-phase flash chromatography (15-75% MeCN in water with 0.1% formic acid) to afford 3-(2-(3,5-dimethylphenyl)-1,2,3,4-tetrahydroisoquinolin-7-yl)propanoic acid 30 as a yellow gum: m/z 310 [M+H]$^+$ (ES$^+$); $^1$H NMR (400 MHz, DMSO-d$_6$) δ 12.12 (s, 1H), 7.09-6.97 (m, 3H), 6.60 (d, J=1.4 Hz, 2H), 6.39 (s, 1H), 4.29 (s, 2H), 3.46 (t, J=5.9 Hz, 2H), 2.84 (t, J=5.8 Hz, 2H), 2.78 (t, J=7.6 Hz, 2H), 2.57-2.51 (m, 2H), 2.21 (s, 6H).

Human GPR120 pEC$_{50}$: 5.8

The following compounds were prepared using appropriate starting materials in an analogous procedure to that described in Experimental Scheme 5.

| Compound | Structure | [M + H]+ | NMR | hGPR120 pEC50 |
|---|---|---|---|---|
| 31 | 3-(2-(3-chloro-5-methoxyphenyl)-1,2,3,4-tetrahydroisoquinolin-7-yl)propanoic acid | 349/348 | (DMSO-d$_6$) δ 12.14 (s, 1H), 7.11-6.99 (m, 3H), 6.59 (t, J = 2.0 Hz, 1H), 6.42 (t, J = 2.2 Hz, 1H), 6.35 (t, J = 1.9 Hz, 1H), 4.36 (s, 2H), 3.74 (s, 3H), 3.51 (t, J = 5.9 Hz, 2H), 2.84 (t, J = 5.9 Hz, 2H), 2.78 (t, J = 7.6 Hz, 2H), 2.55-2.51 (m, 2H). | 5.6 |
| 32 | 3-(2-(3-cyclobutoxyphenyl)-1,2,3,4-tetrahydroisoquinolin-7-yl)propanoic acid | 366 | (DMSO-d$_6$) δ 7.91 (d, J = 1.8 Hz, 1H), 7.43 (dd, J = 7.8, 1.9 Hz, 1H), 7.36-7.25 (m, 2H), 6.94 (ddd, J = 7.9, 2.0, 0.9 Hz, 1H), 6.89 (t, J = 2.2 Hz, 1H), 6.79 (ddd, J = 8.3, 2.5, 0.9 Hz, 1H), 4.77-4.65 (m, 1H), 3.95 (dd, J = 7.0, 6.1 Hz, 2H), 3.13 (t, J = 6.5 Hz, 2H), 2.98 (t, J = 7.6 Hz, 2H), 2.64 (t, J = 7.6 Hz, 2H), 2.55-2.41 (m, 2H), 2.14 (dtdd, J = 12.5, 9.8, 6.7, 2.7 Hz, 2H), 1.92-1.80 (m, 1H), 1.80-1.66 (m, 1H) —COOH not observed, 1 CH$_2$ under DMSO peak | 5.2 |
| 33 | 3-(2-(2-fluoro-5-(trifluoromethoxy)phenyl)-1,2,3,4-tetrahydroisoquinolin-7-yl)propanoic acid | 384 | (Chloroform-d) δ 7.12-6.94 (m, 4H), 6.86-6.72 (m, 2H), 4.28 (s, 2H), 3.45 (t, J = 5.8 Hz, 2H), 3.02-2.87 (m, 4H), 2.68 (t, J = 7.7 Hz, 2H). | 5.9 |

Experimental Scheme 6

Compound 34 2-(2-(5-Cyclobutoxy-2-fluorophenyl)-1,2,3,4-tetrahydroisoquinolin-6-yl)cyclopropane-1-carboxylic Acid

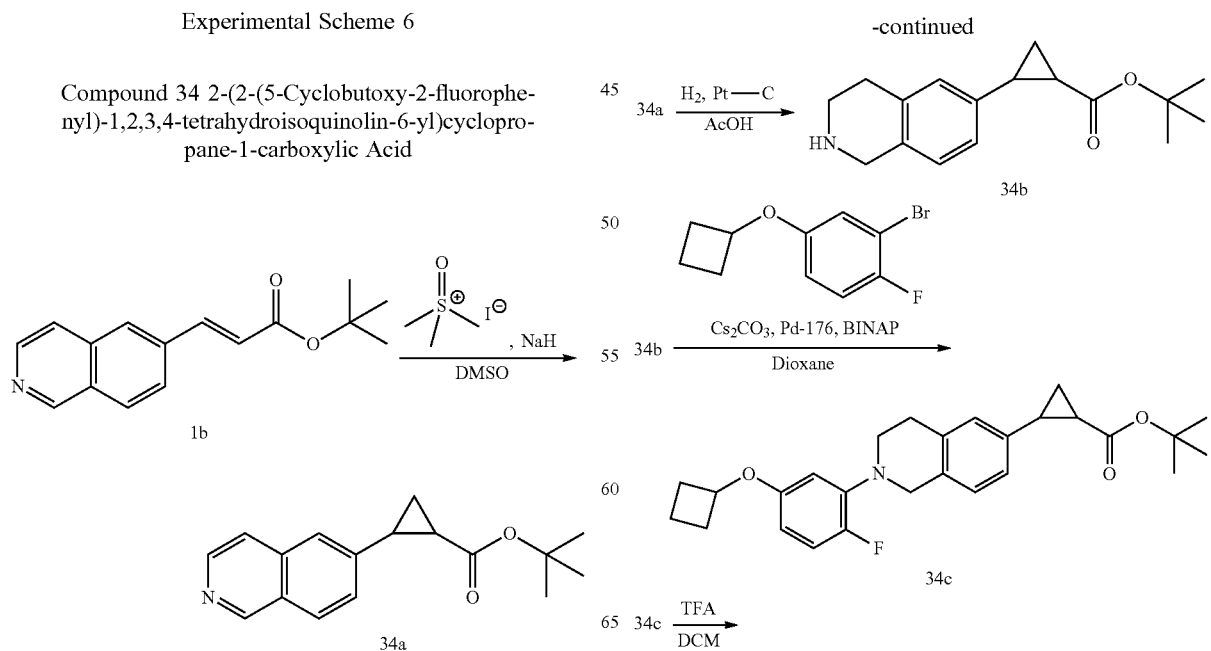

-continued

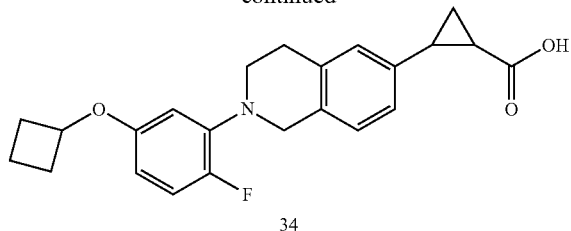

34 a) Procedure for the Preparation of 34a

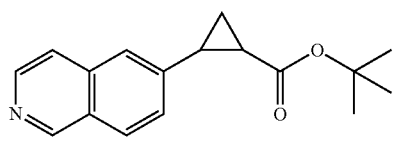 [SMILES: CC(C)(C)OC(=O)C1CC1c1ccc2cnccc2c1]

A solution of trimethylsulfoxonium iodide (13 g, 59 mmol) in DMSO (75 mL) was added dropwise to a suspension of NaH (60% w/w in oil, 2.1 g, 53 mmol) in DMSO (40 mL) under nitrogen. The mixture was stirred at RT for 1 h before the dropwise addition of a solution of (E)-tert-butyl 3-(isoquinolin-6-yl)acrylate 1b (10 g, 36 mmol) in DMSO (50 mL). The mixture was stirred at RT for 16 h, then partitioned between 20% w/w NaCl soln (1 L) and TBME (1 L). The organic solution was washed with 20% w/w NaCl soln (1 L), dried over MgSO$_4$, filtered and concentrated in vacuo. The resultant oil was purified by silica gel chromatography (10-30% EtOAc in isohexane) to afford tert-butyl 2-(isoquinolin-6-yl)cyclopropanecarboxylate 34a as a colourless solid: m/z 270 [M+H]$^+$ (ES$^+$). $^1$H NMR (400 MHz, CDCl$_3$) δ 9.21 (s, 1H), 8.49 (d, J=5.9 Hz, 1H), 7.92 (d, J=8.5 Hz, 1H), 7.62 (d, J=5.8 Hz, 1H), 7.56 (s, 1H), 7.34 (dd, J=8.5, 1.7 Hz, 1H), 2.68-2.59 (m, 1H), 2.05-1.95 (m, 1H), 1.72-1.63 (m, 1H), 1.51-1.46 (m, 9H), 1.43-1.31 (m, 1H).

b) Procedure for the Preparation of 34b

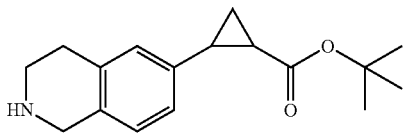 [SMILES: CC(C)(C)OC(=O)C1CC1c1ccc2c(c1)CCNC2]

A mixture of tert-butyl 2-(isoquinolin-6-yl)cyclopropanecarboxylate 34a (2 g, 7.4 mmol) and Pt—C 5% (50% w/w with water J&M type 117) (500 mg, 0.06 mmol) in AcOH (20 mL) was stirred under an atmosphere of hydrogen (5 Bar) at RT for 18 h and then filtered. The filtrate was concentrated in vacuo and the residue was partitioned between 1N NaOH (50 mL) and EtOAc (100 mL). The organic solution was dried over MgSO$_4$, filtered and concentrated in vacuo to give tert-butyl 2-(1,2,3,4-tetrahydroisoquinolin-6-yl)cyclopropanecarboxylate 34b as a colourless oil that crystallised on standing: m/z 274 [M+H]$^+$ (ES$^+$). $^1$H NMR (400 MHz, CDCl$_3$) δ 6.92 (d, J=7.9 Hz, 1H), 6.91-6.80 (m, 2H), 3.97 (s, 2H), 3.12 (t, J=6.0 Hz, 2H), 2.76 (t, J=6.0 Hz, 2H), 2.43-2.33 (m, 1H), 1.84-1.74 (m, 1H), 1.54-1.46 (m, 1H), 1.46 (s, 9H), 1.23-1.14 (m, 1H), —NH not observed.

c) Procedure for the Preparation of 34c

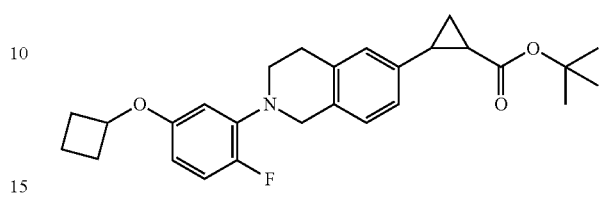

A flask containing Cs$_2$CO$_3$ (3.7 g, 11 mmol), BINAP (0.2 g, 0.4 mmol) and Pd-176 [BINAP Pd(allyl)]Cl.0.5C7H8 (0.2 g, 0.3 mmol) was evacuated and backfilled with nitrogen (3 times). A solution of tert-butyl 2-(1,2,3,4-tetrahydroisoquinolin-6-yl)cyclopropanecarboxylate 34b (2.1 g, 7.5 mmol) and 2-bromo-4-cyclobutoxy-1-fluorobenzene (2.0 g, 8.3 mmol) in 1,4-dioxane (25 mL) was added and the flask was once again evacuated and backfilled with nitrogen (4 times). The resultant mixture was heated at 95° C. (internal temperature) for 16 h, then cooled to RT and partitioned between 20% w/w NaCl soln. (100 mL) and EtOAc (200 mL). The organic solution was washed with 20% w/w NaCl soln. (10 mL), dried over MgSO$_4$, filtered and concentrated in vacuo. The residue was purified by silica gel chromatography (0-20% EtOAc in isohexane) to afford tert-butyl 2-(2-(5-cyclobutoxy-2-fluorophenyl)-1,2,3,4-tetrahydroisoquinolin-6-yl)cyclopropanecarboxylate 34c as a thick colourless oil: m/z 438 [M+H]$^+$ (ES$^+$). $^1$H NMR (400 MHz, CDCl$_3$) δ 6.93 (d, J=7.8 Hz, 1H), 6.90-6.78 (m, 3H), 6.49 (s, 1H), 6.25 (d, J=8.7 Hz, 1H), 4.47 (quint, J=7.2 Hz, 1H), 4.19 (s, 2H), 3.36 (t, J=5.8 Hz, 2H), 2.88 (s, 2H), 2.39-2.26 (m, 3H), 2.13-1.98 (m, 2H), 1.83-1.68 (m, 2H), 1.67-1.50 (m, 1H), 1.48-1.38 (m, 1H), 1.39 (s, 9H), 1.16-1.09 (m, 1H).

c) Procedure for the Preparation of 34 2-(2-(5-cyclobutoxy-2-fluorophenyl)-1,2,3,4-tetrahydroisoquinolin-6-yl)cyclopropanecarboxylic Acid

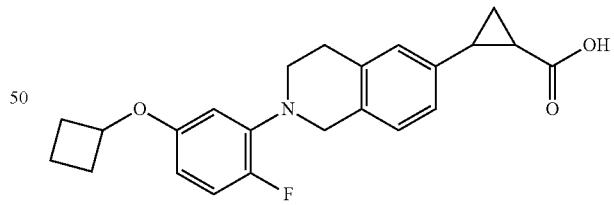

To a solution of tert-butyl 2-(2-(5-cyclobutoxy-2-fluorophenyl)-1,2,3,4-tetrahydroisoquinolin-6-yl)cyclopropanecarboxylate 34c (2.5 g, 5.8 mmol) in DCM (20 mL) was added TFA (5 mL, 65 mmol) and sodium triacetoxyborohydride (0.25 g, 1.2 mmol). The resultant mixture was stirred at RT for 3 h and then partitioned between DCM (25 mL) and water (50 mL). Residual product was extracted from the aqueous phase with further DCM (150 mL). The combined organics were washed with brine (50 mL), passed through a hydrophobic frit and then concentrated in vacuo. The residue was purified by silica gel chromatography (30-100% (1:1 DCM/EtOAc) in isohexane) to afford 2-(2-(5-cyclobutoxy- 2-fluorophenyl)-1,2,3,4-tetrahydroisoquinolin-6-yl)cyclopropanecarboxylic acid 34 as an off white solid and racemic mixture of trans enantiomers: m/z 382 [M+H]+ (ES+). ¹H NMR (400 MHz, DMSO-d₆) δ 7.08 (d, J=7.9 Hz, 1H), 7.02 (dd, J=12.6, 8.8 Hz, H), 6.99-6.92 (m, 2H), 6.47 (dd, J=7.5, 3.0 Hz, 1H), 6.36 (dt, J=8.8, 3.1 Hz, 1H), 4.61 (quint, J=7.1 Hz, 1H), 4.18 (s, 2H), 3.34 (t, =5.8 Hz, 2H), 2.83 (t, J=5.8 Hz, 2H), 2.43-2.27 (m, 3H), 2.06-1.92 (m, 2H), 1.81-1.69 (m, 2H), 1.69-1.49 (m, 1H), 1.46-11.36 (m, 1H), 1.36-1.26 (m, 1H), —COOH not observed.

Human GPRD120 pEC$_{50}$: 6.8

The following compounds were prepared using appropriate starting materials in an analogous procedure to that described in Experimental Scheme 6.

| Compound | Structure | [M + H]+ | NMR | hGPR120 pEC50 |
|---|---|---|---|---|
| 35 | 2-(2-(2-fluoro-5-(trifluoromethoxy)phenyl)-1,2,3,4-tetrahydroisoquinolin-6-yl)cyclopropane-1-carboxylic acid | 396 | (CDCl₃) δ 7.08-7.00 (m, 2H), 6.97-6.85 (m, 3H), 6.83-6.75 (m, 1H), 4.29 (s, 2H), 3.53-3.41 (m, 2H), 2.99 (t, J = 5.9 Hz, 2H), 2.64-2.53 (m, 1H), 1.95-1.85 (m, 1H), 1.65 (dt, J = 9.6, 4.9 Hz, 1H), 1.44-1.35 (m, 1H), —COOH not observed. | 7.0 |
| 36 | 2-(2-(5-cyclobutoxy-2,3-difluorophenyl)-1,2,3,4-tetrahydroisoquinolin-6-yl)cyclopropane-1-carboxylic acid | 400 | (DMSO-d₆) δ 12.27 (s, 1H), 7.09 (d, J = 7.9 Hz, 1H), 7.00-6.91 (m, 2H), 6.50-6.40 (m, 1H), 6.28 (dt, J = 6.8, 2.4 Hz, 1H), 4.63 (quint, J = 7.1 Hz, 1H), 4.23 (s, 2H), 3.39 (t, J = 5.9 Hz, 2H), 2.84 (t, J = 5.8 Hz, 2H), 2.45-2.29 (m, 3H), 2.05-1.90 (m, 2H), 1.82-1.70 (m, 2H), 1.68-1.54 (m, 1H), 1.44-1.36 (m, 1H), 1.36-1.26 (m, 1H). | 7.0 |
| 37 | 2-(2-(6-cyclobutoxy-3-fluoropyridin-2-yl)-1,2,3,4-tetrahydroisoquinolin-6-yl)cyclopropane-1-carboxylic acid | 383 | (DMSO-d₆) δ 12.27 (s, 1H), 7.42 (dd, J = 12.8, 8.4 Hz, 1H), 7.10 (d, J = 7.8 Hz, 1H), 6.99-6.90 (m, 2H), 6.07 (dd, J = 8.4, 1.7 Hz, 1H), 4.96 (quint, J = 7.4 Hz, 1H), 4.57 (s, 2H), 3.71 (t, J = 5.9 Hz, 2H), 2.86 (t, J = 5.9 Hz, 2H), 2.41-2.28 (m, 3H), 2.07-1.94 (m, 2H), 1.85-1.70 (m, 2H), 1.70-1.57 (m, 1H), 1.45-1.35 (m, 1H), 1.35-1.25 (m, 1H). | 7.4 |

Experimental Scheme 7

Compound 38 2-(2-(3-Phenoxyphenyl)-1,2,3,4-tetrahydroisoquinolin-6-yl)cyclopropane-1-carboxylic Acid

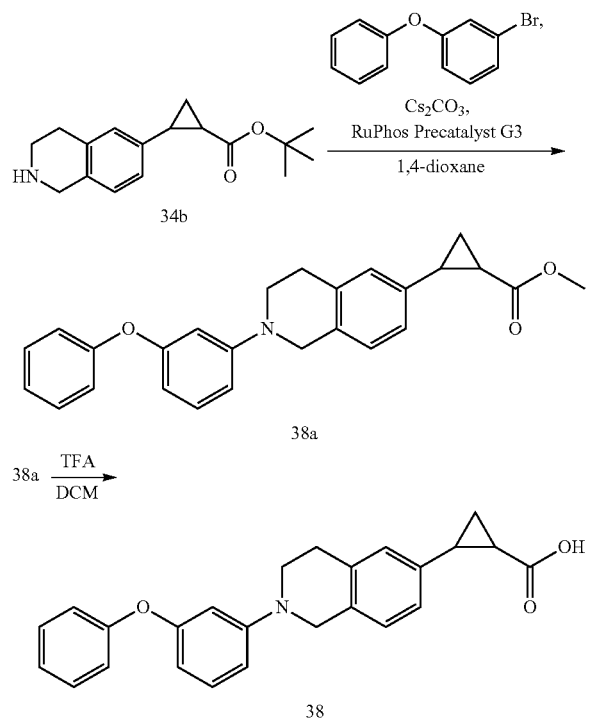

a) Procedure for the Preparation of 38a

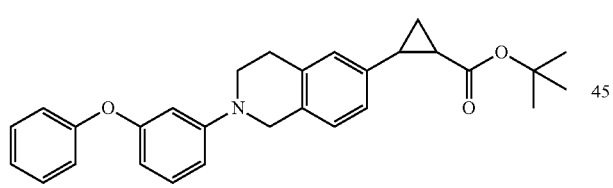

A vial containing $Cs_2CO_3$ (0.21 g, 0.64 mmol), tert-butyl 2-(1,2,3,4-tetrahydroisoquinolin-6-yl)cyclopropanecarboxylate 34b (0.12 g, 0.42 mmol) and RuPhos Pd G3 (11 mg, 0.013 mmol) was evacuated under vacuum and backfilled with nitrogen 3 times. A solution of 1-bromo-3-phenoxybenzene (0.12 g, 0.47 mmol) in 1,4-dioxane (2 mL) was added and the vial was once again evacuated under vacuum and backfilled with nitrogen 3 times. The resultant mixture was heated at 90° C. for 16 h, then cooled to RT and water (5 mL) was added. The product was extracted with DCM (15 mL) and the organic solution was passed through a hydrophobic membrane and concentrated in vacuo. The residue was purified by silica gel chromatography (0-20% EtOAc in isohexane) to afford tert-butyl 2-(2-(3-phenoxyphenyl)-1,2,3,4-tetrahydroisoquinolin-6-yl)cyclopropanecarboxylate 38a as a thick colourless oil: m/z 422 [M+H]$^+$ (ES$^+$). $^1$H NMR (400 MHz, CDCl$_3$) δ δ 7.38-7.29 (m, 2H), 7.22 (t, J=8.2 Hz, 1H), 7.12-7.00 (m, 4H), 6.91 (d, J=8.6 Hz, 2H), 6.72 (d, J=7.1 Hz, 1H), 6.65 (s, 1H), 6.44 (d, J=7.5 Hz, 1H), 4.37 (s, 2H), 3.53 (t, J=5.8 Hz, 2H), 2.93 (t, J=5.5 Hz, 2H), 2.45-2.36 (m, 1H), 1.86-1.73 (m, 1H), 1.52 (dt, J=9.5, 4.8 Hz, 1H), 1.47 (s, 9H), 1.26-1.18 (m, 1H).

b) Procedure for the Preparation of Compound 38 2-(2-(3-Phenoxyphenyl)-1,2,3,4-tetrahydroisoquinolin-6-yl)cyclopropanecarboxylic Acid

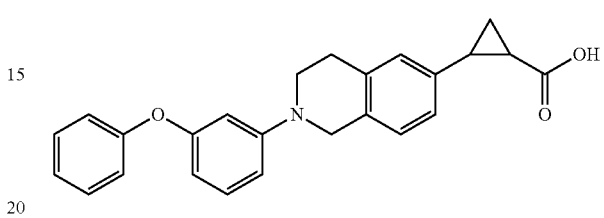

A solution tert-butyl 2-(2-(3-phenoxyphenyl)-1,2,3,4-tetrahydroisoquinolin-6-yl)cyclopropanecarboxylate 38a (125 mg, 0.28 mmol) in DCM (2 mL) was treated with sodium triacetoxyborohydride (60 mg, 0.28 mmol) and TFA (1 mL, 13 mmol) and the mixture was stirred at RT for 1 h. Water (2 mL) was added and the product was extracted with DCM (15 mL). The organic solution was passed through a hydrophobic membrane and then concentrated in vacuo. The product was purified by reverse-phase flash chromatography (25-100% MeCN in water with 0.1% formic acid) to afford 2-(2-(3-phenoxyphenyl)-1,2,3,4-tetrahydroisoquinolin-6-yl)cyclopropanecarboxylic acid 38 as a colourless solid: m/z 386 [M+H]$^+$ (ES$^+$). $^1$H NMR (400 MHz, DMSO-d$_6$) δ 12.30 (s, 1H), 7.41-7.32 (m, 2H), 7.20 (t, J=8.2 Hz, 1H), 7.15-7.07 (m, 2H), 7.01-6.94 (m, 4H), 6.77 (dd, J=8.3, 2.4 Hz, 1H), 6.65 (t, J=2.3 Hz, 1H), 6.29 (dd, J=7.9, 2.2 Hz, 1H), 4.34 (s, 2H), 3.50 (t, J=5.9 Hz, 2H), 2.84 (t, J=5.8 Hz, 2H), 2.37-2.29 (m, 1H), 1.80-1.72 (m, 1H), 1.39 (dt, J=9.2, 4.6 Hz, 1H), 1.35-1.26 (m, 1H).

Human GPR120 pEC$_{50}$: 7.2

Experimental Scheme 8

Compounds 34-isomer1 and 34-isomer2 2-(2-(5-Cyclobutoxy-2-fluorophenyl)-1,2,3,4-tetrahydroisoquinolin-6-yl)cyclopropane-1-carboxylic Acid

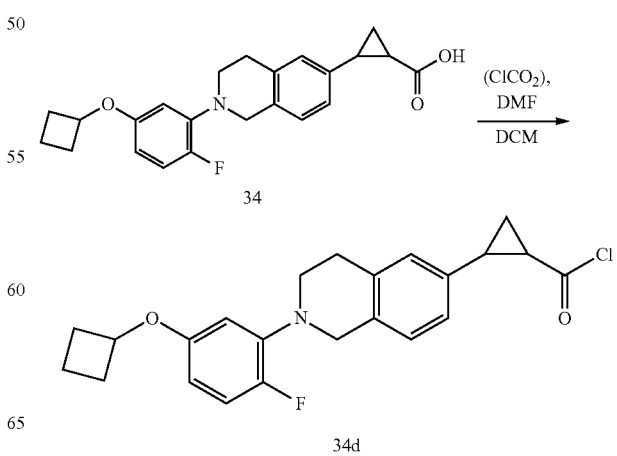

87

-continued

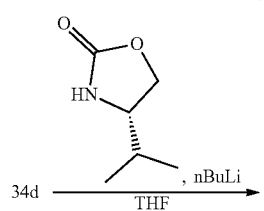

34d $\xrightarrow[\text{THF}]{\text{, nBuLi}}$

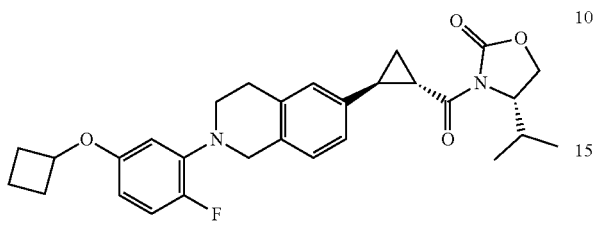

34e: isomer 1 and isomer 2

34e: isomers $\xrightarrow[\text{THF, H}_2\text{O}]{\text{H}_2\text{O}_2, \text{LiOH}}$

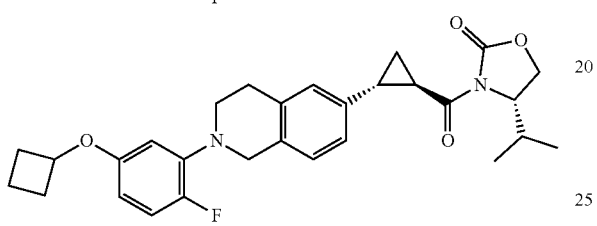

34: isomer 1 and isomer 2 a) Procedure for the Preparation of 34d

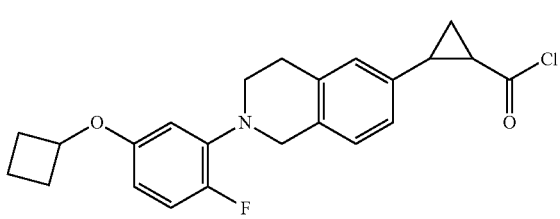 [SMILES: O=C(Cl)C1CC1c1ccc2c(c1)CCN(c1cc(OC3CCC3)ccc1F)C2]

88

Oxalyl chloride (0.5 mL, 6 mmol) and DMF (1 drop) were sequentially added to a solution of 2-(2-(5-cyclobutoxy-2-fluorophenyl)-1,2,3,4-tetrahydroisoquinolin-6-yl)cyclopropanecarboxylic acid 34 (1.9 g, 4.7 mmol) in DCM (20 mL) at 0° C. The mixture was stirred at 0° C. for 15 min, then warmed to RT and stirred for a further 2 h. The mixture was concentrated in vacuo to provide 2-(2-(5-cyclobutoxy-2-fluorophenyl)-1,2,3,4-tetrahydroisoquinolin-6-yl)cyclopropanecarbonyl chloride 34d as a yellow foam that was used directly in the next step without purification or analysis.

b) Procedure for the Preparation of 34e: Isomer 1 and Isomer 2

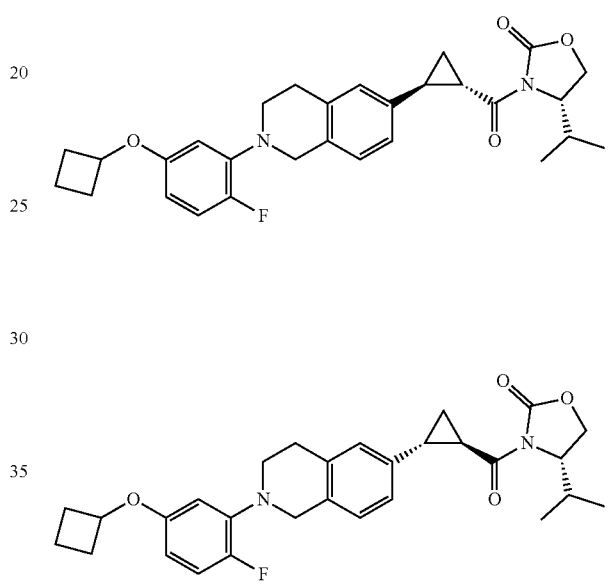

A solution of (S)-4-isopropyloxazoidin-2-one (1.3 g, 9.9 mmol) in THF (20 mL) was cooled to −78° C. and n-BuLi (2.5 M in hexane, 3.8 mL, 9.5 mmol) was added dropwise keeping internal temperature below −40° C. The mixture was stirred at −78° C. for 30 min, warmed to 0° C. and then cooled back down to −78° C. A solution of 2-(2-(5-cyclobutoxy-2-fluorophenyl)-1,2,3,4-tetrahydroisoquinolin-6-yl) cyclopropanecarbonyl chloride 34d (1.9 g, 4.7 mmol) in THF (20 mL) was added dropwise keeping the internal temp below −55° C. The resultant mixture was stirred at −78° C. for 30 min, then at −40° C. for 60 min. The reaction was quenched by the addition of sat. NH$_4$Cl (25 mL) and the product was extracted with EtOAc (100 mL). The organic solution was washed with brine (25 mL), dried over MgSO$_4$, filtered and concentrated in vacuo. The residue was purified by silica gel chromatography (0-35% EtOAc in isohexane) to afford (S)-3-(2-(2-(5-cyclobutoxy-2-fluorophenyl)-1,2,3,4-tetrahydroisoquinolin-6-yl)cyclopropanecarbonyl)-4-isopropyloxazolidin-2-one 34e isomer 1 and isomer 2 as thick colourless oils: Isomer 1: $^1$H NMR (400 MHz, CDCl$_3$) δ

7.05-6.87 (m, 4H), 6.53 (s, 1H), 6.36-6.27 (m, 1H), 4.60-4.51 (m, 2H), 4.50-4.41 (m, 1H), 4.34-4.18 (m, 4H), 3.60-3.51 (m, 1H), 3.42 (t, J=5.8 Hz, 2H), 2.95 (t, J=5.9 Hz, 2H), 2.65-2.55 (m, 1H), 2.46-2.32 (m, 2H), 2.21-2.07 (m, 2H), 1.91-1.77 (m, 1H), 1.78-1.68 (m, 1H), 1.73-1.58 (m, 1H), 1.46-1.34 (m, 1H), 0.92 (t, J=6.8 Hz, 6H).

Isomer 2: m/z 493 [M+H]$^+$ (ES$^+$). $^1$H NMR (400 MHz, CDCl$_3$) δ δ 1H NMR (400 MHz, Chloroform-d) 7.12-6.87 (m, 4H), 6.58 (s, 1H), 6.33 (d, J=8.8 Hz, 1H), 4.55 (p, J=7.2 Hz, 1H), 4.51-4.43 (m, 1H), 4.33-4.18 (m, 4H), 3.61-3.51 (m, 1H), 3.45 (t, J=5.9 Hz, 2H), 2.97 (s, 2H), 2.69-2.59 (m, 1H), 2.47-2.30 (m, 2H), 2.22-2.07 (m, 2H), 1.84 (q, J=10.5 Hz, 1H), 1.75-1.60 (m, 2H), 1.44-1.34 (m, 1H), 0.91 (dd, J=11.9, 7.0 Hz, 6H).

c) Procedure for the Preparation of 34: Isomer 1 and Isomer 2

Isomer 1: hydrogen peroxide 27% (w/w) (90 μl, 0.793 mmol) was added dropwise to a solution of LiOH (14 mg, 0.585 mmol) in water (0.1 ml) at room temperature. The resulting solution was stirred for 30 min and then cooled to 0° C. This cooled solution was added dropwise to a cooled solution of (S)-3-(2-(2-(5-cyclobutoxy-2-fluorophenyl)-1,2,3,4-tetrahydroisoquinolin-6-yl)cyclopropanecarbonyl)-4-isopropyloxazolidin-2-one 34e isomer 1 (95 mg, 0.193 mmol) in THF (0.3 ml). The reaction mixture was stirred for 60 minutes at 0° C. then room temperature for a further 60 minutes. Sodium sulfite (100 mg, 0.793 mmol) in water (0.3 ml) was added and the reaction mixture stirred for a further 10 min. The mixture was acidified to pH 5 with 1 M HCl and the product was extracted with EtOAc (2×5 ml). The combined organic phases were washed with brine (5 ml), dried with MgSO$_4$, filtered and concentrated in vacuo. The residue was purified by chromatography on silica (0-50% EtOAc in isohexane) to afford 34 isomer 1 as a colourless solid: m/z 382 [M+H]$^+$ (ES$^+$); $^1$H NMR (400 MHz, DMSO-d$_6$) δ 12.28 (s, 1H), 7.09 (d, J=7.9 Hz, 1H), 7.03 (dd, J=12.6, 8.8 Hz, 1H), 6.99-6.93 (m, 2H), 6.48 (dd, J=7.5, 3.0 Hz, 1H), 6.37 (dt, J=8.8, 3.1 Hz, 1H), 4.61 (p, J=7.1 Hz, 1H), 4.18 (s, 2H), 3.35 (t, J=5.9 Hz, 2H), 2.84 (t, J=5.9 Hz, 2H), 2.44-2.29 (m, 3H), 2.08-1.92 (m, 2H), 1.83-1.70 (m, 2H), 1.74-1.53 (m, 1H), 1.45-1.35 (m, 1H), 1.37-1.25 (m, 1H Human GPR120 pEC$_{50}$: 6.8

Isomer 2: 34 isomer 2 was prepared from (S)-3-(2-(2-(5-cyclobutoxy-2-fluorophenyl)-1,2,3,4-tetrahydroisoquinolin-6-yl)cyclopropanecarbonyl)-4-isopropyloxazolidin-2-one 34e isomer 2 using a procedure essentially the same as for 34 isomer 1 to afford 34 isomer 2 as a colourless solid: m/z 382 [M+H]$^+$ (ES$^+$); $^1$H NMR (400 MHz, DMSO-d$_6$) δ 12.23 (s, 1H), 7.09 (d, J=7.8 Hz, 1H), 7.03 (dd, J=12.6, 8.8 Hz, 1H), 7.00-6.92 (m, 2H), 6.48 (dd, J=7.5, 2:9 Hz, 1H), 6.37 (dt, J=8.8, 3.2 Hz, 1H), 4.61 (p, J=7.1 Hz, 1H), 4.18 (s, 2H), 3.35 (t, J=5.8 Hz, 2H), 2.84 (t, J=5.9 Hz, 2H), 2.44-2.29 (m, 3H), 2.00 (dtd, J=12.6, 10.0, 7.9 Hz, 2H), 1.83-1.69 (m, 2H), 1.70-1.53 (m, 1H), 1.45-1.36 (m, 1H), 1.37-1.27 (m, 1H).

Human GPR120 pEC$_{50}$: 7.1

The following compounds were prepared using appropriate starting materials in analogous procedure to that described in Experimental Scheme 8.

| Compound | Structure | [M + H]+ | NMR | hGPR120 pEC50 |
|---|---|---|---|---|
| 35 Isomers | 2-(2-(2-fluoro-5-(trifluoromethoxy)phenyl)-1,2,3,4-tetrahydroisoquinolin-6-yl)cyclopropane-1-carboxylic acid- | Isomer 1: 396 Isomer 2: 396 | Isomer 1: (Methanol-d$_4$) δ 7.20-7.02 (m, 2H), 6.96 (d, J = 6.9 Hz, 3H), 6.85 (d, J = 8.9 Hz, 1H), 4.25 (s, 2H), 3.44 (t, J = 5.8 Hz, 2H), 2.96 (t, J = 5.1 Hz, 4H), 2.49-2.36 (m, 1H), 1.82 (dt, J = 9.0, 4.8 Hz, 1H), 1.51 (dt, J = 9.4, 4.8 Hz, 1H), 1.40-1.30 (m, 1H), —COOH not observed. Isomer 2: (Methonol-d$_4$) δ 7.20-7.05 (m, 2H), 6.96 (d, J = 6.7 Hz, 3H), 6.85 (d, J = 8.6 Hz, 1H), 4.25 (s, 2H), 3.44 (t, J = 5.9 Hz, 2H), 2.95 (t, J = 5.9 Hz, 2H), 2.48-2.38 (m, 1H), 1.86-1.75 (m, 1H), 1.56-1.46 (m, 1H), 1.39-1.31 (m, 1H), —COOH not observed. | Isomer 1: 6.6 Isomer 1: 6.8 |

-continued

| Compound | Structure | [M + H]+ | NMR | hGPR120 pEC50 |
|---|---|---|---|---|
| 36 Isomers | | Isomer 1: 400 Isomer 2: 400 | Isomer 1: (DMSO-d₆) δ 7.08 (d, J = 7.9 Hz, 1H), 6.98-6.90 (m, 2H), 6.50-6.39 (m, 1H), 6.28 (dt, J = 6.6, 2.4 Hz, 1H), 4.63 (quint, J = 7.1 Hz, 1H), 4.22 (s, 2H), 3.39 (t, J = 5.9 Hz, 2H, overlapping with H2O peak), 2.84 (t, J = 5.8 Hz, 2H), 2.45-2.24 (m, 3H), 2.04-1.89 (m, 2H), 1.82-1.70 (m, 2H), 1.70-1.53 (m, 1H), 1.46-1.33 (m, 1H), 1.33-1.22 (m, 1H), —COOH not observed. Isomer 2: (DMSO-d₆) δ 7.08 (d, J = 7.9 Hz, 1H), 6.99-6.92 (m, 2H), 6.49-6.41 (m, 1H), 6.28 (dt, J = 6.7, 2.3 Hz, 1H), 4.63 (quint, J = 7.1 Hz, 1H), 4.22 (s, 2H), 3.39 (d, J = 11.7 Hz, 2H, overlapping with H2O peak), 2.84 (t, J = 5.9 Hz, 2H), 2.44-2.26 (m, 3H), 2.05-1.90 (m, 2H), 1.81-1.70 (m, 2H), 1.68-1.53 (m, 1H), 1.42-1.33 (m, 1H), 1.31-1.21 (m, 1H), —COOH not observed. | Isomer 1: 6.9 Isomer 1: 7.1 |

Experimental Scheme 9

Compounds 38-Isomer 1 and 38-Isomer 2

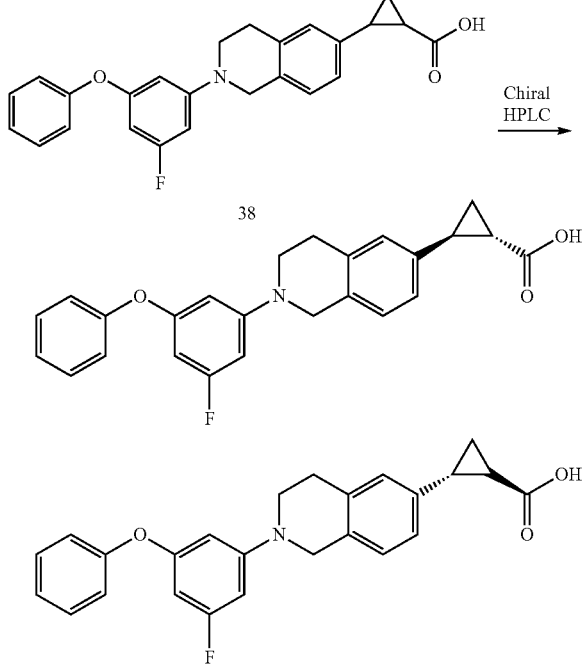

38: isomer 1 and isomer 2

2-(2-(3-Phenoxyphenyl)-1,2,3,4-tetrahydroisoquinolin-6-yl)cyclopropanecarboxylic acid 38 (55 mg, 0.14 mmol) was purified by preparative HPLC (ChiralPak IA column, 15 mL/min, 10% EtOH in isohexane (0.2% TFA)) to afford 2-(2-(3-Phenoxyphenyl)-1,2,3,4-tetrahydroisoquinolin-6-yl)cyclopropanecarboxylic acid 38 isomer 1 and isomer 2 as tan solids: Isomer 1: m/z 386 [M+H]⁺ (ES⁺); ¹H NMR (500 MHz, DMSO) δ 7.40-7.33 (m, 2H), 7.20 (t, J=8.2 Hz, 1H), 7.14-7.08 (m, 2H), 7.01-6.99 (m, 1H), 6.99-6.95 (m, 3H), 6.80-6.75 (m, 1H), 6.65 (t, J=2.3 Hz, 1H), 6.33-6.27 (m, 1H), 4.34 (s, 2H), 3.50 (t, J=5.9 Hz, 2H), 2.85 (t, J=5.9 Hz, 2H), 2.32 (ddd, J=4.1, 6.4, 9.1 Hz, 1H), 1.77 (ddd, J=4.1, 5.3, 8.3 Hz, 1H), 1.39 (ddd, J=4.2, 5.3, 9.2 Hz, 1H), 1.29 (ddd, J=4.2, 6.4, 8.3 Hz, 1H) —COOH not observed.

Human GPR120 pEC50: 7.3

Isomer 2: m/z 386 [M+H]⁺ (ES⁺); ¹H NMR (500 MHz, DMSO) δ 7.40-7.33 (m, 2H), 7.20 (t, J=8.2 Hz, 1H), 7.14-7.08 (m, 2H), 7.01-6.98 (m, 1H), 6.98-6.95 (m, 3H), 6.80-6.74 (m, 1H), 6.65 (t, J=2.3 Hz, 1H), 6.32-6.28 (m, 1H), 4.34 (s, 2H), 3.50 (t, J=5.9 Hz, 2H), 2.85 (t, J=5.9 Hz, 2H), 2.33 (ddd, J=4.0, 6.4, 9.2 Hz, 1H), 1.77 (ddd, J=4.1, 5.2, 8.3 Hz, 1H), 1.39 (ddd, J=4.2, 5.3, 9.2 Hz, 1H), 1.30 (ddd, J=4.2, 6.4, 8.3 Hz, 1H) —COOH not observed.

Human GPR120 pEC50: 7.4

The following compounds were prepared using appropriate starting materials in an analogous procedure to that described in Experimental Scheme 9.

| Compound | Structure | [M + H]+ | NMR | hGPR120 pEC50 |
|---|---|---|---|---|
| 37 Isomers | 2-(2-(6-cyclobutoxy-3-fluoropyridin-2-yl)-1,2,3,4-tetrahydroisoquinolin-6-yl)cyclopropane-1-carboxylic acid | Isomer 1: 383 Isomer 2: 383 | Isomer 1: (DMSO-d$_6$) δ 7.42 (dd, J = 12.8, 8.4 Hz, 1H), 7.09 (d, J = 7.9 Hz, 1H), 7.00-6.91 (m, 2H), 6.08 (dd, J = 8.4, 1.7 Hz, 1H), 4.96 (quint, J = 7.3 Hz, 1H), 4.58 (s, 2H), 3.71 (t, J = 5.8 Hz, 2H), 2.86 (t, J = 5.9 Hz, 2H), 2.45-2.27 (m, 3H), 2.09-1.93 (m, 2H), 1.83-1.70 (m, 2H), 1.73-1.56 (m, 1H), 1.43-1.32 (m, 1H), 1.34-1.21 (m, 1H), —COOH not observed. Isomer 2: (DMSO-d$_6$) δ 7.41 (dd, J = 12.8, 8.4 Hz, 1H), 7.08 (d, J = 7.8 Hz, 1H), 6.98-6.89 (m, 2H), 6.07 (dd, J = 8.4, 1.7 Hz, 1H), 4.95 (quint, J = 7.3 Hz, 1H), 4.57 (s, 2H), 3.71 (t, J = 5.9 Hz, 2H), 2.85 (t, J = 5.9 Hz, 2H), 2.43-2.21 (m, 3H), 2.09-1.93 (m, 2H), 1.83-1.69 (m, 2H), 1.72-1.55 (m, 1H), 1.36 (dt, J = 9.2, 4.7 Hz, 1H), 1.29-1.20 (m, 1H), —COOH not observed. | Isomer 1: 7.2 Isomer 1: 7.2 |

Experimental Scheme 10

Compound 393-(2-(5-Cyclobutoxy-2-fluorophenyl)-7-fluoro-1,2,3,4-tetrahydroisoquinolin-6-yl)propanoic Acid

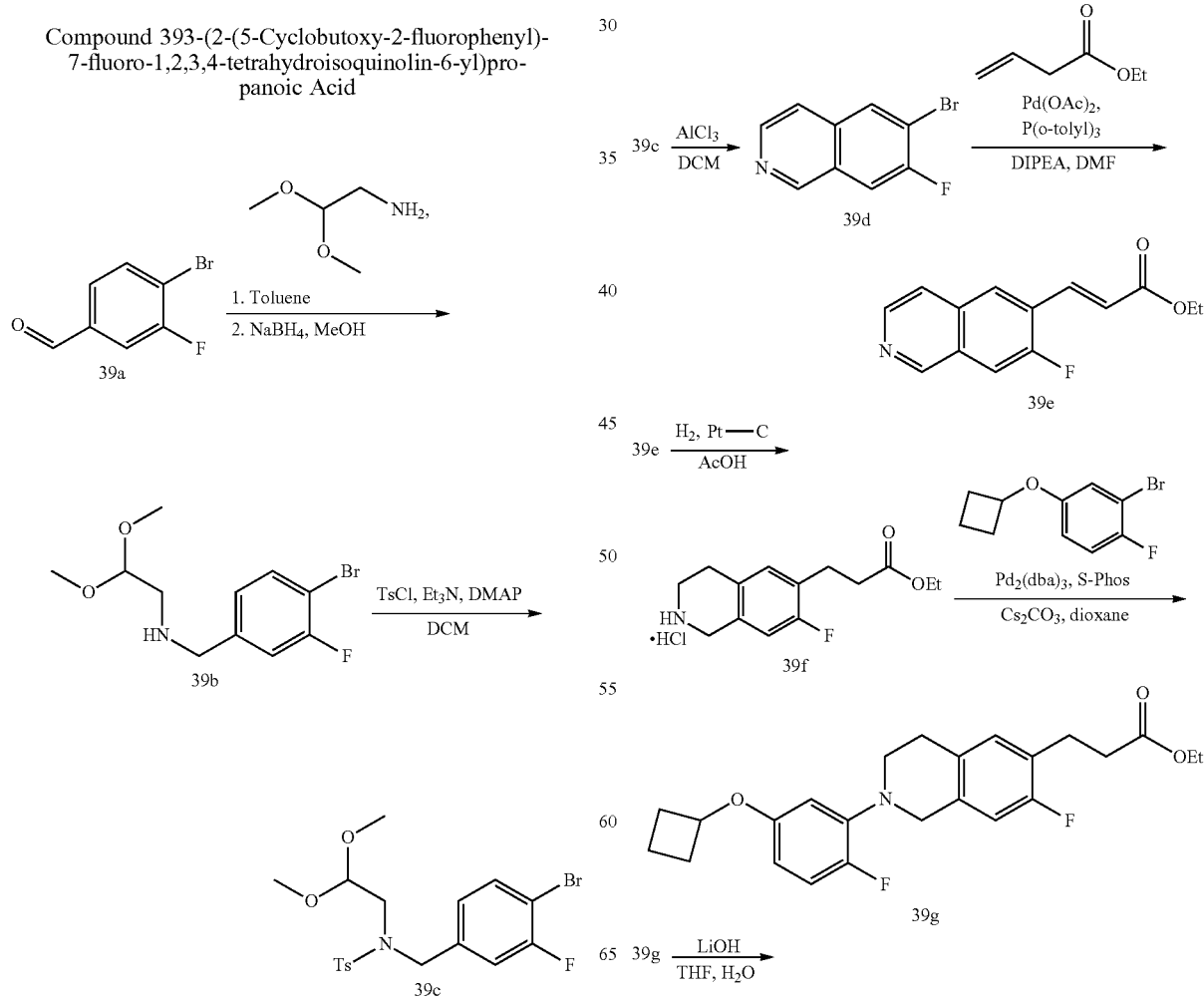

-continued

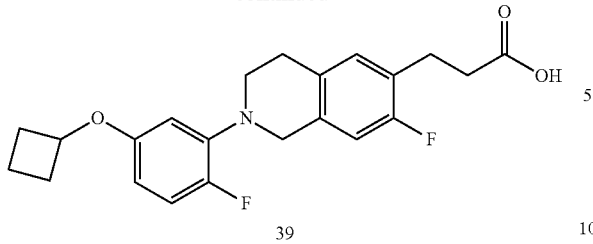

39 a) Procedure for the Preparation of 39b

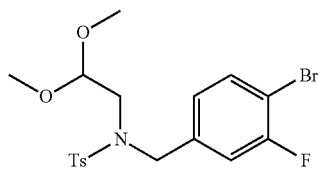 [SMILES: COC(CN(Cc1ccc(Br)c(F)c1)S(=O)(=O)c1ccc(C)cc1)OC]

A solution of 4-bromo-3-fluorobenzaldehyde 39a (5.0 g, 25 mmol), 2,2-dimethoxyethanamine (2.7 mL, 25 mmol) in anhydrous toluene (60 mL) was heated for two days at 135° C. using Dean stark apparatus. The reaction mixture was cooled to RT, concentrated in vacuo, diluted with MeOH and cooled to 0° C. under argon. Sodium borohydride (2.8 g, 74 mmol) was added portionwise and the mixture was stirred for 30 min at 0° C., then warmed to RT and stirred overnight. The reaction mixture was concentrated in vacuo, diluted with water and the product was extracted with EtOAc. The organic solution was washed with brine, dried over Na$_2$SO$_4$, filtered and concentrated in vacuo to afford N-(4-bromo-3-fluorobenzyl)-2,2-dimethoxyethan-1-amine 39b as orange oil that was used in the next step without further purification.

b) Procedure for the Preparation of 39c

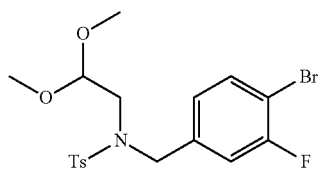 [SMILES: COC(CN(Cc1ccc(Br)c(F)c1)S(=O)(=O)c1ccc(C)cc1)OC]

Triethylamine (6.7 mL, 48 mmol) and DMAP (150 mg, 1.2 mmol) were added to a solution of N-(4-bromo-3-fluorobenzyl)-2,2-dimethoxyethan-1-amine 39b (7.0 g, 24 mmol) in anhydrous DCM (70 mL), under argon at 0° C. After 10 min tosyl chloride (4.8 g, 25 mmol) was added and the mixture was warmed to RT and stirred overnight. The mixture was diluted with DCM and washed with water and brine. The organic solution was dried over Na$_2$SO$_4$, filtered and concentrated in vacuo. The residue was purified by silica gel chromatography (0-30% EtOAc in pet. ether) to give N-(4-bromo-3-fluorobenzyl)-N-(2,2-dimethoxyethyl)-4-methylbenzenesulfonamide 39c as a yellow oil: $^1$H NMR (400 MHz, CDCl$_3$) δ 7.74-7.69 (m, 2H), 7.45 (dd, J=8.1, 7.1 Hz, 1H), 7.32 (d, J=7.9 Hz, 2H), 6.98 (dd, J=9.4, 2.0 Hz, 1H), 6.91 (dd, J=8.2, 1.5 Hz, 1H), 4.41 (s, 2H), 4.35 (t, J=5.3 Hz, 1H), 3.25 (s, 6H), 3.22 (d, J=5.3 Hz, 2H), 2.45 (s, 3H); ESI-HRMS calculated for C$_{18}$H$_{21}$BrFNO$_4$SNa (M+Na$^+$) 468.0251, found 468.0268.

c) Procedure for the Preparation of 39d

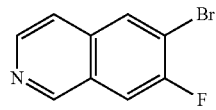

A suspension of anhydrous aluminum chloride (10.4 g, 78.0 mmol) in anhydrous DCM (100 mL) was cooled to −20° C., under argon before, a solution of N-(4-bromo-3-fluorobenzyl)-N-(2,2-dimethoxyethyl)-4-methylbenzenesulfonamide 39c (7.0 g, 16 mmol) in anhydrous dichloromethane (100 mL) was added. The mixture was warmed to RT and stirred for 2 days then concentrated in vacuo. The residue was cooled to 0° C. and water was added slowly, followed by 2 M potassium hydroxide solution (pH>10). The mixture was diluted with EtOAc and filtered through a pad of celite. The layers were separated and residual product was extracted from the aqueous phase with EtOAc (3×). The combined organic phases were washed with brine, dried over Na$_2$SO$_4$, filtered and concentrated in vacuo. The residue was purified by silica gel chromatography (0-35% EtOAc in pet. ether) to afforded 6-bromo-7-fluoroisoquinoline 39d as a pale brown solid: $^1$H NMR (400 MHz, CDCl$_3$) δ 9.21 (s, 1H), 8.55 (d, J=5.8 Hz, 1H), 8.12 (d, J=6.5 Hz, 1H), 7.66 (d, J=8.3 Hz, 1H), 7.59 (d, J=5.8 Hz, 1H); ESI-HRMS calculated for C$_9$H$_6$BrFN (M+H$^+$) 225.9668, found 225.9664.

d) Procedure for the Preparation of 39e

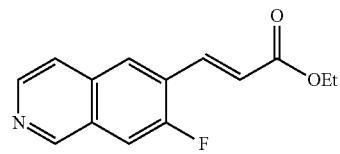 [SMILES: CCOC(=O)/C=C/c1cc2ccncc2cc1F]

A vial was charged with 6-bromo-7-fluoroisoquinoline 39d (1.2 g, 5.3 mmol), Pd(OAc)$_2$ (30 mg, 0.1 mmol), tris(o-tolyl)phosphine (8 mg, 0.3 mmol), anhydrous DMF (6 mL) and DIPEA (6 mL). The vial was evacuated and back filled with nitrogen three times before ethyl acrylate (0.69 mL, 6.4 mL) was added and the mixture was heated overnight at 100° C. under argon. The mixture was cooled to RT and water was added. The product was extracted with EtOAc and the combined organic solution was washed with brine, dried over Na$_2$SO$_4$, filtered and concentrated in vacuo. The residue was purified by silica gel chromatography (0-50% EtOAc in pet. ether) to afford ethyl (E)-3-(7-fluoroisoquinolin-6-yl)acrylate 39e as a yellow solid: $^1$H NMR (400 MHz, CDCl$_3$) δ 9.21 (s, 1H), 8.55 (d, J=5.7 Hz, 1H), 8.02 (d, J=7.0 Hz, 1H), 7.90 (d, J=16.2 Hz, 1H), 7.64 (t, J=9.0 Hz, 2H), 6.76 (d, J=16.2 Hz, 1H), 4.31 (q, J=7.1 Hz, 2H), 1.37 (t, J=7.1 Hz, 3H); ESI-HRMS calculated for C$_{14}$H$_{13}$FNO$_2$ (M+H$^+$) 246.0925, found 246.0931.

e) Procedure for the Preparation of 39f

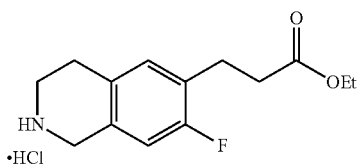 [SMILES: CCOC(=O)CCc1cc2c(cc1F)CNCC2 ; Cl]

A mixture of ethyl (E)-3-(7-fluoroisoquinolin-6-yl)acrylate 39e (1.9 g, 7.8 mmol), acetic acid (38 mL) and Pt—C (0.7 g, 0.2 mmol, 5% w/w) was heated overnight at 70° C. under atmosphere of hydrogen (balloon). The mixture was cooled to RT, filtered through celite and concentrated in vacuo. The residue was partitioned between EtOAc, added sat. NaHCO$_3$ solution (100 mL). The organic solution was washed with brine, dried over Na$_2$SO$_4$, filtered and concentrated in vacuo. The residue was dissolved in DCM and treated with 4 M HCl in dioxane solution (4.5 mL) at 0° C., then concentrated in vacuo to afford ethyl 3-(7-fluoro-1,2,3,4-tetrahydroisoquinolin-6-yl)propanoate hydrochloride 39f as a white solid: $^1$H NMR (400 MHz, CDCl$_3$) δ δ 10.18 (s, 2H), 7.03 (d, J=7.3 Hz, 1H), 6.80 (d, J=9.9 Hz, 1H), 4.30 (s, 2H), 4.13 (q, J=7.1 Hz, 2H), 3.42 (s, 2H), 3.10 (t, J=5.8 Hz, 2H), 2.93 (t, J=7.6 Hz, 2H), 2.60 (t, J=7.6 Hz, 2H), 1.24 (t, J=7.1 Hz, 3H), NH$_2^+$ not observed; ESI-HRMS calculated for C$_{14}$H$_{19}$FNO$_2$ (M+H$^+$) 252.1394, found 252.1400.

f) Procedure for the Preparation of 39g

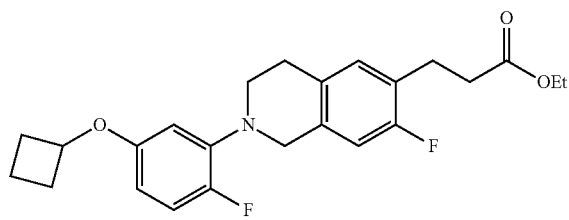 [SMILES: CCOC(=O)CCc1cc2c(cc1F)CN(c1cc(OC3CCC3)ccc1F)CC2]

A vial under argon was charged with ethyl 3-(7-fluoro-1,2,3,4-tetrahydroisoquinolin-6-yl)propanoate hydrochloride 39f (100 mg, 0.4 mmol), Cs$_2$CO$_3$ (450 mg, 1.4 mmol), Pd$_2$(dba)$_3$ (16 mg, 0.017 mmol), SPhos (20 mg, 0.05 mmol), 2-bromo-4-cyclobutoxy-1-fluorobenzene (115 mg, 0.470 mmol) and anhydrous dioxane (1.4 mL). The vial was sealed, evacuated and back filled with argon three times, then heated at 100° C. for 48 h. The mixture was cooled to RT, filtered through celite and concentrated in vacuo. The residue was purified by silica gel chromatography (1-5% EtOAc in pet. ether) to yield ethyl 3-(2-(5-cyclobutoxy-2-fluorophenyl)-7-fluoro-1,2,3,4-tetrahydroisoquinolin-6-yl)propanoate 39g as a colourless oil: $^1$H NMR (400 MHz, CDCl$_3$) δ δ 6.97 (d, J=7.6 Hz, 1H), 6.91 (dd, J=12.2, 8.8 Hz, 1H), 6.76 (d, J=10.4 Hz, 1H), 6.47 (dd, J=7.4, 2.9 Hz, 1H), 6.31 (dt, J=8.8, 3.1 Hz, 1H), 4.55 (p, J=6.8 Hz, 1H), 4.21 (s, 2H), 4.13 (q, J=7.1 Hz, 2H), 3.40 (t, J=5.9 Hz, 2H), 2.91 (dt, J=11.5, 6.7 Hz, 4H), 2.63-2.56 (m, 2H), 2.45-2.33 (m, 2H), 2.19-2.07 (m, 2H), 1.89-1.78 (m, 1H), 1.72-1.61 (m, 1H), 1.24 (t, J=7.1 Hz, 3H); ESI-HRMS calculated for C$_{24}$H$_{27}$F$_2$NO$_3$Na (M+Na$^+$) 438.1851, found 438.1854.

g) Procedure for the Preparation of 39 3-(2-(5-cyclobutoxy-2-fluorophenyl)-7-fluoro-1,2,3,4-tetrahydroisoquinolin-6-yl)propanoic Acid

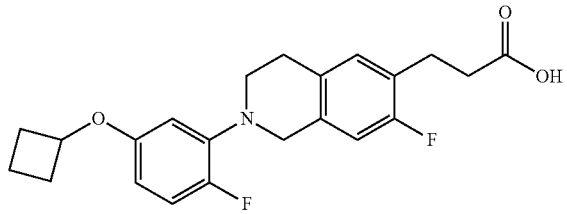 [SMILES: O=C(O)CCc1cc2c(cc1F)CN(c1cc(OC3CCC3)ccc1F)CC2]

A mixture of ethyl 3-(2-(5-cyclobutoxy-2-fluorophenyl)-7-fluoro-1,2,3,4-tetrahydroisoquinolin-6-yl)propanoate 39g (36 mg, 0.087 mmol) and LiOH.H$_2$O (11 mg, 0.26 mmol) in THF (0.6 mL) and water (0.3 mL) was stirred at RT overnight. The mixture was cooled to 0° C. and 1 M HCl (aq) was added until the mixture was acidified to pH 1. The mixture was warmed to RT and the product was extracted with EtOAc. The organic solution was washed with brine, dried over Na$_2$SO$_4$, filtered and concentrated in vacuo. The residue was purified by silica gel chromatography (0-30% EtOAc (with 1% AcOH) in pet. ether) to provide 3-(2-(5-cyclobutoxy-2-fluorophenyl)-7-fluoro-1,2,3,4-tetrahydroisoquinolin-6-yl)propanoic acid 39 as a white solid: $^1$H NMR (400 MHz, CDCl$_3$) δ 6.97 (d, J=7.6 Hz, 1H), 6.92 (dd, J=12.2, 8.8 Hz, 1H), 6.77 (d, J=10.4 Hz, 1H), 6.47 (dd, J=7.3, 2.9 Hz, 1H), 6.31 (dt, J=8.8, 3.1 Hz, 1H), 4.55 (p, J=6.8 Hz, 1H), 4.22 (s, 2H), 3.40 (t, J=5.8 Hz, 2H), 2.92 (dt, J=11.4, 6.7 Hz, 4H), 2.68 (t, J=7.7 Hz, 2H), 2.44-2.35 (m, 2H), 2.19-2.07 (m, 2H), 1.89-1.78 (m, 1H), 1.74-1.59 (m, 1H), —COOH not observed; ESI-HRMS calculated for C$_{22}$H$_{24}$F$_2$NO$_3$ (M+H$^+$) 388.1719, found 388.1715.

Human GPR120 pEC50: 7.2

The following compounds were prepared using appropriate starting materials in analogous procedure to that described in Experimental Scheme 13. Where the starting materials are not described in the literature, their synthesis is described below.

| Compound | Structure | [M + H]+ | NMR | hGPR120 pEC50 |
|---|---|---|---|---|
| 40 | 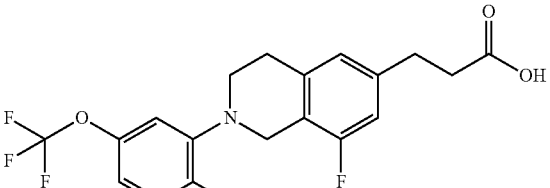  3-(8-fluoro-2-(2-fluoro-5-(trifluoromethoxy)phenyl)-1,2,3,4-tetrahydroisoquinolin-6-yl)propanoic acid | 402 | (CDCl$_3$) δ 7.04 (dd, J = 11.9, 8.8 Hz, 1H), 6.85 (dd, J = 7.1, 2.7 Hz, 1H), 6.81 (s, 1H), 6.80-6.74 (m, 2H), 4.24 (s, 2H), 3.41 (t, J = 5.7 Hz, 2H), 2.96 (t, J = 5.7 Hz, 2H), 2.91 (t, J = 7.7 Hz, 2H), 2.64 (t, J = 7.7 Hz, 2H) —COOH not observed | 7.5 |
| 41 | 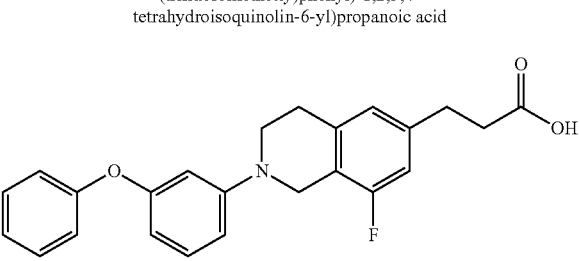  3-(8-fluoro-2-(3-phenoxyphenyl)-1,2,3,4-tetrahydroisoquinolin-6-yl)propanoic acid | 392 | (CDCl$_3$) δ 7.35-7.29 (m, 2H), 7.22 (t, J = 8.2 Hz, 1H), 7.11-7.05 (m, 1H), 7.04-7.00 (m, 2H), 6.79 (s, 1H), 6.78-6.72 (m, 2H), 6.69 (t, J = 2.3 Hz, 1H), 6.44 (dd, J = 8.0, 1.8 Hz, 1H), 4.35 (s, 2H), 3.52 (t, J = 5.8 Hz, 2H), 2.97-2.87 (m, 4H), 2.66 (t, J = 7.7 Hz, 2H) —COOH not observed | 7.5 |

Intermediate 7 (I-7)

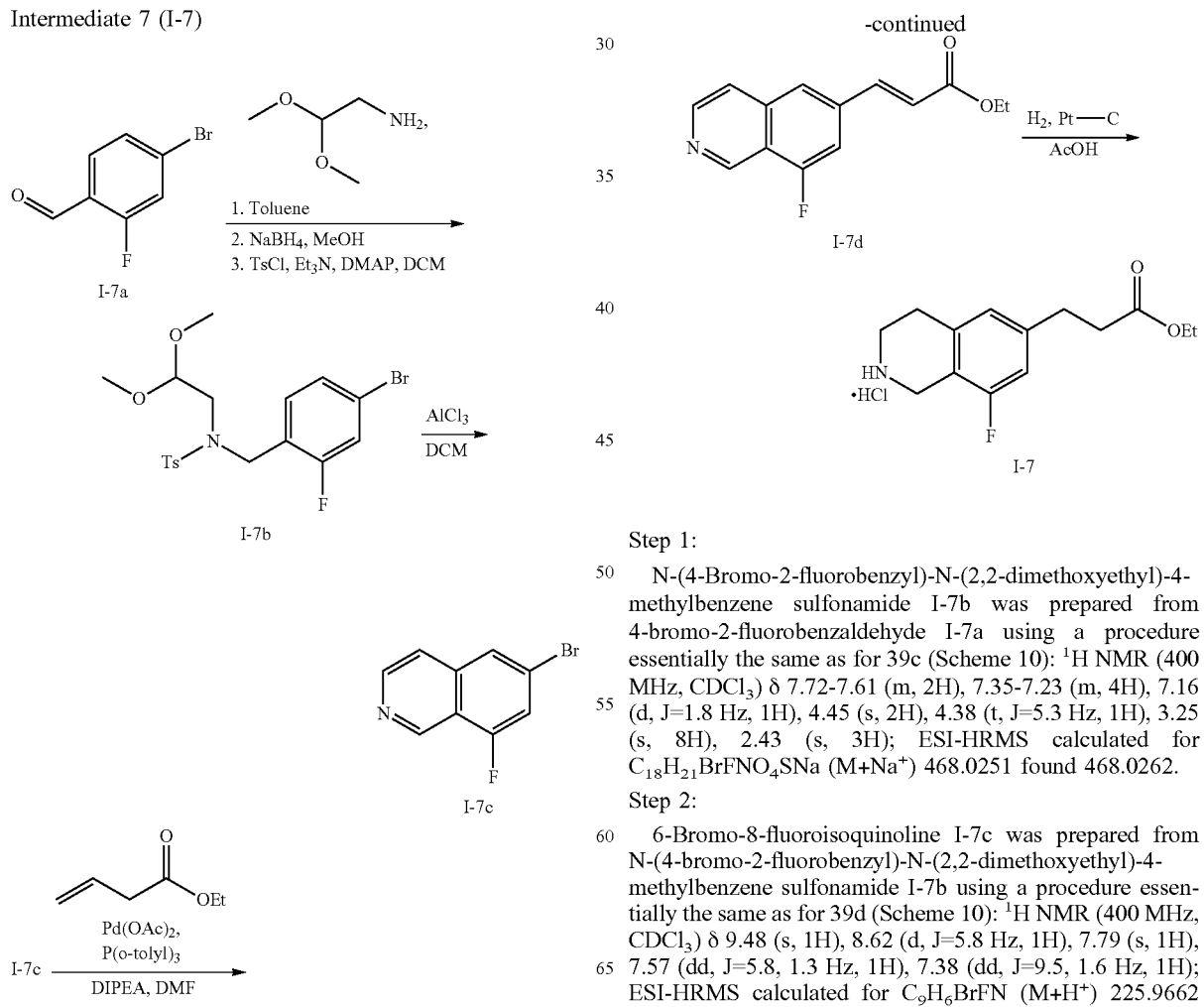

Step 1:

N-(4-Bromo-2-fluorobenzyl)-N-(2,2-dimethoxyethyl)-4-methylbenzene sulfonamide I-7b was prepared from 4-bromo-2-fluorobenzaldehyde I-7a using a procedure essentially the same as for 39c (Scheme 10): $^1$H NMR (400 MHz, CDCl$_3$) δ 7.72-7.61 (m, 2H), 7.35-7.23 (m, 4H), 7.16 (d, J=1.8 Hz, 1H), 4.45 (s, 2H), 4.38 (t, J=5.3 Hz, 1H), 3.25 (s, 8H), 2.43 (s, 3H); ESI-HRMS calculated for C$_{18}$H$_{21}$BrFNO$_4$SNa (M+Na$^+$) 468.0251 found 468.0262.

Step 2:

6-Bromo-8-fluoroisoquinoline I-7c was prepared from N-(4-bromo-2-fluorobenzyl)-N-(2,2-dimethoxyethyl)-4-methylbenzene sulfonamide I-7b using a procedure essentially the same as for 39d (Scheme 10): $^1$H NMR (400 MHz, CDCl$_3$) δ 9.48 (s, 1H), 8.62 (d, J=5.8 Hz, 1H), 7.79 (s, 1H), 7.57 (dd, J=5.8, 1.3 Hz, 1H), 7.38 (dd, J=9.5, 1.6 Hz, 1H); ESI-HRMS calculated for C$_9$H$_6$BrFN (M+H$^+$) 225.9662 found 225.9672.

Step 3:

Ethyl (E)-3-(8-fluoroisoquinolin-6-yl)acrylate I-7d was prepared from 6-bromo-8-fluoroisoquinoline I-7c using a procedure essentially the same as for 39e (Scheme 10): $^1$H NMR (400 MHz, CDCl$_3$) δ 9.52 (s, 1H), 8.65 (d, J=5.8 Hz, 1H), 7.78 (dd, J=16.0, 1.1 Hz, 1H), 7.70 (s, 1H), 7.68 (dd, J=5.8, 1.3 Hz, 1H), 7.42 (dd, J=11.1, 1.3 Hz, 1H), 6.56 (d, J=16.0 Hz, 1H), 4.31 (q, J=7.1 Hz, 2H), 1.37 (t, J=7.1 Hz, 3H); ESI-HRMS calculated for C$_{14}$H$_{13}$FNO$_2$ (M+H$^+$) 246.0925 found 246.0919.

Step 4:

Ethyl 3-(8-fluoro-1,2,3,4-tetrahydroisoquinolin-6-yl)propanoate hydrochloride I-7 was prepared from ethyl (E)-3-(8-fluoroisoquinolin-6-yl)acrylate I-7d using a procedure essentially the same as for 39f (Scheme 10): m/z 252 [M+H]$^+$ (APCI$^+$); $^1$H NMR (400 MHz, CDCl$_3$) δ 10.27 (br s, 2H), 6.85-6.79 (m, 2H), 4.32 (s, 2H), 4.13 (q, J=7.1 Hz, 2H), 3.49-3.41 (m, 2H), 3.17 (t, J=5.8 Hz, 2H), 2.90 (t, J=7.6 Hz, 2H), 2.59 (t, J=7.6 Hz, 2H), 1.25 (t, J=7.1 Hz, 3H).

Experimental Scheme 11

Compound 423-(2-(3-Cyclobutoxy-5-fluorophenyl)-7-fluoro-1,2,3,4-tetrahydroisoquinolin-6-yl)propanoic Acid

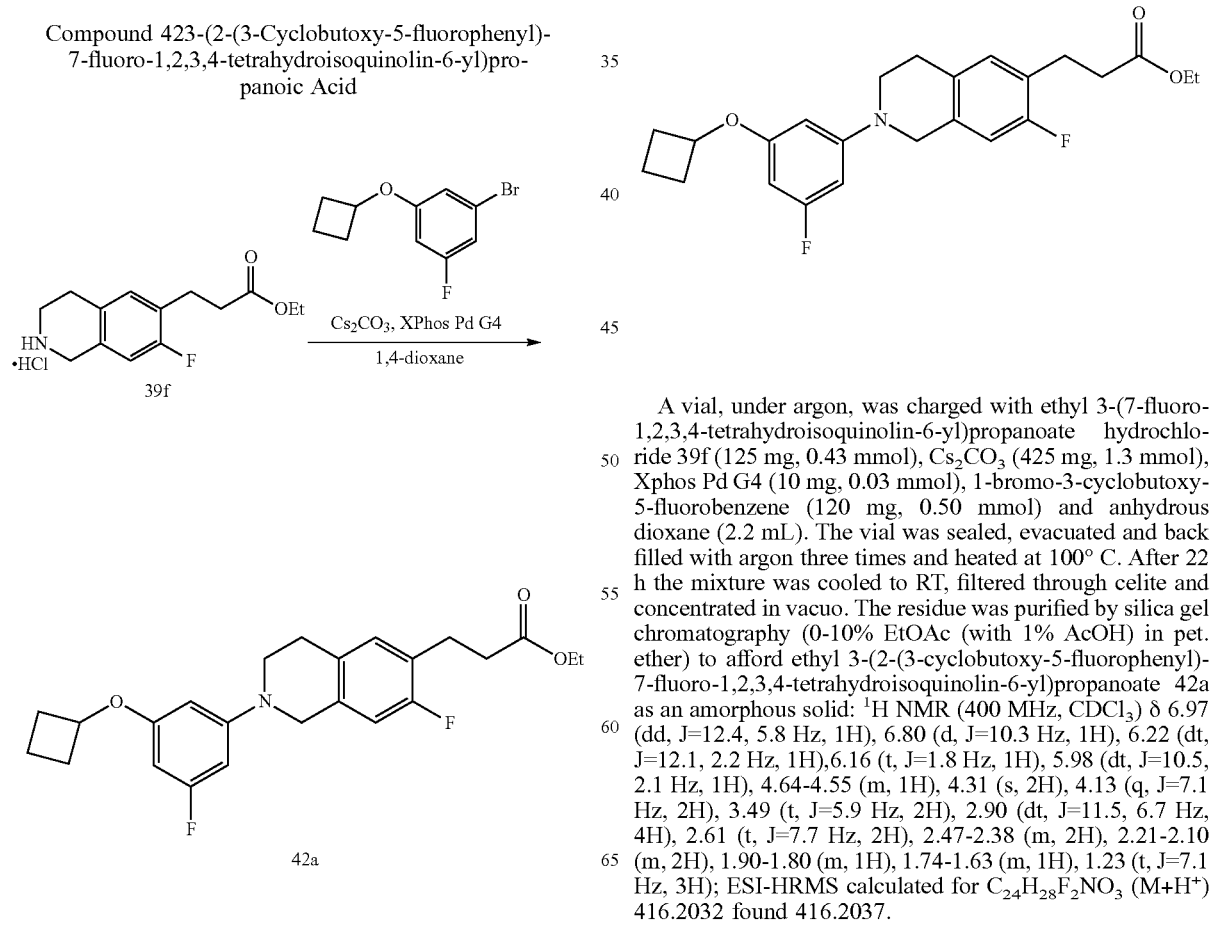

a) Procedure for the Preparation of 42a

A vial, under argon, was charged with ethyl 3-(7-fluoro-1,2,3,4-tetrahydroisoquinolin-6-yl)propanoate hydrochloride 39f (125 mg, 0.43 mmol), Cs$_2$CO$_3$ (425 mg, 1.3 mmol), Xphos Pd G4 (10 mg, 0.03 mmol), 1-bromo-3-cyclobutoxy-5-fluorobenzene (120 mg, 0.50 mmol) and anhydrous dioxane (2.2 mL). The vial was sealed, evacuated and back filled with argon three times and heated at 100° C. After 22 h the mixture was cooled to RT, filtered through celite and concentrated in vacuo. The residue was purified by silica gel chromatography (0-10% EtOAc (with 1% AcOH) in pet. ether) to afford ethyl 3-(2-(3-cyclobutoxy-5-fluorophenyl)-7-fluoro-1,2,3,4-tetrahydroisoquinolin-6-yl)propanoate 42a as an amorphous solid: $^1$H NMR (400 MHz, CDCl$_3$) δ 6.97 (dd, J=12.4, 5.8 Hz, 1H), 6.80 (d, J=10.3 Hz, 1H), 6.22 (dt, J=12.1, 2.2 Hz, 1H), 6.16 (t, J=1.8 Hz, 1H), 5.98 (dt, J=10.5, 2.1 Hz, 1H), 4.64-4.55 (m, 1H), 4.31 (s, 2H), 4.13 (q, J=7.1 Hz, 2H), 3.49 (t, J=5.9 Hz, 2H), 2.90 (dt, J=11.5, 6.7 Hz, 4H), 2.61 (t, J=7.7 Hz, 2H), 2.47-2.38 (m, 2H), 2.21-2.10 (m, 2H), 1.90-1.80 (m, 1H), 1.74-1.63 (m, 1H), 1.23 (t, J=7.1 Hz, 3H); ESI-HRMS calculated for C$_{24}$H$_{28}$F$_2$NO$_3$ (M+H$^+$) 416.2032 found 416.2037.

b) Procedure for the Preparation of 42 3-(2-(3-Cyclobutoxy-5-fluorophenyl)-7-fluoro-1,2,3,4-tetrahydroisoquinolin-6-yl)propanoic Acid

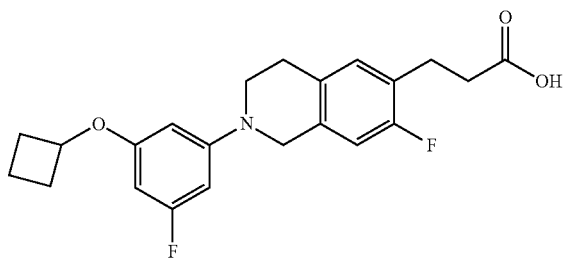 [SMILES: O=C(O)CCc1cc2c(cc1F)CN(c1cc(F)cc(OC3CCC3)c1)CC2]

3-(2-(3-Cyclobutoxy-5-fluorophenyl)-7-fluoro-1,2,3,4-tetrahydroisoquinolin-6-yl)propanoic acid 42 was prepared from ethyl 3-(2-(3-cyclobutoxy-5-fluorophenyl)-7-fluoro-1,2,3,4-tetrahydroisoquinolin-6-yl)propanoate 42a using a procedure essentially the same as for compound 39: $^1$H NMR (400 MHz, CDCl$_3$) δ 6.99 (d, J=7.5 Hz, 1H), 6.81 (d, J=10.2 Hz, 1H), 6.22 (d, J=12.1 Hz, 1H), 6.16 (s, 1H), 6.02-5.95 (m, 1H), 4.60 (p, J=7.2 Hz, 1H), 4.31 (s, 2H), 3.50 (t, J=5.8 Hz, 2H), 2.95 (t, J=7.7 Hz, 2H), 2.88 (t, J=5.7 Hz, 2H), 2.68 (t, J=7.7 Hz, 2H), 2.48-2.38 (m, 2H), 2.22-2.09 (m, 2H), 1.91-1.80 (m, 1H), 1.75-1.61 (m, 1H), —COOH not observed; ESI-HRMS calculated for C22H24F2NO3 (M+H$^+$) 388.1719 found 388.1715.

Human GPR120 pEC50: 6.5

The following compounds were prepared using appropriate starting materials in an analogous procedure to that described in Experimental Scheme 11.

Where the starting materials are not described in the literature, their synthesis is described below.

| Compound | Structure | [M + H]+ | NMR | hGPR120 pEC50 |
|---|---|---|---|---|
| 43 | 3-(2-(3-chloro-5-cyclobutoxyphenyl)-1,2,3,4-tetrahydroisoquinolin-6-yl)propanoic acid | 386 | (CDCl$_3$) δ 7.10-6.99 (m, 3H), 6.51 (app t, J = 1.9 Hz, 1H), 6.27 (app t, J = 2.2 Hz, 1H), 6.23 (app t, J = 1.9 Hz, 1H), 4.65-4.56 (m, 1H), 4.34 (s, 2H), 3.50 (t, J = 5.9 Hz, 2H), 2.96-2.90 (m, 4H), 2.68 (t, J = 7.8 Hz, 2H), 2.48-2.39 (m, 2H), 2.22-2.08 (m, 2H), 1.91-1.80 (m, 1H), 1.75-1.61 (m, 1H), —COOH not observed. | 7.7 |

Intermediate 8 (I-8)

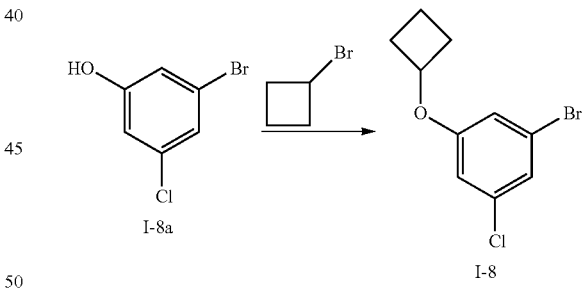

A vial was charged with K$_2$CO$_3$ (2.07 g, 15 mmol), DMF (5 mL), 3-bromo-5-chlorophenol I-8a (1.57 g, 7.5 mmol) and KI (620 mg, 3.75 mmol) and the mixture was stirred at RT for 10 min. Bromocyclobutane (1.06 ml, 11.3 mmol) was added and the mixture was heated at 90° C. for 20 h. The reaction was cooled to RT, filtered through a plug of silica (EtOAc), diluted with water and the product was extracted with EtOAc (×3). The combined organic phases were washed with brine, dried with Na$_2$SO$_4$, filtered and concentrated in vacuo. The residue was purified by chromatography on silica (pet. ether) to afford 1-bromo-3-chloro-5-cyclobutoxybenzene I-8 as a colourless oil: 1H NMR (400 MHz, CDCl$_3$) δ 7.08-7.06 (m, 1H), 6.86-6.84 (m, 1H), 6.74-6.73 (m, 1H), 4.63-4.54 (m, 1H), 2.49-2.40 (m, 2H), 2.20-2.08 (m, 2H), 1.93-1.82 (m, 1H), 1.75-1.62 (m, 1H)

Experimental Scheme 12

Compound 44 3-(2-(6-Cyclobutoxy-3,5-difluoropyridin-2-yl)-1,2,3,4-tetrahydroisoquinolin-6-yl)propanoic Acid

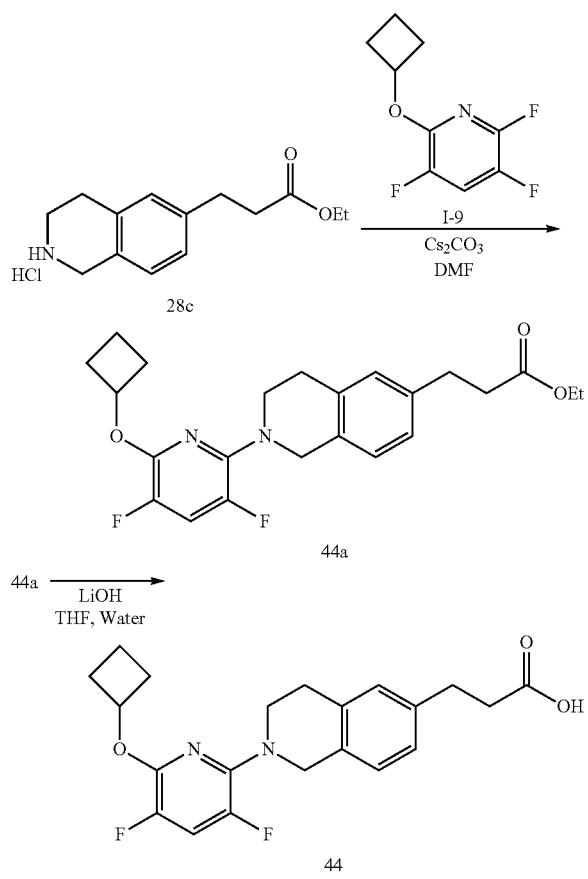

a) Procedure for the Preparation of 44a

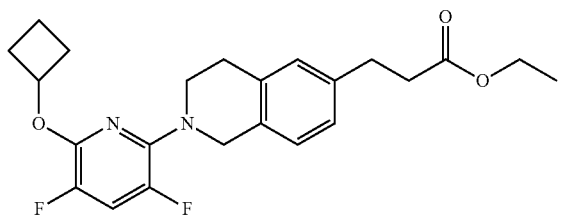 [SMILES: CCOC(=O)CCc1ccc2c(c1)CCN(c1nc(OC3CCC3)c(F)cc1F)C2]

A vial was charged with ethyl 3-(1,2,3,4-tetrahydroisoquinolin-6-yl)propanoate hydrochloride 28c (103 mg, 0.38 mmol), Cs₂CO₃ (259 mg, 0.79 mmol), 2-cyclobutoxy-3,5,6-trifluoropyridine I-9 (116 mg, 0.57 mmol) and DMF (1 mL). The mixture was heated at 100° C. for 20 h. The reaction was cooled to RT and filtered through a plug of silica (eluent EtOAc). The filtrate was diluted with water and the product was extracted with EtOAc (3×). The combined organic phases were washed with brine, dried over Na₂SO₄, filtered and concentrated in vacuo. The residue was purified by chromatography on silica (0-5% EtOAc in pet. ether) to afford ethyl 3-(2-(6-cyclobutoxy-3,5-difluoropyridin-2-yl)-1,2,3,4-tetrahydroisoquinolin-6-yl)propanoate 44a as a colourless oil: ¹H NMR (400 MHz, CDCl₃) δ 7.12 (dd, J=11.0, 8.9 Hz, 1H), 7.08-6.96 (m, 3H), 5.16-5.05 (m, 1H), 4.55 (s, 2H), 4.13 (q, J=7.1 Hz, 2H), 3.69 (t, J=5.9 Hz, 2H), 2.97-2.88 (m, 4H), 2.63-2.58 (m, 2H), 2.47-2.38 (m, 2H), 2.25-2.13 (m, 2H), 1.90-1.80 (m, 1H), 1.75-1.63 (m, 1H), 1.24 (t, J=7.1 Hz, 3H);

b) Procedure for the Preparation of 44 3-(2-(6-Cyclobutoxy-3,5-difluoropyridin-2-yl)-1,2,3,4-tetrahydroisoquinolin-6-yl)propanoic Acid

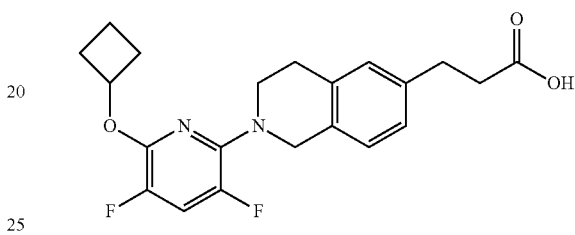

3-(2-(6-Cyclobutoxy-3,5-difluoropyridin-2-yl)-1,2,3,4-tetrahydroisoquinolin-6-yl)propanoic acid 44 was prepared from ethyl 3-(2-(6-cyclobutoxy-3,5-difluoropyridin-2-yl)-1,2,3,4-tetrahydroisoquinolin-6-yl)propanoate 44a using a procedure essentially the same as for compound 29. The product was purified by column chromatography (0-25% (0.01% AcOH in EtOAc) in pet. ether) to afford 3-(2-(6-Cyclobutoxy-3,5-difluoropyridin-2-yl)-1,2,3,4-tetrahydroisoquinolin-6-yl)propanoic acid 44 as a white solid: ¹H NMR (400 MHz, CDCl₃) δ δ 7.13 (dd, J=11.0, 8.9 Hz, 1H), 7.09-6.97 (m, 3H), 5.16-5.05 (m, 1H), 4.55 (s, 2H), 3.70 (t, J=5.9 Hz, 2H), 2.95-2.89 (m, 4H), 2.71-2.64 (m, 2H), 2.46-2.37 (m, 2H), 2.25-2.13 (m, 2H), 1.90-1.80 (m, 1H), 1.75-1.62 (m, 1H)—COOH not observed; ESI-HRMS calcd for $C_{21}H_{23}F_2N_2O_3$ (M+H⁺) 389.1671, found 389.1671.

Human GPR120 pEC₅₀: 7.6

Intermediate 9 (I-9)

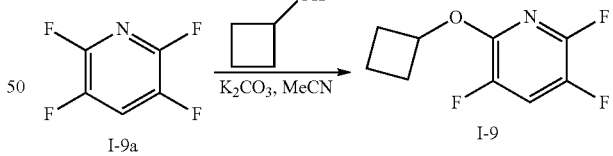

A vial was charged with K₂CO₃ (1.10 g, 7.94 mmol), MeCN (10 mL), 2,3,5,6-tetrafluoropyridine I-9a (0.66 mL, 6.6 mmol), cyclobutanol (0.52 mL, 6.6 mmol) and the mixture was stirred at RT for 18 h. An additional portion of cyclobutanol (0.4 mL, 5.1 mmol) was added and the mixture was heated at 120° C. for 3 days. The reaction was cooled to RT, filtered through a plug of silica (eluent EtOAc) and concentrated in vacuo. The residue was purified by chromatography on silica (pet. ether) to afford 2-cyclobutoxy-3,5,6-trifluoropyridine I-9 as a colourless oil: ¹H NMR (400 MHz, CDCl₃) δ δ 7.36 (td, J=8.1, 7.2 Hz, 1H), 5.17-5.09 (m, 1H), 2.53-2.43 (m, 2H), 2.25-2.12 (m, 2H), 1.92-1.81 (m, 1H), 1.75-1.62 (m, 1H)

Experimental Scheme 13

Compound 45 3-(3-(2-fluoro-5-(trifluoromethoxy)phenyl)-2,3,4,5-tetrahydro-1H-benzo[d]azepin-7-yl)propanoic acid

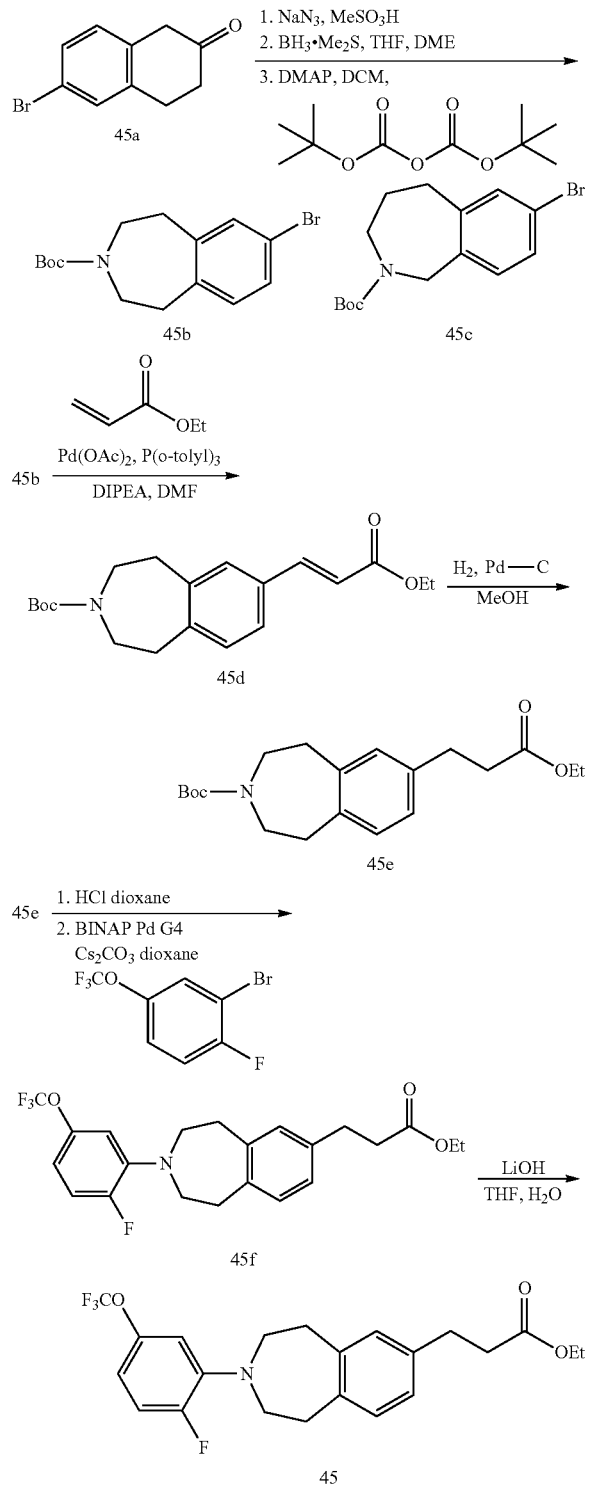

a) Procedure for the Preparation of 45b and 45c

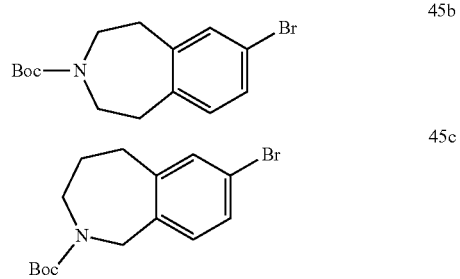

Step 1a:

NaN$_3$ (0.36 g, 5.6 mmol) was cautiously added to a solution of 6-bromo-3,4-dihydronaphthalen-2(1H)-one 45a (1.0 g, 4.4 mmol) in methanesulfonic acid (5 mL) at 0° C. The reaction mixture was warmed to RT overnight. The mixture was poured onto a mixture of 1 M KOH and ice and the product was extracted with EtOAc. The organic solution was washed with brine, dried over Na$_2$SO$_4$ and filtered. The solution was concentrated in vacuo to provide a 1:1 mixture of 7-bromo-1,3,4,5-tetrahydro-2H-benzo[d]azepin-2-one and 7-bromo-1,2,4,5-tetrahydro-3H-benzo[c]azepin-3-one that was taken on without purification.

Step 1b:

Borane.dimethylsulfide complex (1 M, 8.9 mL, 8.9 mmol) was added dropwise to a solution of the mixture obtained in step 1a in DME (5 mL) at 0° C. The mixture was heated at reflux, under argon overnight then cooled to 0° C. The reaction was quenched by the addition of MeOH and the solution was concentrated in vacuo to afford a mixture of 7-bromo-2,3,4,5-tetrahydro-1H-benzo[d]azepine and 7-bromo-2,3,4,5-tetrahydro-1H-benzo[c]azepine which was taken on to the next step without purification.

Step 1c:

The mixture from step 1b was dissolved in anhydrous DCM (10 mL) and the solution was cooled to 0° C. before the sequential addition of Et$_3$N (1.2 g, 12 mmol), DMAP (57 mg, 0.47 mmol) and di-tert-butyl dicarbonate (1.3 g, 6.1 mmol). The mixture was stirred at RT overnight, then the product was extracted with DCM. The organic solution was washed with 1M HCl and brine, dried over Na$_2$SO$_4$, filtered and concentrated in vacuo. The residue was purified by silica gel chromatography (0-10% EtOAc in pet. ether) to yield tert-butyl 7-bromo-1,2,4,5-tetrahydro-3H-benzo[d]azepine-3-carboxylate 45b and tert-butyl 7-bromo-1,3,4,5-tetrahydro-2H-benzo[c]azepine-2-carboxylate 45c as clear oils: 45b: $^1$H NMR (500 MHz, CDCl$_3$) δ 7.27-7.23 (m, 2H), 6.98 (d, J=7.9 Hz, 1H), 3.53 (q, J=5.4 Hz, 4H), 2.88-2.79 (m, 4H), 1.47 (s, 9H); ESI-HRMS calculated for C$_{15}$H$_{20}$BrNNaO$_2$ (M+Na$^+$) 348.0570 found 348.0572. 45c: $^1$H NMR (500 MHz, CDCl$_3$) δ 7.32 (br s, 1H), 7.30-7.25 (m, 2H), 4.35 (br s, 2H), 3.70 (br s, 2H), 2.96-2.89 (m, 2H), 1.78 (s, 2H), 1.41 (s, 9H). 3.73-3.61 (m, 2H), 2.93-2.87 (m, 2H), 1.81-1.70 (m, 2H), 1.38 (s, 9H); ESI-HRMS calculated for C$_{15}$H$_{20}$BrNNaO$_2$ (M+Na$^+$) 348.0570, found 348.0558.

d) Procedure for the Preparation of 45d

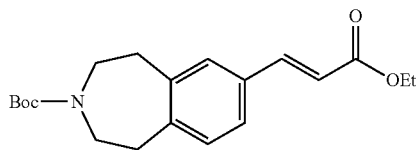 [SMILES: CCOC(=O)/C=C/c1ccc2c(c1)CCN(C(=O)OC(C)(C)C)CC2]

tert-Butyl 7-bromo-1,2,4,5-tetrahydro-3H-benzo[d]azepine-3-carboxylate 45b (170 mg, 0.52 mmol), palladium (II) acetate (2.9 mg, 2.5 mol %) and tri-o-tolylphosphine (7.9 mg, 5.0 mol %) were placed in a sealed vial, which was then evacuated and back-filled with argon three times. Ethyl acrylate (63 mg, 0.63 mmol) and a solution of DMF: DIPEA (1:1, 2 ml) were added and the mixture was heated in a microwave reactor at 120° C. for 30 minutes. The reaction was cooled to RT and water was added. The product was extracted with diethylether. The combined organic phases were washed with 1M HCl, brine, dried over $Na_2SO_4$, filtered and concentrated in vacuo. The residue was purified by silica gel chromatography (0-20% EtOAc in pet. ether) to afford tert-butyl (E)-7-(3-ethoxy-3-oxoprop-1-en-1-yl)-1,2,4,5-tetrahydro-3H-benzo[d]azepine-3-carboxylate 45d as a clear oil: $^1$H NMR (500 MHz, $CDCl_3$) δ 7.66 (d, J=16.0 Hz, 1H), 7.34-7.29 (m, 2H), 7.15 (d, J=7.7 Hz, 1H), 6.42 (d, J=16.0 Hz, 1H), 4.28 (q, J=7.1 Hz, 2H), 3.58 (d, J=6.6 Hz, 4H), 2.98-2.84 (m, 4H), 1.47 (d, J=7.2 Hz, 9H), 1.36 (t, J=7.1 Hz, 3H); ESI-HRMS calcd for $C_{20}H_{27}NNaO_4$ (M+Na$^+$) 368.1832, found 368.1846.

e) Procedure for the Preparation of 45e

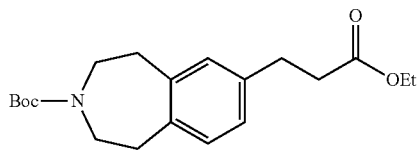 [SMILES: CCOC(=O)CCc1ccc2c(c1)CCN(C(=O)OC(C)(C)C)CC2]

Pd/C (110 mg, 10 mol %) was added to a solution of tert-Buty (E)-7-(3-ethoxy-3-oxoprop-1-en-1-yl)-1,3,4,5-tetrahydro-3H-benzo[d]azepine-3-carboxylate 45d (712 mg, 2.06 mmol) in MeOH (5 ml). The mixture was flushed with argon for 15 minutes and stirred under a hydrogen atmosphere for 16 h. The mixture was filtered through a pad of celite and the filtrate was concentrated in vacuo. The residue was purified by chromatography on silica (0-20% EtOAc/petroleum ether) to afford tert-butyl 7-(3-ethoxy-3-oxopropyl)-1,2,4,5-tetrahydro-3H-benzo[d]azepine-3-carboxylate 45e as a clear oil: $^1$H NMR (400 MHz, $CDCl_3$) δ 7.04-6.99 (m, 1H), 6.97-6.92 (m, 2H), 4.12 (q, J=7.1 Hz, 2H), 3.52 (broad s, 4H), 2.91-2.80 (m, 6H), 2.61-2.56 (m, 2H), 1.47 (s, 9H), 1.23 (t, J=7.2 Hz, 3H); ESI-HRMS calcd for $C_{20}H_{29}NNaO_4$ (M+Na$^+$) 370.1989, found 370.1999.

f) Procedure for the Preparation of 45f

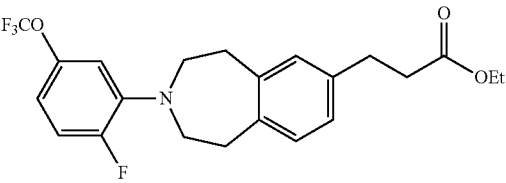 [SMILES: CCOC(=O)CCc1ccc2c(c1)CCN(c1cc(OC(F)(F)F)ccc1F)CC2]

Step 1.
tert-Butyl 7-(3-ethoxy-3-oxopropyl)-1,2,4,5-tetrahydro-3H-benzo[d]azepine-3-carboxylate 45e (570 mg, 1.6 mmol) was added to a solution of HCl in 1,4-dioxane (4 M, 10 ml). The mixture was stirred at room temperature for 16 h and then concentrated in vacuo to afford ethyl 3-(2,3,4,5-tetrahydro-1H-benzo[d]azepin-7-yl)propanoate hydrochloride, which was taken on to the next step without purification.
Step 2.
A vial under argon was charged with ethyl 3-(2,3,4,5-tetrahydro-1H-benzo[d]azepin-7-yl)propanoate hydrochloride (30 mg, 0.11 mmol), 2-bromo-1-fluoro-4-(trifluoromethoxy)benzene (41 mg, 0.16 mmol), cesium carbonate (121 mg, 0.37 mmol), Pd-BINAP G4 precatalyst (5 mg, 4 mol %) and anhydrous dioxane (2 ml). The vial was sealed, evacuated and back filled with argon three times, then heated at 100° C. for 48 h. The reaction was cooled and water was added. The product was extracted with EtOAc (3×). The combined organic phases were washed with brine and dried over $Na_2SO_4$, filtered and concentrated in vacuo. The residue was purified by silica gel chromatography (5% EtOAc in petroleum ether) to afford ethyl 3-(3-(2-fluoro-5-(trifluoromethoxy)phenyl)-2,3,4,5-tetrahydro-1H-benzo[d]azepin-7-yl)propanoate 45f as a clear oil: $^1$H NMR (400 MHz, $CDCl_3$) δ 7.08-7.02 (m, 1H), 7.01-6.96 (m, 3H), 6.79-6.74 (m, 1H), 6.74-6.68 (m, 1H), 4.14 (q, J=7.1 Hz, 2H), 3.35-3.29 (m, 4H), 3.06-3.00 (m, 4H), 2.94-2.88 (m, 2H), 2.64-2.58 (m, 2H), 1.24 (t, J=7.1 Hz, 3H); ESI-HRMS calcd for $C_{22}H_{24}F_4NO_3$ (M+H$^+$) 426.1687, found 426.1678.

f) Procedure for the Preparation of 45 3-(3-(2-fluoro-5-(trifluoromethoxy)phenyl)-2,3,4,5-tetrahydro-1H-benzo[d]azepin-7-yl)propanoic Acid

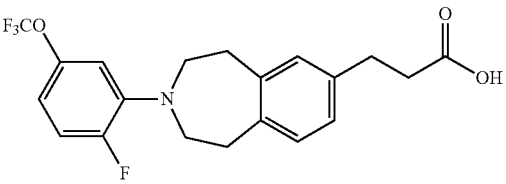 [SMILES: O=C(O)CCc1ccc2c(c1)CCN(c1cc(OC(F)(F)F)ccc1F)CC2]

A solution of aqueous lithium hydroxide (0.6 M, 0.5 ml) was added to a solution of ethyl 3-(3-(2-fluoro-5-(trifluoromethoxy)phenyl)-2,3,4,5-tetrahydro-1H-benzo[d]azepin-7-yl)propanoate 45f (8 mg, 0.02 mmol) in THF (1 ml) and the mixture was stirred for 16 h at RT. 1M HCl was added until the mixture was acidified to pH 3. The product was extracted with EtOAc (3×) and the combined organic phases were washed with brine and dried over $Na_2SO_4$, filtered and concentrated in vacuo to afford 3-(3-(2-fluoro-5-(trifluoromethoxy)phenyl)-2,3,4,5-tetrahydro-1H-benzo[d]azepin- 7-yl)propanoic acid as an amorphous solid: $^1$H NMR (400 MHz, CDCl$_3$) δ 7.07 (d, J=7.7 Hz, 1H), 7.04-6.96 (m, 3H), 6.79-6.74 (m, 1H), 6-74-6.68 (m, 1H), 3.36-3.29 (m, 4H), 3.07-3.00 (m, 4H), 2.93 (t, J=7.8 Hz, 2H), 2.68 (t, J=7.8 Hz, 2H), COOH not observed; ESI-HRMS calcd for C$_{20}$H$_{20}$F$_4$NO$_3$ (M+H$^+$) 398.1374, found 398.1383.

Human GPR120 pEC$_{50}$: 7.6

The following compounds were prepared using appropriate starting materials in an analogous procedure to that described in Experimental Scheme 13.

Where the starting materials are not described in the literature, their synthesis is described below.

| Compound | Structure | [M + H]+ | NMR | hGPR120 pEC50 |
|---|---|---|---|---|
| 46 | 3-(3-(5-cyclobutoxy-2-fluorophenyl)-2,3,4,5-tetrahydro-1H-benzo[d]azepin-7-yl)propanoic acid | 384 | (CDCl$_3$) δ 7.01 (d, J = 8.2 Hz, 1H), 7.01-6.97 (m, 2H), 6.92-6.86 (m, 1H), 6.46-6.41 (m, 1H), 6.30-6.24 (m, 1H), 4.59-4.50 (m, 1H), 3.31-3.25 (m, 4H), 3.06-3.00 (m, 4H), 2.96-2.90 (m, 2H), 2.72-2.65 (m, 2H), 2.45-2.36 (m, 2H), 2.20-2.08 (m, 2H), 1.88-1.80 (m, 1H), 1.70-1.60 (m, 1H), COOH not observed | 7.1 |
| 47 | 3-(3-(5-cyclopropoxy-2-fluorophenyl)-2,3,4,5-tetrahydro-1H-benzo[d]azepin-7-yl)propanoic acid | 370 | (CDCl$_3$) δ 7.08-7.03 (m, 1H), 7.03-6.89 (m, 3H), 6.62-6.56 (m, 2H), 3.69-3.63 (m, 1H), 3.32-3.24 (m, 4H), 3.06-2.99 (m, 4H), 2.92 (t, J = 7.8 Hz, 2H), 2.71-2.63 (m, 2H), 0.74 (d, J = 4.5 Hz, 4H) COOH not observed | 6.8 |
| 48 | 3-(3-(2-fluoro-5-isopropoxyphenyl)-2,3,4,5-tetrahydro-1H-benzo[d]azepin-7-yl)propanoic acid | 372 | (CDCl$_3$) δ 7.09-7.04 (m, 1H), 7.02-6.96 (m, 2H), 6.94-6.87 (m, 1H), 6.52-6.46 (m, 1H), 6.41-6.35 (m, 1H), 4.48-4.37 (m, 1H), 3.32-3.24 (m, 4H), 3.07-2.99 (m, 4H), 2.93 (t, J = 7.8 Hz, 2H), 2.72-2.65 (m, 2H), 1.31 (d, J = 5.8 Hz, 6H), COOH not observed | 6.7 |
| 49 | 3-(3-(3-fluoro-5-isopropoxyphenyl)-2,3,4,5-tetrahydro-1H-benzo[d]azepin-7-yl)propanoic acid | 372 | (CDCl$_3$) δ 7.05-7.00 (m, 1H), 6.98-6.93 (m, 2H), 6.20-6.13 (m, 2H), 6.05-5.99 (m, 1H), 4.54-4.44 (m, 1H), 3.63-3.56 (m, 4H), 2.97-2.87 (m, 6H), 2.71-2.63 (m, 2H), 1.34 (d, J = 6.1 Hz, 6H), COOH not observed. | 6.4 |

| Compound | Structure | [M + H]+ | NMR | hGPR120 pEC50 |
|---|---|---|---|---|
| 50 | 3-(3-(2-fluoro-5-phenoxyphenyl)-2,3,4,5-tetrahydro-1H-benzo[d]azepin-7-yl)propanoic acid | 406 | (CDCl$_3$) δ 7.35-7.27 (m, 2H), 7.11-6.92 (m, 7H), 6.68-6.61 (m, 1H), 6.53-6.45 (m, 1H), 3.34-3.24 (m, 4H), 3.08-2.97 (m, 4H), 2.92 (t, J = 7.8 Hz, 2H), 2.68 (t, J = 7.8 Hz, 2H), COOH not observed | 7.6 |

Intermediate 10 (I-10)

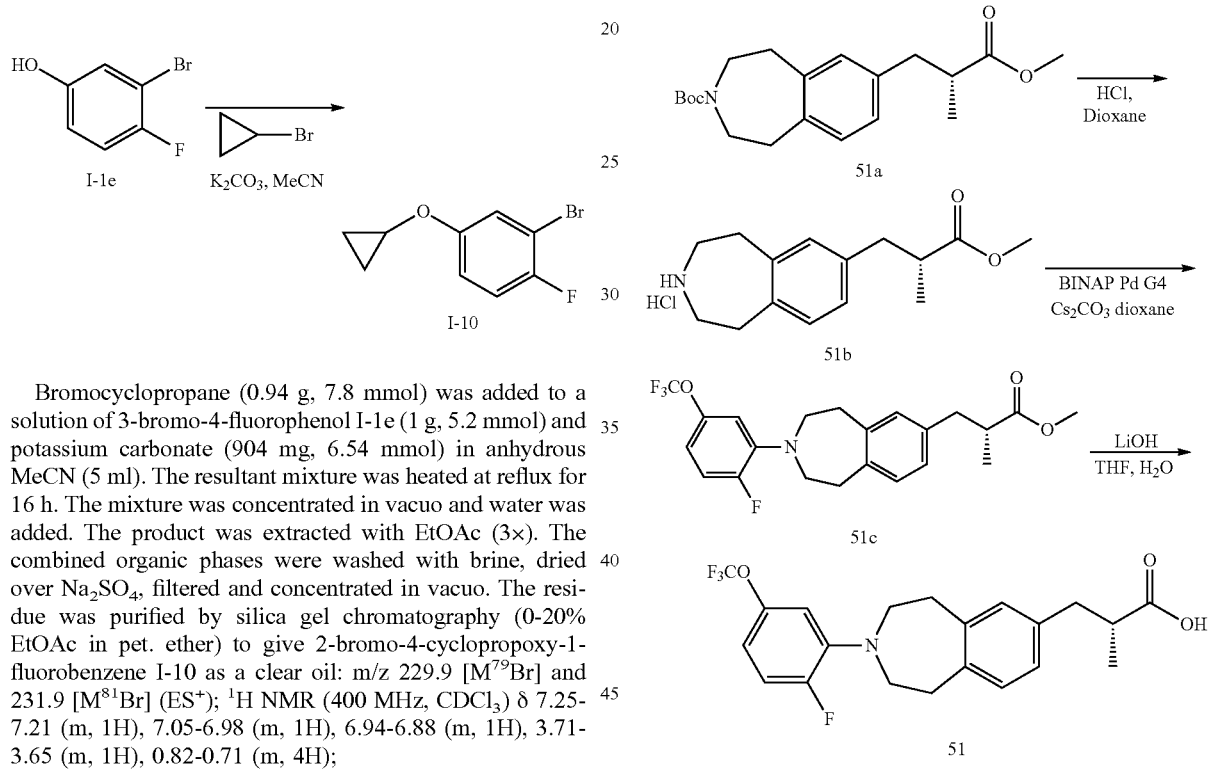

Bromocyclopropane (0.94 g, 7.8 mmol) was added to a solution of 3-bromo-4-fluorophenol I-1e (1 g, 5.2 mmol) and potassium carbonate (904 mg, 6.54 mmol) in anhydrous MeCN (5 ml). The resultant mixture was heated at reflux for 16 h. The mixture was concentrated in vacuo and water was added. The product was extracted with EtOAc (3×). The combined organic phases were washed with brine, dried over Na$_2$SO$_4$, filtered and concentrated in vacuo. The residue was purified by silica gel chromatography (0-20% EtOAc in pet. ether) to give 2-bromo-4-cyclopropoxy-1-fluorobenzene I-10 as a clear oil: m/z 229.9 [M$^{79}$Br] and 231.9 [M$^{81}$Br] (ES$^+$); $^1$H NMR (400 MHz, CDCl$_3$) δ 7.25-7.21 (m, 1H), 7.05-6.98 (m, 1H), 6.94-6.88 (m, 1H), 3.71-3.65 (m, 1H), 0.82-0.71 (m, 4H);

Experimental Scheme 14

Compound 51 (R)-3-(3-(2-fluoro-5-(trifluoromethoxy)phenyl)-2,3,4,5-tetrahydro-1H-benzo[d]azepin-7-yl)-2-methylpropanoic Acid

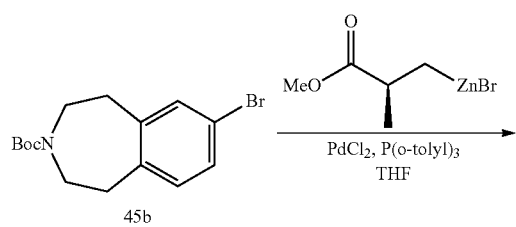

a) Procedure for the Preparation of 51a tert-Butyl 7-bromo-1,2,4,5-tetrahydro-3H-benzo[d]azepine-3-carboxylate 45b (130 mg, 0.4 mmol), PdCl$_2$ (3.5 mg, 0.020 mmol), tri-O-tolylphosphine (12 mg, 0.040 mmol) and anhydrous THF (2.0 mL) were added to a sealed vial. The vial was evacuated and back-filled with argon 3 times. A solution of (S)-(3-methoxy-2-methyl-3-oxopropyl)

zinc(II) bromide in THF (0.5 M, 1.6 mL, 0.8 mmol) was added and the mixture was heated at reflux. After 3 h, the reaction mixture was cooled to RT, filtered through celite and concentrated in vacuo. The residue was purified by silica gel chromatography (1-15% EtOAc in pet. ether) to afford tert-butyl (R)-7-(3-methoxy-2-methyl-3-oxopropyl)-1,2,4,5-tetrahydro-3H-benzo[d]azepine-3-carboxylate 51a as a light yellow oil. $^1$H NMR (400 MHz, CDCl$_3$) δ 7.02 (d, J=7.5 Hz, 1H), 6.94-6.87 (m, 2H), 3.65 (s, 3H), 3.58-3.48 (m, 4H), 2.98 (dd, J=13.4, 6.7 Hz, 1H), 2.90-2.80 (m, 4H), 2.76-2.66 (m, 1H), 2.60 (dd, J=13.4, 7.8 Hz, 1H), 1.48 (s, 9H), 1.15 (d, J=6.9 Hz, 3H); ESI-HRMS calcd for C$_{20}$H$_{29}$NO$_4$Na (M+Na$^+$) 370.1994, found 370.1991.

b) Procedure for the Preparation of 51b

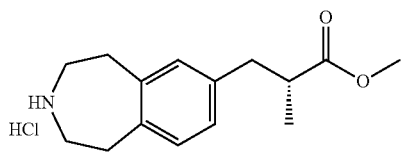 [SMILES: Cl ; COC(=O)[C@H](C)Cc1ccc2c(c1)CCNCC2]

A solution of HCl in dioxane (4 M, 0.51 mL, 2.04 mmol) was added to a solution of tert-butyl (R)-7-(3-methoxy-2-methyl-3-oxopropyl)-1,2,4,5-tetrahydro-3H-benzo[d]azepine-3-carboxylate 51a (71 mg, 0.20 mmol) in anhydrous dioxane (0.5 mL) at 0° C. The reaction mixture was warmed to RT for 16 h. The reaction mixture was concentrated in vacuo to afford methyl (R)-2-methyl-3-(2,3,4,5-tetrahydro-1H-benzo[d]azepin-7-yl)propanoate hydrochloride 51b as a white solid: $^1$H NMR (400 MHz, CDCl$_3$) δ 9.97 (s, 2H), 7.06 (d, J=7.6 Hz, 1H), 7.01-6.97 (m, 1H), 6.96-6.92 (m, 1H), 3.64 (s, 3H), 3.43-3.29 (m, 4H), 3.28-3.14 (m, 4H), 2.98 (dd, J=13.3, 6.9 Hz, 1H), 2.76-2.66 (m, 1H), 2.62 (dd, J=13.3, 7.5 Hz, 1H), 1.15 (d, J=6.9 Hz, 3H); ESI-HRMS calcd for C$_{15}$H$_{22}$NO$_2$ (M+H$^+$) 248.1645, found 248.1656.

c) Procedure for the Preparation of 51c

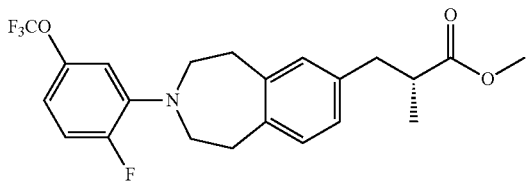 [SMILES: COC(=O)[C@H](C)Cc1ccc2c(c1)CCN(c1cc(OC(F)(F)F)ccc1F)CC2]

A vial under argon was charged with methyl (R)-2-methyl-3-(2,3,4,5-tetrahydro-1H-benzo[d]azepin-7-yl)propanoate hydrochloride 51 b (53 mg, 0.19 mmol), 2-bromo-1-fluoro-4-(trifluoromethoxy)benzene (68 mg, 0.26 mmol) cesium carbonate (186 mg, 0.57 mmol), Pd-BINAP G4 precatalyst (7 mg, 4 mol %) and anhydrous dioxane (2 ml). The vial was sealed, evacuated and back filled with argon three times, then heated at 100° C. for 48 h. The reaction was cooled and water was added. The product was extracted with EtOAc (3×). The combined organic phases were washed with brine, dried over Na$_2$SO$_4$, filtered and concentrated in vacuo. The residue was purified by silica gel chromatography (0-10% EtOAc in pet. ether) to afford methyl (R)-3-(3-(2-fluoro-5-(trifluoromethoxy)phenyl)-2,3,4,5-tetrahydro-1H-benzo[d]azepin-7-yl)-2-methylpropanoate 51c as a colourless oil: $^1$H NMR (400 MHz, CDCl$_3$) δ 7.05 (d, J=7.6 Hz, 1H), 7.00 (dd, J=12.2, 8.8 Hz, 1H), 6.96-6.92 (m, 2H), 6.76 (dd, J=7.3, 2.6 Hz, 1H), 6.74-6.69 (m, 1H), 3.65 (s, 3H), 3.32 (dd, J=5.2, 2.8 Hz, 4H), 3.06-2.96 (m, 5H), 2.78-2.68 (m, 1H), 2.61 (dd, J=13.4, 7.8 Hz, 1H), 1.16 (d, J=6.9 Hz, 3H); ESI-HRMS calcd for C$_{22}$H$_{23}$F$_4$NO$_3$Na (M+Na$^+$) 448.1506, found 448.1510.

d) Procedure for the Preparation of 51 (R)-3-(3-(2-fluoro-5-(trifluoromethoxy)phenyl)-2,3,4,5-tetrahydro-1H-benzo[d]azepin-7-yl)-2-methylpropanoic Acid

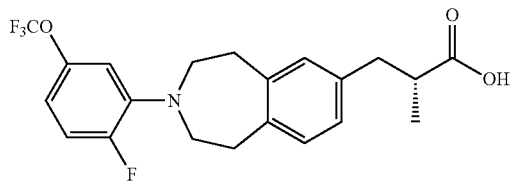 [SMILES: C[C@H](Cc1ccc2c(c1)CCN(c1cc(OC(F)(F)F)ccc1F)CC2)C(=O)O]

(R)-3-(3-(2-fluoro-5-(trifluoromethoxy)phenyl)-2,3,4,5-tetrahydro-1H-benzo[d]azepin-7-yl)-2-methylpropanoic acid 51 was prepared from methyl (R)-3-(3-(2-fluoro-5-(trifluoromethoxy)phenyl)-2,3,4,5-tetrahydro-1H-benzo[d]azepin-7-yl)-2-methylpropanoate 51c using a procedure essentially the same as for compound 45: 1H NMR (400 MHz, CDCl$_3$) δ 7.06 (d, J=7.4 Hz, 1H), 7.03-6.94 (m, 3H), 6.76 (dd, J=7.2, 2.6 Hz, 1H), 6.74-6.68 (m, 1H), 3.36-3.27 (m, 4H), 3.08-2.99 (m, 5H), 2.81-2.71 (m, 1H), 2.66-2.58 (m, 1H), 1.19 (d, J=6.9 Hz, 3H), COOH not observed; ESI-HRMS calcd for C$_{21}$H$_{22}$F$_4$NO$_3$ (M+Na$^+$) 412.1530, found 412.1535.

Human GPR120 pEC$_{50}$: 6.3

Experimental Scheme 15

Compound 52 2-(3-(2-fluoro-5-(trifluoromethoxy)phenyl)-2,3,4,5-tetrahydro-1H-benzo[d]azepin-7-yl)cyclopropanecarboxylic Acid

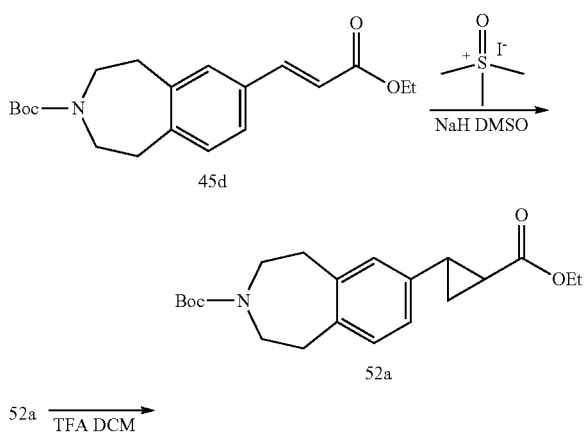

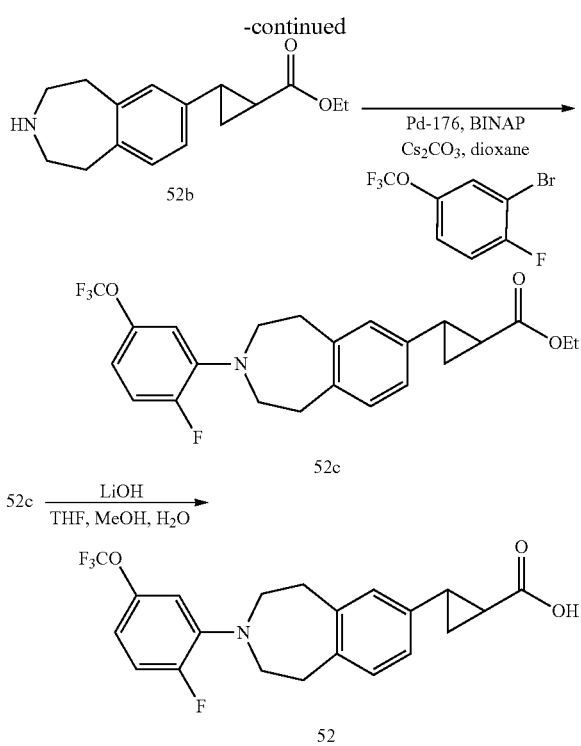

52 a) Procedure for the Preparation of 52a

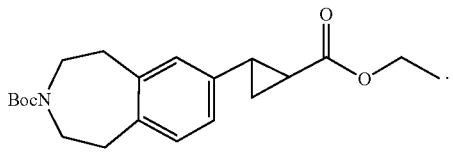 [SMILES: CCOC(=O)C1CC1c1ccc2c(c1)CCN(C(=O)OC(C)(C)C)CC2]

To a solution of trimethylsulfoxonium iodide (0.22 g, 1.0 mmol) in DMSO (5 ml) was added sodium hydride (0.04 g, 0.89 mmol) portion wise. The reaction was stirred at RT for 1 h. A solution of tert-butyl (E)-7-(3-ethoxy-3-oxoprop-1-en-1-yl)-1,2,4,5-tetrahydro-3H-benzo[d]azepine-3-carboxylate 45d (0.22 g, 0.64 mmol) in DMSO (5 ml) was added dropwise and the reaction was stirred at RT for 20 h. In a separate flask sodium hydride (0.05 g, 1.3 mmol) was added portionwise to a solution of trimethylsulfoxonium iodide (0.31 g, 1.4 mmol) in DMSO (5 ml). This mixture was stirred for 1 h before adding to the original reaction mixture dropwise. The resultant mixture was stirred at RT for 20 h. Brine (20% w/w, 100 ml) was added and the product was extracted with TBME (4×50 ml). The combined organic phases were washed with brine (20% w/w, 70 ml), dried over MgSO$_4$, filtered and concentrated in vacuo. The residue was purified by silica gel chromatography (0-20% EtOAc/isohexane) to afford tert-butyl 7-(2-(ethoxycarbonyl)cyclopropyl)-4,5-dihydro-1H-benzo[d]azepine-3(2H)-carboxylate 52a as a colourless oil: m/z 260 [M-CO$_2$$^t$Bu] (ES$^+$); $^1$H NMR (500 MHz, CDCl$_3$) δ δ 7.04 (d, J=7.6 Hz, 1H), 6.92-6.85 (m, 2H), 4.18 (q, J=7.2 Hz, 2H), 3.55 (s, 4H), 2.87 (s, 4H), 2.49 (ddd, J=9.2, 6.5, 4.1 Hz, 1H), 1.96-1.85 (m, 1H), 1.62-1.56 (m, 1H), 1.50 (s, 9H), 1.31-1.28 (m, 4H).

b) Procedure for the Preparation of 52b

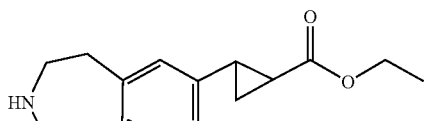

To a solution of tert-butyl 7-(2-(ethoxycarbonyl)cyclopropyl)-4,5-dihydro-1H-benzo[d]azepine-3(2H)-carboxylate 52a (0.124 g, 0.345 mmol) in DCM (5 ml) was added TFA (0.266 ml, 3.45 mmol). The resultant mixture was stirred at RT for 1 h. The reaction mixture was diluted with MeOH (20 ml) and MP-carbonate resin (4.1 g, 2.98 mmol/g) was added and the mixture was stirred for 15 min. The mixture was filtered and the filtrate was concentrated under reduced pressure to yield ethyl 2-(2,3,4,5-tetrahydro-1H-benzo[d]azepin-7-yl)cyclopropanecarboxylate 52b as a colourless oil: m/z 260 [M+H$^+$] (ES$^+$); $^1$H NMR (500 MHz, CDCl$_3$) δ 7.09-7.04 (m, 1H), 6.93-6.88 (m, 2H), 4.28 (s, 1H), 4.19 (q, J=7.2 Hz, 2H), 3.21-3.10 (m, 4H), 3.10-3.03 (m, 4H), 2.49 (ddd, J=9.1, 6.5, 4.1 Hz, 1H), 1.90 (ddd, J=8.4, 5.3, 4.1 Hz, 1H), 1.60 (ddd, J=9.2, 5.3, 4.6 Hz, 1H), 1.34-1.26 (m, 4H).

c) Procedure for the Preparation of 52c

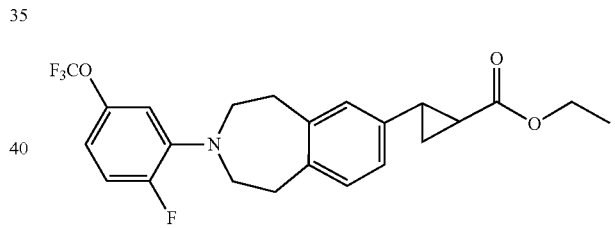

A via was charged with cesium carbonate (85 mg, 0.26 mmol), BINAP (3 mg, 5 μmol) and Pd-176 (4.35 mg, 5.21 μmol) The vial was sealed, evacuated and back filled with nitrogen three times. A solution of ethyl 2-(2,3,4,5-tetrahydro-1H-benzo[d]azepin-7-yl)cyclopropanecarboxylate 52b (0.045 g, 0.174 mmol) and 2-bromo-1-fluoro-4-(trifluoromethoxy)benzene (49.4 mg, 0.191 mmol) in dioxane (2 ml) was added and the vial was evacuated and back filled with nitrogen three times. The reaction was heated at 90° C. for 16 h. An additional portion of Pd-176 (4 mg, 5 μmol) and cesium carbonate (85 mg, 0.26 mmol) was added and the mixture was heated at 100° C. for 20 h. The reaction was cooled and water (2 ml) was added. The product was extracted with DCM (3×5 ml). The combined organics phases were passed through a hydrophobic membrane and concentrated in vacuo. The residue was purified by chromatography on silica gel (0-10% EtOAc/isohexane) to afford ethyl 2-(3-(2-fluoro-5-(trifluoromethoxy)phenyl)-2,3,4,5-tetrahydro-1H-benzo[d]azepin-7-yl)cyclopropanecarboxylate 52c as a colourless oil: m/z 438 [M+H]$^+$ (ES$^+$); $^1$H NMR (500 MHz, CDCl$_3$) δ 7.11-7.06 (m, 1H), 7.03 (dd, J=12.1, 8.8 Hz, 1H), 6.93-6.89 (m, 2H), 6.80-6.77 (m, 1H), 6.76-6.71 (m, 1H), 4.20 (q, J=7.1 Hz, 2H), 3.39-3.29 (m, 4H), 3.09-3.00 (m, 4H), 2.51 (ddd, J=9.2, 6.5, 4.2 Hz, 1H), 1.91 (ddd, J=8.4, 5.3, 4.2 Hz, 1H), 1.61 (ddd, J=9.2, 5.3, 4.5 Hz, 1H), 1.34-1.31 (m, 1H), 1.31 (t, J=7.1 Hz, 3H).

d) Procedure for the Preparation of 52 2-(3-(2-fluoro-5-(trifluoromethoxy)phenyl)-2,3,4,5-tetrahydro-1H-benzo[d]azepin-7-yl)cyclopropanecarboxylic Acid

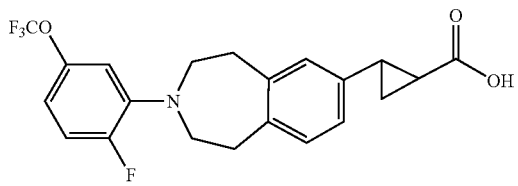 [SMILES: O=C(O)C1CC1c1ccc2c(c1)CCN(c1cc(OC(F)(F)F)ccc1F)CC2]

To a solution of ethyl 2-(3-(2-fluoro-5-(trifluoromethoxy)phenyl)-2,3,4,5-tetrahydro-1H-benzo[d]azepin-7-yl)cyclopropanecarboxylate 52c (0.03 g, 0.069 mmol) in THF (2 ml) and MeOH (1 ml) was added a solution of lithium hydroxide (4.93 mg, 0.206 mmol) in water (1 ml). The resultant mixture was stirred at 40° C. for 2 h. The reaction was cooled and concentrated in vacuo. Water (5 ml) was added and the pH was adjusted to 1 with 1 M HCl (0.5 ml). The crude was extracted with DCM (2×5 ml). The combined organics phases were passed through a hydrophobic frit and concentrated in vacuo. The residue was purified by reverse-phase flash chromatography (C18, 15-75% MeCN in water, 0.1% Formic Acid) to afford 2-(3-(2-fluoro-5-(trifluoromethoxy)phenyl)-2,3,4,5-tetrahydro-1H-benzo[d]azepin-7-yl)cyclopropanecarboxylic acid 52 as a colourless solid: m/z 410.3 [M+H]$^+$ (ES$^+$); $^1$H NMR (500 MHz, DMSO-d$_6$) 12.28 (s, 1H), 7.24 (dd, J=8.8, 12.7 Hz, 1H), 7.07 (d, J=7.7 Hz, 1H), 6.99-6.93 (m, 2H), 6.92 (dd, J=2.0, 7.7 Hz, 1H), 6.89-6.83 (m, 1H), 3.31-3.25 (m, 4H), 2.99-2.94 (m, 4H), 2.33 (ddd, J=4.0, 6.5, 9.2 Hz, 1H), 1.77 (ddd, J=4.0, 5.3, 8.3 Hz, 1H), 1.39 (ddd, J=4.2, 5.3, 9.2 Hz, 1H), 1.31 (ddd, J=4.2, 6.5, 8.3 Hz, 1H);

Human GPR120 pEC$_{50}$: 6.9

The following compounds were prepared using appropriate starting materials in an analogous procedure to that described in Experimental Scheme 15.

Experimental Scheme 16

Compound 54 3-(2-(2-Fluoro-5-(trfluoromethoxy)phenyl)-2,3,4,5-tetrahydro-1H-benzo[c]azepin-7-yl)propanoic Acid

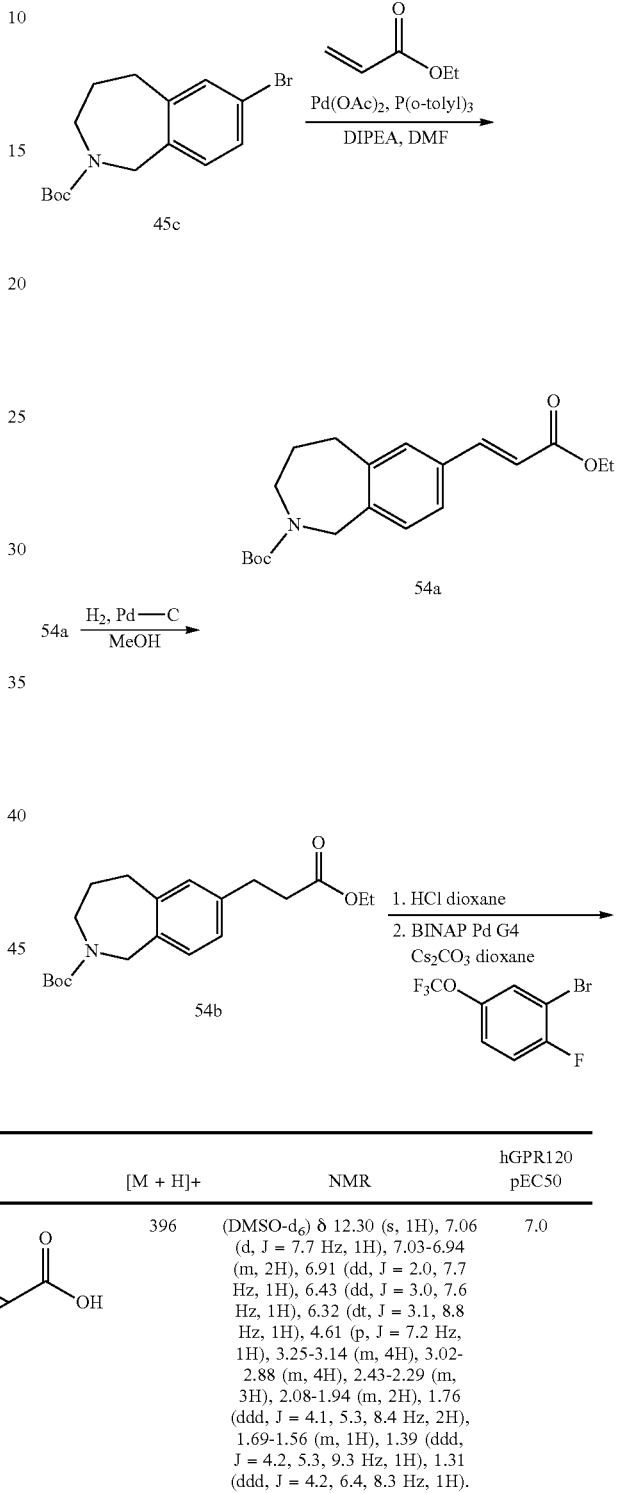

| Compound | Structure | [M + H]+ | NMR | hGPR120 pEC50 |
|---|---|---|---|---|
| 53 | 3-(3-(5-cyclobutoxy-2-fluorophenyl)-2,3,4,5-tetrahydro-1H-benzo[d]azepin-7-yl)propanoic acid | 396 | (DMSO-d$_6$) δ 12.30 (s, 1H), 7.06 (d, J = 7.7 Hz, 1H), 7.03-6.94 (m, 2H), 6.91 (dd, J = 2.0, 7.7 Hz, 1H), 6.43 (dd, J = 3.0, 7.6 Hz, 1H), 6.32 (dt, J = 3.1, 8.8 Hz, 1H), 4.61 (p, J = 7.2 Hz, 1H), 3.25-3.14 (m, 4H), 3.02-2.88 (m, 4H), 2.43-2.29 (m, 3H), 2.08-1.94 (m, 2H), 1.76 (ddd, J = 4.1, 5.3, 8.4 Hz, 2H), 1.69-1.56 (m, 1H), 1.39 (ddd, J = 4.2, 5.3, 9.3 Hz, 1H), 1.31 (ddd, J = 4.2, 6.4, 8.3 Hz, 1H). | 7.0 |

-continued

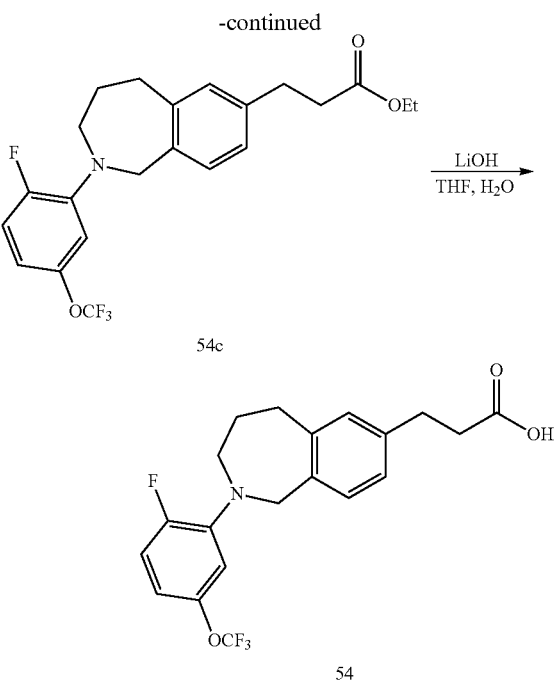

a) Procedure for the Preparation of 54a

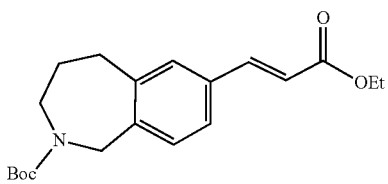 [SMILES: CCOC(=O)/C=C/c1ccc2c(c1)CCCN(C(=O)OC(C)(C)C)C2]

tert-Butyl (E)-7-(3-ethoxy-3-oxoprop-1-en-1-yl)-1,3,4,5-tetrahydro-2H-benzo[c]azepine-2-carboxylate 54 a was prepared from tert-butyl 7-bromo-1,3,4,5-tetrahydro-2H-benzo[c]azepine-2-carboxylate 45c using a procedure essentially the same as for compound 45d: $^1$H NMR (400 MHz, CDCl$_3$) δ 7.67-7.61 (m, 1H), 7.34-7.29 (m, 2H), 7.21-7.17 (m, 1H), 6.45-6.38 (m, 1H), 4.42 (s, 1H), 4.37 (s, 1H), 4.26 (q, J=7.1 Hz, 2H), 3.75-3.64 (m, 2H), 2.98-2.92 (m, 2H), 1.82-1.73 (m, 2H), 1.39 (s, 9H), 1.33 (t, J=7.1 Hz, 3H); ESI-HRMS calcd for C$_{20}$H$_{27}$NNaO$_4$ (M+Na$^+$) 368.1832, found 368.1846.

b) Procedure for the Preparation of 54b

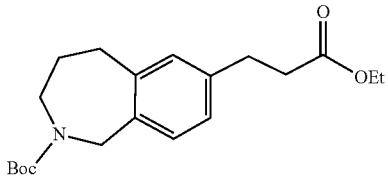 [SMILES: CCOC(=O)CCc1ccc2c(c1)CCCN(C(=O)OC(C)(C)C)C2]

Pd/C (14.6 mg, 10 mol %) was added to a solution of tert-butyl (E)-7-(3-ethoxy-3-oxoprop-1-en-1-yl)-1,3,4,5-tetrahydro-2H-benzo[c]azepine-2-carboxylate 54a (112 mg, 0.32 mmol) in EtOAc (5 ml). The mixture was flushed with argon for 15 minutes and stirred under a hydrogen atmosphere for 16 h. The mixture was filtered through a pad of celite and the filtrate was concentrated in vacuo. The residue was purified by chromatography on silica (0-20% EtOAc in pet. ether) to afford tert-butyl 7-(3-ethoxy-3-oxopropyl)-1,2,4,5-tetrahydro-3H-benzo[d]azepine-3-carboxylate 54b as a colourless oil: $^1$H NMR (400 MHz, CDCl$_3$) δ δ 7.04-6.99 (m, 1H), 6.97-6.92 (m, 2H), 4.12 (q, J=7.2 Hz, 2H), 3.52 (s, 4H), 2.91-2.80 (m, 6H), 2.61-2.56 (m, 2H), 1.47 (s, 9H), 1.23 (t, J=7.2 Hz, 3H); ESI-HRMS calcd for C$_{20}$H$_{29}$NNaO$_4$ (M+Na$^+$) 370.1989 found 370.1999.

c) Procedure for the Preparation of 54c

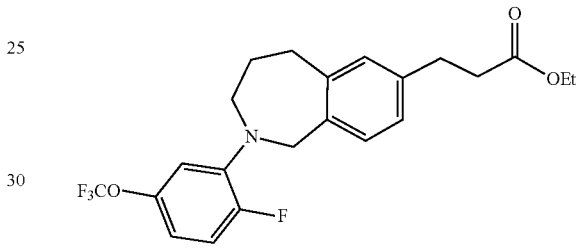

Step 1.

tert-Butyl 7-(3-ethoxy-3-oxopropyl)-1,3,4,5-tetrahydro-2H-benzo[c]azepine-2-carboxylate 54b (60 mg, 0.17 mmol) was added to a solution of HCl in dioxane (4 M, 2 ml). The mixture was stirred at RT for 16 h and then concentrated in vacuo to afford ethyl 3-(2,3,4,5-tetrahydro-1H-benzo[c]azepin-7-yl)propanoate hydrochloride, which was taken on to the next step without purification.

Step 2.

A vial under argon was charged with afford ethyl 3-(2,3,4,5-tetrahydro-1H-benzo[c]azepin-7-yl)propanoate hydrochloride (20 mg, 0.07 mmol), 2-bromo-1-fluoro-4-(trifluoromethoxy)benzene (27 mg, 0.11 mmol), cesium carbonate (68 mg, 0.21 mmol), Pd-BINAP G4 precatalyst (3 mg, 4 mol %) and anhydrous dioxane (2 ml). The vial was sealed, evacuated and back filled with argon three times, then heated at 100° C. for 48 h. The reaction was cooled and water was added. The product was extracted with EtOAc (3x). The combined organic phases were washed with brine and dried over Na$_2$SO$_4$, filtered and concentrated in vacuo. The residue was purified by silica gel chromatography (0-10% EtOAc in pet. ether) to afford ethyl 3-(2-(2-fluoro-5-(trifluoromethoxy)phenyl)-2,3,4,5-tetrahydro-1H-benzo[c]azepin-7-yl)propanoate 54c as a colourless oil: $^1$H NMR (400 MHz, CDCl$_3$) δ 7.15-7.11 (m, 1H), 7.00-6.89 (m, 3H), 6.72-6.67 (m, 1H), 6-57-6.52 (m, 1H), 4.47 (s, 2H), 4.14-4.07 (m, 2H), 3.69-3.63 (m, 2H), 3.01-2.95 (m, 2H), 2.91-2.85 (m, 2H), 2.61-2.55 (m, 2H), 1.97-1.89 (m, 2H), 1.20 (t, J=7.1 Hz, 3H); ESI-HRMS calcd for C$_{22}$H$_{24}$F$_4$NO$_3$ (M+H$^+$) 426.1687, found 426.1676.

d) Procedure for the Preparation of 54 3-(2-(2-Fluoro-5-(trifluoromethoxy)phenyl)-2,3,4,5-tetrahydro-1H-benzo[c]azepin-7-yl)propanoic Acid

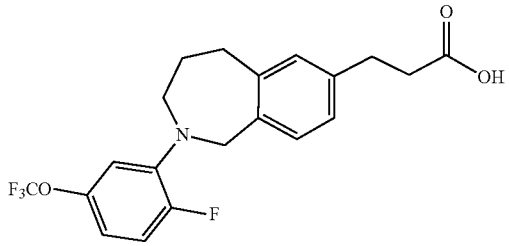 [SMILES: O=C(O)CCc1ccc2c(c1)CCCN(c1cc(OC(F)(F)F)ccc1F)C2]

3-(2-(2-Fluoro-5-(trifluoromethoxy)phenyl)-2,3,4,5-tetrahydro-1H-benzo[c]azepin-7-yl)propanoic acid 54 was prepared from ethyl 3-(2-(2-fluoro-5-(trifluoromethoxy)phenyl)-2,3,4,5-tetrahydro-1H-benzo[c]azepin-7-yl)propanoate 54c using a procedure essentially the same as for compound 45: $^1$H NMR (400 MHz, CDCl$_3$) δ 7.14 (d, J=7.1 Hz, 1H), 7.00-6.89 (m, 3H), 6.73-6.68 (m, 1H), 6.58-6.53 (m, 1H), 4.47 (s, 2H), 3.69-3.63 (m, 2H), 3.01-2.96 (m, 2H), 2.89 (t, J=7.8 Hz, 2H), 2.96-2.61 (m, 2H), 1.98-1.90 (m, 2H); ESI-HRMS calcd for $C_{20}H_{20}F_4NO_3$ (M+H$^+$) 398.1374 found 398.1391.

Human GPR120 pEC$_{50}$: 6.7

The invention claimed is:

1. A compound of formula (I):

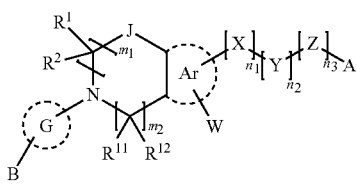

wherein Ar is a fused benzo group;
$m_1$ is 1 and $m_2$ is 2;
J is —C(R$^{21}$R$^{22}$)—;
X is —O—, —S— or —C(R$^{31}$R$^{32}$)—, Y is —O— or —C(R$^{41}$R$^{42}$)—, Z is —C(R$^{51}$R$^{52}$)—, and $n_1$, $n_2$ and $n_3$ are independently selected from 0 or 1 with the proviso that at least one of $n_1$, $n_2$ and $n_3$ must be 1 and at least one of X, Y or Z must be —C(R$^{31}$R$^{32}$)—, —C(R$^{41}$R$^{42}$)—, or —C(R$^{51}$R$^{52}$)— respectively;
when X and Y are —C(R$^{31}$R$^{32}$)— and —C(R$^{41}$R$^{42}$)— respectively, R$^{31}$ and R$^{41}$ may be combined to form, together with X and Y, a (C$_3$-C$_5$)cycloalkyl ring which may be optionally substituted by (C$_1$-C$_3$)alkyl or halo;
when Y and Z are —C(R$^{41}$R$^{42}$)— and —C(R$^{51}$R$^{52}$)— respectively, R$^{41}$ and R$^{51}$ may be combined to form, together with Y and Z, a (C$_3$-C$_5$)cycloalkyl ring which may be optionally substituted by (C$_1$-C$_3$)alkyl or halo;
when X, Y and Z are —C(R$^{31}$R$^{32}$)—, —C(R$^{41}$R$^{42}$)— and —C(R$^{51}$R$^{52}$)— respectively, R$^{31}$ and R$^{51}$ may form, together with X, Y and Z a (C$_4$-C$_7$)cycloalkyl ring which may be optionally substituted by (C$_1$-C$_3$)alkyl or halo;
R$^1$, R$^2$, R$^{11}$, R$^{12}$, R$^{21}$, R$^{22}$, R$^{31}$, R$^{32}$, R$^{41}$, R$^{42}$, R$^{51}$, and R$^{52}$ are independently selected from hydrogen, deuterium, halo, or (C$_1$-C$_3$)alkyl optionally substituted by halo;

A is —CO$_2$H, —CO$_2$R$^3$, —CH$_2$OH, tetrazolyl, or 3-hydroxyisoxazol-5-yl;
R$^3$ is (C$_1$-C$_6$)alkyl, or (C$_1$-C$_6$)cycloalkyl;
Ar is optionally substituted 1, 2 or 3 times by W, where W is (C$_1$-C$_{10}$)alkyl, (C$_2$-C$_{10}$)alkenyl, (C$_2$-C$_{10}$)alkynyl, (C$_1$-C$_{10}$)alkoxy, (C$_2$-C$_{10}$)dialkylamino, (C$_1$-C$_{10}$)alkylthio, (C$_2$-C$_{10}$)heteroalkyl, (C$_3$-C$_{10}$)cycloalkyl, (C$_3$-C$_{10}$)heterocycloalkyl, halo, (C$_1$-C$_{10}$)haloalkyl, (C$_1$-C$_{10}$)perhaloalkyl, optionally substituted aryl, optionally substituted heteroaryl, or optionally substituted arylalkyl, and when Ar is substituted by a plurality of substituents, each substituent is selected independently;
G is an optionally substituted phenyl ring;
G is optionally substituted one or more times by B, where B is (C$_1$-C$_{10}$)alkyl, (C$_2$-C$_{10}$)alkenyl, (C$_2$-C$_{10}$)alkynyl, (C$_1$-C$_{10}$)alkoxy, (C$_2$-C$_{10}$)dialkylamino, (C$_1$-C$_{10}$)alkylthio, (C$_2$-C$_{10}$)heteroalkyl, (C$_3$-C$_{10}$)cycloalkyl, (C$_3$-C$_{10}$)heterocycloalkyl, halo, (C$_1$-C$_{10}$)haloalkyl, (C$_1$-C$_{10}$)perhaloalkyl, optionally substituted aryl, optionally substituted heteroaryl, optionally substituted arylalkyl, cyano, or E-M where E is —O—, —S— or —N(R$^4$)— and M is optionally substituted (C$_1$-C$_7$)alkyl, (C$_3$-C$_7$)cycloalkyl, fluoro(C$_1$-C$_3$)alkyl, a 5- to 10-membered heterocyclic group or an optionally substituted 6- to 10-membered aryl group, and when G is substituted by a plurality of substituents, each substituent is selected independently;
R$^4$ is hydrogen, deuterium, or (C$_1$-C$_3$)alkyl optionally substituted by halo;
or a pharmaceutically acceptable salt thereof, or corresponding N-oxide.

2. A compound according to claim 1 wherein R$^1$, R$^2$, R$^{11}$, R$^{12}$, R$^{21}$ and R$^{22}$ are hydrogen.

3. A compound according to claim 1 which is a compound of formula (Id):

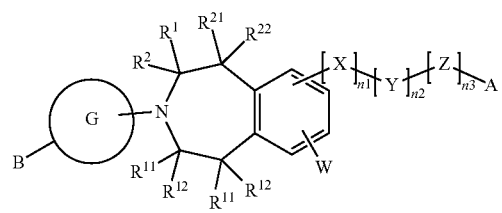

R$^1$, R$^2$, R$^{11}$, R$^{12}$, R$^{21}$ and R$^{22}$ are hydrogen;
$n_1$ is 0, Y is —C(R$^{41}$R$^{42}$)— and Z is —C(R$^{51}$R$^{52}$)—, and $n_2$ and $n_3$ are independently selected from 0 or 1 with the proviso that at least one of $n_2$ and $n_3$ must be 1;
when Y and Z are —C(R$^{41}$R$^{42}$)— and —C(R$^{51}$R$^{52}$)— respectively, R$^{41}$ and R$^{51}$ may be combined to form, together with Y and Z, a (C$_3$-C$_6$)cycloalkyl ring which may be optionally substituted by (C$_1$-C$_3$)alkyl or halo;
R$^{31}$, R$^{32}$, R$^{41}$, R$^{42}$, R$^{51}$, and R$^{52}$ are independently selected from hydrogen, deuterium, halo, or (C$_1$-C$_3$) alkyl optionally substituted by halo;
A is —CO$_2$H;
the phenyl ring is optionally substituted 1, 2 or 3 times by W where W is (C$_1$-C$_{10}$)alkyl, (C$_2$-C$_{10}$)alkenyl, (C$_2$-C$_{10}$)alkynyl, (C$_1$-C$_{10}$)alkoxy, (C$_2$-C$_{10}$)dialkylamino, (C$_1$-C$_{10}$)alkylthio, (C$_2$-C$_{10}$)heteroalkyl, (C$_3$-C$_{10}$)cycloalkyl, (C$_3$-C$_{10}$)heterocycloalkyl, halo, (C$_1$-C$_{10}$)haloalkyl, (C$_1$-C$_{10}$)perhaloalkyl, optionally substituted aryl, optionally substituted heteroaryl, or optionally substituted arylalkyl and where when the phenyl ring is substituted by a plurality of substituents, each substituent is selected independently;

G is an optionally substituted phenyl ring;

G is optionally substituted one or more times by B where B is $(C_1-C_{10})$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, optionally substituted arylalkyl, cyano, or E-M where E is —O—, —S— or —N($R^4$)— and M is optionally substituted $(C_1-C_7)$alkyl, $(C_3-C_7)$cycloalkyl, fluoro$(C_1-C_3)$alkyl, a 5- to 10-membered heterocyclic group or an optionally substituted 6- to 10-membered aryl group, and where when G is substituted by a plurality of substituents, each substituent is selected independently;

$R^4$ is hydrogen, deuterium, or $(C_1-C_3)$alkyl optionally substituted by halo;

or a pharmaceutically acceptable salt thereof, or corresponding N-oxide.

4. A compound according to claim 3 wherein X—Y—Z-A is —CH$_2$—CH$_2$—COOH, —CH$_2$CH(CH$_3$)COOH or

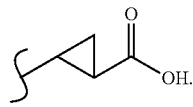

5. A compound according to claim 3 wherein W is optionally substituted $(C_1-C_6)$alkyl, $(C_3-C_6)$cycloalkyl, halo or optionally substituted $(C_1-C_6)$alkoxy, or wherein the phenyl ring is not substituted by W.

6. A compound according to claim 3 wherein G is substituted 1, 2 or 3 times by B.

7. A compound according to claim 1 wherein the compound is selected from the group consisting of:

3-(3-(2-fluoro-5-(trifluoromethoxy)phenyl)-2,3,4,5-tetrahydro-1H-benzo[d]azepin-7-yl)propanoic acid, 3-(3-(5-cyclobutoxy-2-fluorophenyl)-2,3,4,5-tetrahydro-1H-benzo[d]azepin-7-yl)propanoic acid, 3-(3-(5-cyclopropoxy-2-fluorophenyl)-2,3,4,5-tetrahydro-1H-benzo[d]azepin-7-yl)propanoic acid, 3-(3-(3-fluoro-5-isopropoxyphenyl)-2,3,4,5-tetrahydro-1H-benzo[d]azepin-7-yl)propanoic acid, 3-(3-(2-fluoro-5-isopropoxyphenyl)-2,3,4,5-tetrahydro-1H-benzo[d]azepin-7-yl)propanoic acid, 3-(3-(2-fluoro-5-phenoxyphenyl)-2,3,4,5-tetrahydro-1H-benzo[d]azepin-7-yl)propanoic acid, (R)-3-(3-(2-fluoro-5-(trifluoromethoxy)phenyl)-2,3,4,5-tetrahydro-1H-benzo[d]azepin-7-yl)-2-methylpropanoic acid, 2-(3-(2-fluoro-5-(trifluoromethoxy)phenyl)-2,3,4,5-tetrahydro-1H-benzo[d]azepin-7-yl)cyclopropanecarboxylic acid, 3-(3-(5-cyclobutoxy-2-fluorophenyl)-2,3,4,5-tetrahydro-1H-benzo[d]azepin-7-yl)propanoic acid, and 3-(2-(2-fluoro-5-(trifluoromethoxy)phenyl)-2,3,4,5-tetrahydro-1H-benzo[c]azepin-7-yl)propanoic acid;

or a pharmaceutically acceptable salt thereof.

8. A method of treating a subject suffering from or susceptible to, a disease or condition associated with GPR120 activity, which method comprises administering to the subject a therapeutically or prophylactically effective amount of a compound according to formula (I),

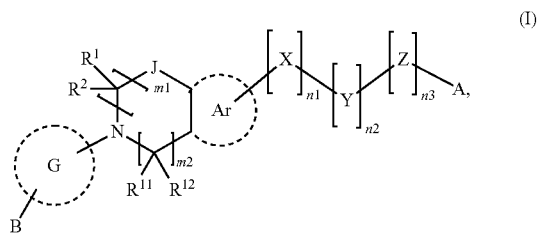

wherein Ar is a fused benzo group;

$m_1$ is 1 and $m_2$ is 2;

J is —C($R^{21}R^{22}$)—;

X is —O—, —S— or —C($R^{31}R^{32}$)—, Y is —O— or —C($R^{41}R^{42}$)—, Z is —C($R^{51}R^{52}$)—, and $n_1$, $n_2$ and $n_3$ are independently selected from 0 or 1 with the proviso that at least one of $n_1$, $n_2$ and $n_3$ must be 1 and at least one of X, Y or Z must be —C($R^{31}R^{32}$)—, —C($R^{41}R^{42}$)—, or —C($R^{51}R^{52}$)— respectively:

when X and Y are —C($R^{31}R^{32}$)— and —C($R^{41}R^{42}$)— respectively, $R^{31}$ and $R^{41}$ may be combined to form, together with X and Y, a $(C_3-C_5)$cycloalkyl ring which may be optionally substituted by $(C_1-C_3)$alkyl or halo;

when Y and Z are —C($R^{41}R^{42}$)— and —C($R^{51}R^{52}$)— respectively, $R^{41}$ and $R^{51}$ may be combined to form, together with Y and Z, a $(C_3-C_5)$cycloalkyl ring which may be optionally substituted by $(C_1-C_3)$alkyl or halo:

when X, Y and Z are —C($R^{31}R^{32}$), —C($R^{41}R^{42}$) and —C($R^{51}R^{52}$)— respectively, $R^{31}$ and $R^{51}$ may form, together with X, Y and Z a $(C_4-C_7)$cycloalkyl ring which may be optionally substituted by $(C_1-C_3)$alkyl or halo;

$R^1$, $R^2$, $R^{11}$, $R^{12}$, $R^{21}$, $R^{22}$, $R^{31}$, $R^{32}$, $R^{41}$, $R^{42}$, $R^{51}$, and $R^{52}$ are independently selected from hydrogen, deuterium, halo, or $(C_1-C_3)$alkyl optionally substituted by halo:

A is —CO$_2$H, —CO$_2R^3$, —CH$_2$OH, tetrazolyl, or 3-hydroxyisoxazol-5-yl;

$R^3$ is $(C_3-C_6)$alkyl, or $(C_1-C_6)$cycloalkyl;

Ar is optionally substituted 1, 2 or 3 times by W, where W is $(C_1-C_{10})$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_0)$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, or optionally substituted arylalkyl, and when Ar is substituted by a plurality of substituents, each substituent is selected independently;

G is an optionally substituted phenyl ring;

G is optionally substituted one or more times by B, where B is $(C_1-C_{10})$alkyl, $(C_2-C_{10})$alkenyl, $(C_2-C_{10})$alkynyl, $(C_1-C_{10})$alkoxy, $(C_2-C_{10})$dialkylamino, $(C_1-C_{10})$alkylthio, $(C_2-C_{10})$heteroalkyl, $(C_3-C_{10})$cycloalkyl, $(C_3-C_{10})$heterocycloalkyl, halo, $(C_1-C_{10})$haloalkyl, $(C_1-C_{10})$perhaloalkyl, optionally substituted aryl, optionally substituted heteroaryl, optionally substituted arylalkyl, cyano, or E-M where E is —O—, —S— or —N(R$^4$)— and M is optionally substituted (C$_1$-C$_7$) alkyl, (C$_3$-C$_7$)cycloalkyl, fluoro(C$_1$-C$_3$)alkyl, a 5- to 10-membered heterocyclic group or an optionally substituted 6- to 10-membered aryl group, and when G is substituted by a plurality of substituents, each substituent is selected independently;

R$^4$ is hydrogen, deuterium, or (C$_1$-C$_3$)alkyl optionally substituted by halo;

or a pharmaceutically acceptable salt thereof, or corresponding N-oxide; and wherein the disease or condition is selected from the group consisting of type 1 or 2 diabetes, obesity, hyperglycaemia, glucose intolerance, insulin resistance, hyperinsulinaemia, non-alcoholic steatohepatitis ("NASH"), diabetic nephropathy, diabetic retinopathy, and diabetic neuropathy.

9. A method for modulating circulating insulin concentration in a subject, comprising administering to the subject a therapeutically or prophylactically effective amount of a compound according to claim 1.

10. A pharmaceutical composition comprising a compound according to claim 1 and one or more pharmaceutically acceptable excipients.

11. A process for the preparation of a compound according to claim 1 comprising:
reacting a compound of formula (II)

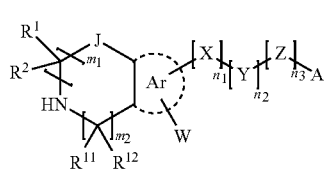

(II)

with a compound of formula (III)

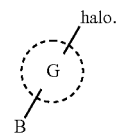

(III)

* * * * *

UNITED STATES PATENT AND TRADEMARK OFFICE
CERTIFICATE OF CORRECTION

PATENT NO. : 11,220,483 B2  
APPLICATION NO. : 16/496786  
DATED : January 11, 2022  
INVENTOR(S) : Jane Brown et al.

Page 1 of 1

It is certified that error appears in the above-identified patent and that said Letters Patent is hereby corrected as shown below:

In the Claims

At Claim 8, Column 126, Lines 7-17, delete " 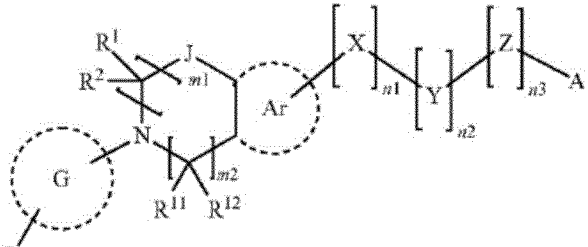 " and

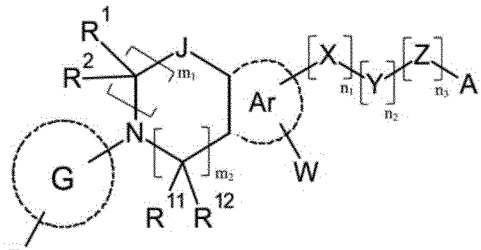

insert -- B                              -- in its place;

At Claim 8, Column 126, Line 49, delete "$(C_3-C_6)$alkyl" and insert --$(C_1-C_6)$alkyl-- in its place; and At Claim 8, Column 126, Line 53, delete "$(C_2-C_0)$heteroalkyl" and insert --$(C_2-C_{10})$heteroalkyl-- in its place.

Signed and Sealed this  
Twenty-sixth Day of April, 2022

Katherine Kelly Vidal  
*Director of the United States Patent and Trademark Office*